US011928859B2

(12) United States Patent
Nouri et al.

(10) Patent No.: US 11,928,859 B2
(45) Date of Patent: Mar. 12, 2024

(54) AUTOMATED IMAGE ANALYSIS FOR DIAGNOSING A MEDICAL CONDITION

(71) Applicant: BFLY OPERATIONS, INC., Burlington, MA (US)

(72) Inventors: Daniel Nouri, Burlington, MA (US); Alex Rothberg, Burlington, MA (US); Matthew de Jonge, Burlington, MA (US); Jimmy Jia, Burlington, MA (US); Jonathan M. Rothberg, Burlington, MA (US); Michal Sofka, Burlington, MA (US); David Elgena, Burlington, MA (US); Mark Michalski, Burlington, MA (US); Tomer Gafner, Burlington, MA (US); Abraham Neben, Burlington, MA (US)

(73) Assignee: BFLY OPERATIONS, INC., Burlington, MA (US)

( * ) Notice: Subject to any disclaimer, the term of this patent is extended or adjusted under 35 U.S.C. 154(b) by 0 days.

(21) Appl. No.: 17/975,268

(22) Filed: Oct. 27, 2022

(65) Prior Publication Data

US 2023/0117915 A1  Apr. 20, 2023

Related U.S. Application Data

(63) Continuation of application No. 15/626,954, filed on Jun. 19, 2017, now Pat. No. 11,540,808.
(Continued)

(51) Int. Cl.
*A61B 5/00* (2006.01)
*A61B 8/00* (2006.01)
(Continued)

(52) U.S. Cl.
CPC ............... *G06V 10/82* (2022.01); *A61B 8/02* (2013.01); *A61B 8/06* (2013.01); *A61B 8/065* (2013.01);
(Continued)

(58) Field of Classification Search
CPC .. A61B 8/02; A61B 8/06; A61B 8/065; A61B 8/085; A61B 8/4427; A61B 8/46;
(Continued)

(56) References Cited

U.S. PATENT DOCUMENTS

| 2004/0122707 A1* | 6/2004 | Sabol .................. G16H 10/60 707/999.009 |
| 2011/0060215 A1* | 3/2011 | Tupin, Jr. ............ A61B 5/1075 600/407 |

(Continued)

FOREIGN PATENT DOCUMENTS

| JP | 2013192569 A | 9/2013 |
| KR | 10-2016-0025891 A | 3/2016 |
| KR | 10-2016-0046670 A | 4/2016 |

OTHER PUBLICATIONS

Extended European Search Report issued in corresponding European Patent Application No. 23153155.9 dated May 3, 2023 (8 pages).

*Primary Examiner* — Joel F Brutus
(74) *Attorney, Agent, or Firm* — Osha Bergman Watanabe & Burton LLP

(57) ABSTRACT

Aspects of the technology described herein relate to techniques for guiding an operator to use an ultrasound device. Thereby, operators with little or no experience operating ultrasound devices may capture medically relevant ultrasound images and/or interpret the contents of the obtained ultrasound images. For example, some of the techniques disclosed herein may be used to identify a particular anatomical view of a subject to image with an ultrasound
(Continued)

device, guide an operator of the ultrasound device to capture an ultrasound image of the subject that contains the particular anatomical view, and/or analyze the captured ultrasound image to identify medical information about the subject.

20 Claims, 28 Drawing Sheets

Related U.S. Application Data

(60) Provisional application No. 62/463,094, filed on Feb. 24, 2017, provisional application No. 62/453,696, filed on Feb. 2, 2017, provisional application No. 62/445,195, filed on Jan. 11, 2017, provisional application No. 62/434,980, filed on Dec. 15, 2016, provisional application No. 62/384,187, filed on Sep. 6, 2016, provisional application No. 62/384,144, filed on Sep. 6, 2016, provisional application No. 62/352,382, filed on Jun. 20, 2016.

(51) Int. Cl.
| | |
|---|---|
| *A61B 8/02* | (2006.01) |
| *A61B 8/06* | (2006.01) |
| *A61B 8/08* | (2006.01) |
| *G06F 18/2413* | (2023.01) |
| *G06T 7/00* | (2017.01) |
| *G06T 7/70* | (2017.01) |
| *G06T 11/60* | (2006.01) |
| *G06T 19/00* | (2011.01) |
| *G06V 10/44* | (2022.01) |
| *G06V 10/82* | (2022.01) |
| *G06V 30/19* | (2022.01) |
| *G06V 30/194* | (2022.01) |
| *G06V 40/60* | (2022.01) |
| *A61B 34/20* | (2016.01) |
| *A61B 90/00* | (2016.01) |

(52) U.S. Cl.
CPC ............ *A61B 8/085* (2013.01); *A61B 8/4427* (2013.01); *A61B 8/46* (2013.01); *A61B 8/52* (2013.01); *A61B 8/5207* (2013.01); *A61B 8/5223* (2013.01); *G06F 18/24133* (2023.01); *G06T 7/0012* (2013.01); *G06T 7/0014* (2013.01); *G06T 7/70* (2017.01); *G06T 11/60* (2013.01); *G06T 19/006* (2013.01); *G06V 10/454* (2022.01); *G06V 30/19173* (2022.01); *G06V 30/194* (2022.01); *G06V 40/67* (2022.01); *A61B 8/0833* (2013.01); *A61B 8/0883* (2013.01); *A61B 8/4263* (2013.01); *A61B 8/463* (2013.01); *A61B 8/5215* (2013.01); *A61B 2034/2065* (2016.02); *A61B 2090/365* (2016.02); *A61B 2090/378* (2016.02); *A61B 2090/3937* (2016.02); *G06T 2207/10132* (2013.01); *G06T 2207/20081* (2013.01); *G06T 2207/20084* (2013.01); *G06T 2207/20221* (2013.01); *G06T 2207/30048* (2013.01); *G06T 2207/30061* (2013.01); *G06T 2210/41* (2013.01); *G06V 2201/03* (2022.01)

(58) Field of Classification Search
CPC ....... A61B 8/52; A61B 8/0833; A61B 8/0883; A61B 8/463; A61B 8/4263; A61B 2034/2065
See application file for complete search history.

(56) References Cited

U.S. PATENT DOCUMENTS

| | | | |
|---|---|---|---|
| 2012/0165673 | A1 | 6/2012 | Park |
| 2013/0345563 | A1* | 12/2013 | Stuebe ................. A61B 8/5223 |
| | | | 600/440 |
| 2015/0018684 | A1* | 1/2015 | Abe ..................... A61B 8/0883 |
| | | | 600/443 |
| 2015/0327841 | A1 | 11/2015 | Banjanin et al. |
| 2016/0143628 | A1 | 5/2016 | Kikuchi et al. |
| 2017/0105701 | A1* | 4/2017 | Pelissier ................ A61B 8/565 |

* cited by examiner

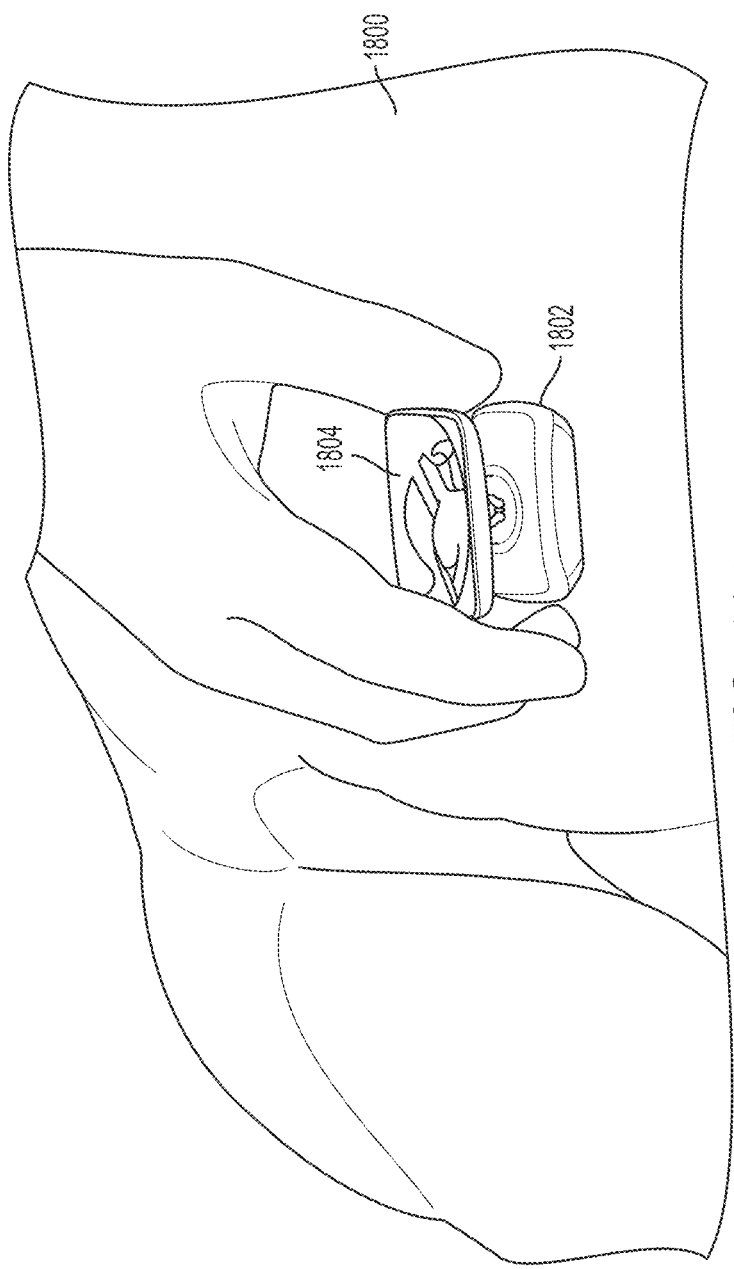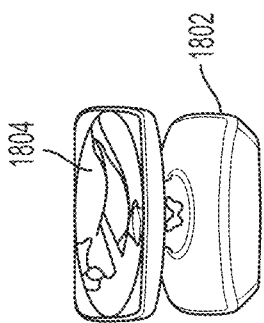

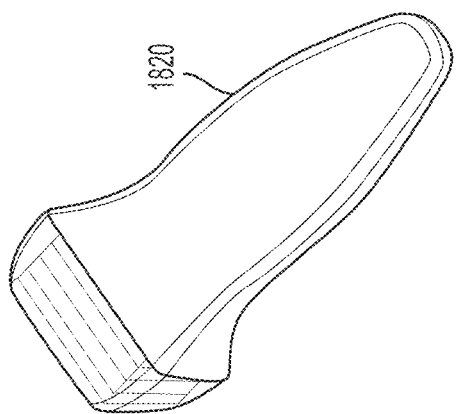

AUTOMATED IMAGE ANALYSIS FOR DIAGNOSING A MEDICAL CONDITION

CROSS-REFERENCE TO RELATED APPLICATIONS

This application is a continuation application of U.S. patent application Ser. No. 15/626,954, filed on Jun. 19, 2017 and claims the benefit under 35 U.S.C. § 119(e) of each of the following U.S. Provisional Applications: U.S. Provisional Application Ser. No. 62/352,382, titled "AUTOMATIC ACQUISITION ASSISTANCE AND REAL-TIME MEASUREMENT FOR ULTRASOUND IMAGING USING DEEP LEARNING" filed on Jun. 20, 2016, U.S. Provisional Application Ser. No. 62/384,187, titled "METHOD AND APPARATUS TO PROVIDE AUGMENTED REALITY GUIDED ULTRASOUND DETECTION" filed on Sep. 6, 2016, U.S. Provisional Application Ser. No. 62/384,144, titled "CLINICAL DIAGNOSTIC AND THERAPEUTIC DECISION SUPPORT USING PATIENT IMAGING DATA" filed on Sep. 6, 2016, U.S. Provisional Application Ser. No. 62/434,980, titled "INTEGRATING STATISTICAL PRIOR KNOWLEDGE INTO CONVOLUTIONAL NEURAL NETWORKS" filed on Dec. 15, 2016, U.S. Provisional Application Ser. No. 62/445,195, titled "METHOD AND APPARATUS TO PROVIDE AUGMENTED REALITY GUIDED ULTRASOUND DETECTION" filed on Jan. 11, 2017, U.S. Provisional Application Ser. No. 62/453,696, titled "METHOD AND APPARATUS TO PROVIDE AUGMENTED REALITY GUIDED ULTRASOUND DETECTION" filed on Feb. 2, 2017, and U.S. Provisional Application Ser. No. 62/463,094, titled "TECHNIQUES FOR LANDMARK LOCALIZATION" filed on Feb. 24, 2017. The disclosure of each and every identified application is incorporated herein by reference in its entirety.

FIELD

Generally, the aspects of the technology described herein relate to ultrasound systems. Some aspects relate to techniques for guiding an operator to use an ultrasound device.

BACKGROUND

Conventional ultrasound systems are large, complex, and expensive systems that are typically used in large medical facilities (such as a hospital) and are operated by medical professionals that are experienced with these systems, such as ultrasound technicians. Ultrasound technicians typically undergo years of hands-on training to learn how to properly use the ultrasound imaging system. For example, an ultrasound technician may learn how to appropriately position an ultrasound device on a subject to capture an ultrasound image in various anatomical views. Further, an ultrasound technician may learn how to read captured ultrasound images to infer medical information about the patient.

SUMMARY

Ultrasound examinations often include the acquisition of ultrasound images that contain a view of a particular anatomical structure (e.g., an organ) of a subject. Acquisition of these ultrasound images typically requires considerable skill. For example, an ultrasound technician operating an ultrasound device may need to know where the anatomical structure to be imaged is located on the subject and further how to properly position the ultrasound device on the subject to capture a medically relevant ultrasound image of the anatomical structure. Holding the ultrasound device a few inches too high or too low on the subject may make the difference between capturing a medically relevant ultrasound image and capturing a medically irrelevant ultrasound image. As a result, non-expert operators of an ultrasound device may have considerable trouble capturing medically relevant ultrasound images of a subject. Common mistakes by these non-expert operators include: capturing ultrasound images of the incorrect anatomical structure and capturing foreshortened (or truncated) ultrasound images of the correct anatomical structure.

Accordingly, the disclosure provides techniques to guide an operator of an ultrasound device to capture medically relevant ultrasound images. In some embodiments, these techniques may be embodied in a software application (hereinafter "App") that may be installed on a computing device (e.g., a mobile smartphone, a tablet, a laptop, a smart watch, virtual reality (VR) headsets, augmented reality (AR) headsets, smart wearable devices, etc.). The App may provide real-time guidance to the operator regarding how to properly position the ultrasound device on the subject to capture a medically relevant ultrasound image. For example, the operator may place the ultrasound device on the subject and receive feedback from the App regarding how to move the ultrasound device on the subject. The feedback may be a sequence of instructions each including a particular direction to move the ultrasound device (e.g., up, down, left, right, rotate clockwise, or rotate counter-clockwise). Thereby, the operator may follow these instructions to easily capture a medically relevant ultrasound image.

In some embodiments, the App may leverage state-of-the-art machine learning technology, such as deep learning. In these embodiments, the App may employ a trained model, such as a trained neural network, that is configured to generate instructions to provide to the operator. In this examples, the trained model may receive an ultrasound image captured by the ultrasound device being used by the operator and provide, as an output, an instruction to provide the operator. The model may be trained using a database of annotated ultrasound images. The annotations for each of the ultrasound images may comprise, for example, an indication of whether the ultrasound image was a medically relevant ultrasound image (e.g., an ultrasound image of a target anatomical plane) or a medically irrelevant ultrasound image (e.g., an ultrasound image captured by an improperly positioned ultrasound device). If the ultrasound image is medically irrelevant, the annotation may further include an indication of the error associated with the positioning of the ultrasound device that caused the captured ultrasound image to be medically irrelevant (e.g., too high, too low, too clockwise, too counter-clockwise, too far left, too far right). Thereby, the trained model may recognize these medically irrelevant images and generate an instruction regarding how the operator should reposition the ultrasound device to capture a medically relevant ultrasound image.

In some embodiments, an apparatus comprising a computing device comprising at least one processor is provided. The at least one processor is configured to: obtain an ultrasound image of a subject captured by an ultrasound device; determine, using an automated image processing technique, whether the ultrasound image contains a target anatomical view; responsive to a determination that the ultrasound image does not contain the target anatomical view, provide at least one instruction to an operator of the ultrasound device indicating how to reposition the ultrasound device in furtherance of capturing an ultrasound image of the subject that contains the target anatomical view; and responsive to a determination that the ultrasound image contains the target anatomical view, provide an indication to the operator that the ultrasound device is properly positioned.

In some embodiments, the apparatus further comprises a display coupled to the computing device and configured to display the at least one instruction to the operator. In some embodiments, the display is integrated with the computing device.

In some embodiments, the computing device is configured to determine whether the ultrasound image contains the target anatomical view at least in part by analyzing the ultrasound image using a deep learning technique. In some embodiments, the computing device is configured to determine whether the ultrasound image contains the target anatomical view at least in part by providing the ultrasound image as an input to a multi-layer neural network. In some embodiments, the computing device is configured to determine whether the ultrasound image contains the target anatomical view at least in part by using the multi-layer neural network to obtain an output that is indicative of an anatomical view contained in the ultrasound image. In some embodiments, the computing device is configured to determine whether the ultrasound image contains the target anatomical view at least in part by analyzing the ultrasound image using a multi-layer neural network comprising at least one layer selected from the group consisting of: a pooling layer, a rectified linear units (ReLU) layer, a convolution layer, a dense layer, a pad layer, a concatenate layer, and an upscale layer.

In some embodiments, the computing device is configured to determine whether the ultrasound image contains the target anatomical view at least in part by: identifying an anatomical view contained in the ultrasound image using the automated image processing technique; and determining whether the anatomical view contained in the ultrasound image matches the target anatomical view. In some embodiments, the computing device is configured to, responsive to a determination that the anatomical view contained in the ultrasound image does not match the target anatomical view, generate the at least one instruction using the anatomical view contained in the ultrasound image.

In some embodiments, the computing device is configured to provide the at least one instruction at least in part by providing an instruction to move the ultrasound device in a translational direction and/or a rotational direction. In some embodiments, the computing device is configured to provide the at least one instruction to the operator at least in part by providing the at least one instruction to the subject.

In some embodiments, a method is provided that comprises using at least one computing device comprising at least one processor to perform: obtaining an ultrasound image of a subject captured by an ultrasound device; determining, using an automated image processing technique, whether the ultrasound image contains a target anatomical view; responsive to determining that the ultrasound image does not contain the target anatomical view, providing at least one instruction to an operator of the ultrasound device indicating how to reposition the ultrasound device in furtherance of capturing an ultrasound image of the subject that contains the target anatomical view; and responsive to determining that the ultrasound image contains the target anatomical view, providing an indication to the operator that the ultrasound device is properly positioned.

In some embodiments, determining whether the ultrasound image contains the target anatomical view comprises analyzing the ultrasound image using a deep learning technique. In some embodiments, determining whether the ultrasound image contains the target anatomical view comprises providing the ultrasound image as an input to a multi-layer neural network. In some embodiments, determining whether the ultrasound image contains the target anatomical view comprises using the multi-layer neural network to obtain an output that is indicative of an anatomical view contained in the ultrasound image. In some embodiments, determining whether the ultrasound image contains the target anatomical view comprises analyzing the ultrasound image using a multi-layer neural network comprising at least one layer selected from the group consisting of: a pooling layer, a rectified linear units (ReLU) layer, a convolution layer, a dense layer, a pad layer, a concatenate layer, and an upscale layer.

In some embodiments, determining whether the ultrasound image contains the target anatomical view comprises: identifying an anatomical view contained in the ultrasound image using the automated image processing technique; and determining whether the anatomical view contained in the ultrasound image matches the target anatomical view.

In some embodiments, the method further comprises, responsive to determining that the anatomical view contained in the ultrasound image does not match the target anatomical view, generating the at least one instruction using the anatomical view contained in the ultrasound image.

In some embodiments, providing the at least one instruction comprises providing an instruction to move the ultrasound device in a translational direction and/or a rotational direction. In some embodiments, providing the at least one instruction to the operator comprises providing the at least one instruction to the subject.

In some embodiments, a system is provided that comprises an ultrasound device configured to capture an ultrasound image of a subject; and a computing device communicatively coupled to the ultrasound device. The computing device is configured to: obtain the ultrasound image of the subject captured by the ultrasound device; determine, using an automated image processing technique, whether the ultrasound image contains a target anatomical view; responsive to a determination that the ultrasound image does not contain the target anatomical view, provide at least one instruction to an operator of the ultrasound device indicating how to reposition the ultrasound device to capture an ultrasound image of the subject that contains the target anatomical view; and responsive to a determination that the ultrasound image contains the target anatomical view, provide an indication to the operator that the ultrasound device is properly positioned.

In some embodiments, the ultrasound device comprises a plurality of ultrasonic transducers. In some embodiments, the plurality of ultrasonic transducers comprises an ultrasonic transducer selected from the group consisting of: a capacitive micromachined ultrasonic transducer (CMUT), a CMOS ultrasonic transducer (CUT), and a piezoelectric micromachined ultrasonic transducer (PMUT).

In some embodiments, the computing device is a mobile smartphone or a tablet. In some embodiments, the computing device is configured to determine whether the ultrasound image contains the target anatomical view at least in part by analyzing the ultrasound image using a deep learning technique. In some embodiments, the computing device is configured to determine whether the ultrasound image contains the target anatomical view at least in part by providing the ultrasound image as an input to a multi-layer neural network. In some embodiments, the computing device is configured to determine whether the ultrasound image contains the target anatomical view at least in part by using the multi-layer convolutional neural network to obtain an output that is indicative of an anatomical view contained in the ultrasound image.

In some embodiments, the computing device is configured to determine whether the ultrasound image contains the target anatomical at least in part by: identifying an anatomical view contained in the ultrasound image using the automated image processing technique; and determining whether the anatomical view contained in the ultrasound image matches the target anatomical view. In some embodiments, the computing device is configured to generate the at least one instruction using the anatomical view contained in the ultrasound image responsive to a determination that the anatomical view contained in the ultrasound image does not match the target anatomical view.

In some embodiments, at least one non-transitory computer-readable storage medium storing processor-executable instructions is provided. The processor-executable instructions, when executed by at least one processor, cause the at least one processor to: obtain an ultrasound image of a subject captured by an ultrasound device; determine, using an automated image processing technique, whether the ultrasound image contains a target anatomical view; responsive to a determination that the ultrasound image does not contain the target anatomical view, provide at least one instruction to an operator of the ultrasound device indicating how to reposition the ultrasound device in furtherance of capturing an ultrasound image of the subject that contains the target anatomical view; and responsive to a determination that the ultrasound image contains the target anatomical view, provide an indication to the operator that the ultrasound device is properly positioned.

In some embodiments, an ultrasound guidance apparatus comprising at least one processor is provided. The at least one processor is configured to guide capture of an ultrasound image containing a target anatomical view of a subject based on analysis of another ultrasound image.

In some embodiments, the at least one processor is configured to guide capture of the ultrasound image at least in part by generating a guidance plan for how to guide an operator of an ultrasound device to capture the ultrasound image containing the target anatomical view. In some embodiments, the at least one processor is configured to guide capture of the ultrasound image at least in part by providing at least one instruction to the operator based on the generated guidance plan. In some embodiments, the apparatus further comprises a display coupled to the at least one processor and configured to display the at least one instruction to the operator. In some embodiments, the display and the at least one processor are integrated into a computing device. In some embodiments, the at least one processor is configured to guide capture of the ultrasound image at least in part by identifying an anatomical view contained in the other ultrasound image using a deep learning technique. In some embodiments, the at least one processor is configured to guide capture of the ultrasound image at least in part by identifying, using the identified anatomical view, a direction in which to move the ultrasound device. In some embodiments, the at least one processor is configured to guide capture of the ultrasound image at least in part by determining whether the other ultrasound image contains an anatomical view of the subject within a target region of the subject. In some embodiments, the at least one processor is configured to provide the at least one instruction to the operator at least in part by providing an instruction to the operator to move the ultrasound device toward a position at which the ultrasound device can obtain images of views within the target region of the subject responsive to a determination that the anatomical view contained in the other ultrasound image is outside the target region. In some embodiments, the at least one processor is configured to provide the at least one instruction to the operator at least in part by providing an instruction to the operator to move the ultrasound device toward a position at which the ultrasound device can obtain an image of the target anatomical view responsive to a determination that the anatomical view contained in the other ultrasound image is within the target region.

In some embodiments, a system comprising an ultrasound device configured to capture an ultrasound image of a subject and at least one processor is provided. The at least one processor is configured to guide capture of another ultrasound image containing a target anatomical view of a subject based on analysis of the ultrasound image captured by the ultrasound device.

In some embodiments, the ultrasound device comprises an ultrasonic transducer selected from the group consisting of: a capacitive micromachined ultrasonic transducer (CMUT), a CMOS ultrasonic transducer (CUT), and a piezoelectric micromachined ultrasonic transducer (PMUT). In some embodiments, the at least one processor is integrated into a mobile smartphone or a tablet.

In some embodiments, the at least one processor is configured to guide capture at least in part by: determining whether the ultrasound image contains a target anatomical view; responsive to determining that the ultrasound image does not contain the target anatomical view, generating, using the ultrasound image, a guidance plan for how to guide an operator of the ultrasound device to capture an ultrasound image of the subject containing the target anatomical view; and providing at least one instruction to the operator based on the generated guidance plan. In some embodiments, the guidance plan comprises a sequence of instructions to guide the operator of the ultrasound device to move the ultrasound device to a target location. In some embodiments, each instruction in the sequence of instructions is an instruction to move the ultrasound device in a translational or rotational direction. In some embodiments, the at least one processor is configured to generate the guidance plan at least in part by determining whether the ultrasound image contains an anatomical view of the subject within a target region of the subject. In some embodiments, the at least one processor is configured to provide the at least one instruction to the operator at least in part by providing an instruction to the operator to move the ultrasound device toward a position at which the ultrasound device can obtain images of views within the target region of the subject responsive to a determination that the anatomical view contained in the ultrasound image is not within the target region. In some embodiments, the at least one processor is configured to provide the at least one instruction to the operator at least in part by providing an instruction to the operator to move the ultrasound device toward a position at which the ultrasound device can obtain an image of the target anatomical view responsive to a determination that the anatomical view contained in the ultrasound image is within the target region.

In some embodiments, a method is provided. The method comprises using at least one computing device comprising at least one processor to perform: obtaining an ultrasound image of a subject captured by an ultrasound device; determining whether the ultrasound image contains a target anatomical view; responsive to determining that the ultrasound image does not contain the target anatomical view: generating, using the ultrasound image, a guidance plan for how to guide an operator of the ultrasound device to capture an ultrasound image of the subject containing the target anatomical view; and providing at least one instruction to the operator based on the generated guidance plan.

In some embodiments, generating the guidance plan comprises identifying an anatomical view contained in the ultrasound image using an automated image processing technique. In some embodiments, generating the guidance plan comprises identifying, using the identified anatomical view, a direction in which to move the ultrasound device, and wherein providing the at least one instruction to the operator comprises providing an instruction to the operator to move the ultrasound device in the identified direction. In some embodiments, identifying the direction in which to move the ultrasound device comprises identifying a translational direction or a rotational direction in which to move the ultrasound device.

In some embodiments, generating the guidance plan comprises determining whether the ultrasound image contains an anatomical view of the subject within a target region of the subject. In some embodiments, determining whether the ultrasound image contains the anatomical view of the subject within the target region of the subject comprises determining whether the ultrasound image contains an anatomical view of at least part of the subject's torso. In some embodiments, the method further comprises responsive to a determination that the anatomical view contained in the ultrasound image is not within the target region, providing the at least one instruction to the operator at least in part by providing an instruction to the operator to move the ultrasound device toward a position at which the ultrasound device can obtain images of views within the target region of the subject. In some embodiments, providing the instruction to the operator to move the ultrasound device toward the position comprises providing to the operator a visual indication of where the target region is located. In some embodiments, the method further comprises responsive to a determination that the anatomical view contained in the ultrasound image is within the target region, providing the at least one instruction to the operator at least in part by providing an instruction to the operator to move the ultrasound device toward a position at which the ultrasound device can obtain an image of the target anatomical view. In some embodiments, providing the instruction to the operator to instruct the operator to move the ultrasound device toward the position comprises providing to the operator a visual indication of a direction in which to move the ultrasound device.

In some embodiments, at least one non-transitory computer-readable storage medium storing processor-executable instructions is provided. The processor-executable instructions, when executed by at least one processor, cause the at least one processor to: obtain an ultrasound image of a subject captured by an ultrasound device; determine whether the ultrasound image contains a target anatomical view; responsive to a determination that the ultrasound image does not contain the target anatomical view, generate, using the ultrasound image, a guidance plan for how to guide an operator of the ultrasound device to capture an ultrasound image of the subject containing the target anatomical view; and provide at least one instruction to the operator based on the generated guidance plan.

In some embodiments, an ultrasound guidance apparatus is provided that comprises at least one processor configured to: obtain an image of an ultrasound device being used by an operator; and generate, using the obtained image of the ultrasound device, an augmented reality interface to guide the operator to capture an ultrasound image containing a target anatomical view.

In some embodiments, the apparatus further comprises a display coupled to the at least one processor and configured to display the augmented reality interface to the operator. In some embodiments, the display and the at least one processor are integrated into a computing device.

In some embodiments, the at least one processor is configured to generate the augmented reality interface at least in part by overlaying at least one instruction indicating how the operator is to reposition the ultrasound device onto the image of the ultrasound device to form a composite image. In some embodiments, the at least one processor is configured to generate the augmented reality interface at least in part by identifying a pose of the ultrasound device in the image of the ultrasound device. In some embodiments, the at least one processor is configured to overlay the at least one instruction at least in part by overlaying the at least one instruction onto the image of the ultrasound device using the pose of the ultrasound device. In some embodiments, the at least one instruction comprises an arrow indicating a direction in which the operator is to move the ultrasound device.

In some embodiments, the at least one processor is configured to obtain an ultrasound image captured by the ultrasound device. In some embodiments, the at least one processor is configured to generate the augmented reality interface at least in part by identifying a location of the ultrasound device in the image of the ultrasound device. In some embodiments, the at least one processor is configured to generate the augmented reality interface at least in part by overlaying the ultrasound image onto the image of the ultrasound device using the location of the ultrasound device.

In some embodiments, a method is provided that comprises obtaining an image of an ultrasound device being used by an operator, the image being captured by an imaging device different from the ultrasound device; generating a composite image at least in part by overlaying, onto the image of the ultrasound device, at least one instruction indicating how the operator is to reposition the ultrasound device; and presenting the composite image to the operator.

In some embodiments, the method further comprises identifying a pose of the ultrasound device in the image of the ultrasound device. In some embodiments, the ultrasound device has a marker disposed thereon, and wherein obtaining the image of the ultrasound device comprises obtaining an image of the marker. In some embodiments, identifying the pose of the ultrasound device comprises identifying a location of the marker in the image of the ultrasound device.

In some embodiments, overlaying the at least one instruction onto the image of the ultrasound device is performed using the pose of the ultrasound device. In some embodiments, overlaying the at least one instruction onto the image of the ultrasound device comprises overlaying an arrow onto at least part of the ultrasound device in the image of the ultrasound device, the arrow indicating a direction in which the operator is to move the ultrasound device.

In some embodiments, the method further comprises obtaining an ultrasound image captured by the ultrasound device. In some embodiments, generating the composite image comprises overlaying the ultrasound image captured by the ultrasound device onto the image of the ultrasound device. In some embodiments, the method further comprises identifying a location of the ultrasound device in the image of the ultrasound device. In some embodiments, overlaying the ultrasound image onto the image of the ultrasound device is performed using the location of the ultrasound device.

In some embodiments, a system is provided that comprises an imaging device different from an ultrasound device being used by an operator; a display; and at least one processor. The at least one processor is configured to: obtain an image of the ultrasound device being used by the operator captured by the imaging device; generate a composite image at least in part by overlaying, onto the image of the ultrasound device, at least one instruction indicating how the operator is to reposition the ultrasound device; and cause the display to present the composite image to the operator.

In some embodiments, the system further comprises a mobile smartphone or tablet comprising the display and the at least one processor. In some embodiments, the imaging device comprises a camera. In some embodiments, the mobile smartphone or tablet comprises the camera.

In some embodiments, the at least one processor is configured to identify a pose of the ultrasound device in the image of the ultrasound device. In some embodiments, the ultrasound device comprises a marker disposed thereon, wherein the image of the ultrasound device comprises an image of the marker, and wherein the at least one processor is configured to identify the pose of the ultrasound device at least in part by identifying a location of the marker in the image of the ultrasound device. In some embodiments, the marker is selected from the group consisting of: a holographic marker, a dispersive marker, and an ArUco marker. In some embodiments, the at least one processor is configured to generate the composite image at least in part by overlaying the at least one instruction onto the image of the ultrasound device using the pose of the ultrasound device.

In some embodiments, the system further comprises the ultrasound device. In some embodiments, the at least one processor is configured to generate the composite image at least in part by overlaying the ultrasound image captured by the ultrasound device onto the image of the ultrasound device. In some embodiments, the at least one processor is configured to identify a location of the ultrasound device in the image of the ultrasound device and wherein the at least one processor is configured to overlay the ultrasound image onto the image of the ultrasound device using the location of the ultrasound device.

In some embodiments, at least one non-transitory computer-readable storage medium storing processor-executable instructions is provided. The processor-executable instructions, when executed by at least one processor, cause the at least one processor to: obtain an image of an ultrasound device being used by an operator, the image being captured by an imaging device different from the ultrasound device; generate a composite image at least in part by overlaying, onto the image of the ultrasound device, at least one instruction indicating how the operator is to reposition the ultrasound device; and cause the display to present the composite image to the operator.

In some embodiments, an apparatus comprising at least one processor is provided. The at least one processor is configured to obtain an ultrasound image of a subject captured by an ultrasound device and determine, using an automated image processing technique, whether the ultrasound image contains a target anatomical view.

In some embodiments, the at least one processor is configured to determine whether the ultrasound image contains the target anatomical view at least in part by analyzing the ultrasound image using a deep learning technique. In some embodiments, the at least one processor is configured to determine whether the ultrasound image contains the target anatomical view at least in part by providing the ultrasound image as an input to a multi-layer neural network. In some embodiments, the at least one processor is configured to determine whether the ultrasound image contains the target anatomical view at least in part by using the multi-layer neural network to obtain an output that is indicative of an anatomical view contained in the ultrasound image. In some embodiments, the at least one processor is configured to determine whether the ultrasound image contains the target anatomical view at least in part by analyzing the ultrasound image using a multi-layer neural network comprising at least one layer selected from the group consisting of: a pooling layer, a rectified linear units (ReLU) layer, a convolution layer, a dense layer, a pad layer, a concatenate layer, and an upscale layer.

In some embodiments, the at least one processor is configured to determine whether the ultrasound image contains the target anatomical view at least in part by: identifying an anatomical view contained in the ultrasound image using the automated image processing technique; and determining whether the anatomical view contained in the ultrasound image matches the target anatomical view. In some embodiments, the at least one processor is configured to, responsive to a determination that the anatomical view contained in the ultrasound image does not match the target anatomical view, generate at least one instruction indicating how to reposition the ultrasound device in furtherance of capturing an ultrasound image of the subject that contains the target anatomical view using the anatomical view contained in the ultrasound image.

In some embodiments, the at least one processor is configured to: provide at least one instruction to an operator of the ultrasound device indicating how to reposition the ultrasound device in furtherance of capturing an ultrasound image of the subject that contains the target anatomical view responsive to a determination that the ultrasound image does not contain the target anatomical view; and provide an indication to the operator that the ultrasound device is properly positioned responsive to a determination that the ultrasound image contains the target anatomical view. In some embodiments, the apparatus further comprises a display coupled to the at least one processor and configured to display the at least one instruction to the operator. In some embodiments, the at least one processor is configured to provide the at least one instruction at least in part by providing an instruction to move the ultrasound device in a translational direction and/or a rotational direction. In some embodiments, the at least one processor is configured to provide the at least one instruction to the operator at least in part by providing the at least one instruction to the subject.

According to at least one aspect, a method is provided. The method comprises using at least one computing device comprising at least one processor to perform: obtaining an ultrasound image of a subject captured by an ultrasound device; determining, using an automated image processing technique, whether the ultrasound image contains a target anatomical view; responsive to determining that the ultrasound image does not contain the target anatomical view, providing at least one instruction to an operator of the ultrasound device indicating how to reposition the ultrasound device in furtherance of capturing an ultrasound image of the subject that contains the target anatomical view; and responsive to determining that the ultrasound image contains the target anatomical view, providing an indication to the operator that the ultrasound device is properly positioned.

In some embodiments, determining whether the ultrasound image contains the target anatomical view comprises analyzing the ultrasound image using a deep learning technique. In some embodiments, determining whether the ultrasound image contains the target anatomical view comprises providing the ultrasound image as an input to a multi-layer neural network. In some embodiments, determining whether the ultrasound image contains the target anatomical view comprises using the multi-layer neural network to obtain an output that is indicative of an anatomical view contained in the ultrasound image. In some embodiments, determining whether the ultrasound image contains the target anatomical view comprises analyzing the ultrasound image using a multi-layer neural network comprising at least one layer selected from the group consisting of: a pooling layer, a rectified linear units (ReLU) layer, a convolution layer, a dense layer, a pad layer, a concatenate layer, and an upscale layer.

In some embodiments, determining whether the ultrasound image contains the target anatomical view comprises: identifying an anatomical view contained in the ultrasound image using the automated image processing technique; and determining whether the anatomical view contained in the ultrasound image matches the target anatomical view. In some embodiments, the method further comprises responsive to determining that the anatomical view contained in the ultrasound image does not match the target anatomical view, generating the at least one instruction using the anatomical view contained in the ultrasound image.

In some embodiments, providing the at least one instruction comprises providing an instruction to move the ultrasound device in a translational direction and/or a rotational direction. In some embodiments, providing the at least one instruction to the operator comprises providing the at least one instruction to the subject.

In some embodiments, a system comprises an ultrasound device configured to capture an ultrasound image of a subject; and a computing device communicatively coupled to the ultrasound device is provided. The computing device is configured to: obtain the ultrasound image of the subject captured by the ultrasound device; determine, using an automated image processing technique, whether the ultrasound image contains a target anatomical view; responsive to a determination that the ultrasound image does not contain the target anatomical view, provide at least one instruction to an operator of the ultrasound device indicating how to reposition the ultrasound device to capture an ultrasound image of the subject that contains the target anatomical view; and responsive to a determination that the ultrasound image contains the target anatomical view, provide an indication to the operator that the ultrasound device is properly positioned.

In some embodiments, the ultrasound device comprises a plurality of ultrasonic transducers. In some embodiments, the plurality of ultrasonic transducers comprises an ultrasonic transducer selected from the group consisting of: a capacitive micromachined ultrasonic transducer (CMUT), a CMOS ultrasonic transducer (CUT), and a piezoelectric micromachined ultrasonic transducer (PMUT).

In some embodiments, the computing device is a mobile smartphone or a tablet. In some embodiments, the computing device is configured to determine whether the ultrasound image contains the target anatomical view at least in part by analyzing the ultrasound image using a deep learning technique. In some embodiments, the computing device is configured to determine whether the ultrasound image contains the target anatomical view at least in part by providing the ultrasound image as an input to a multi-layer neural network. In some embodiments, the computing device is configured to determine whether the ultrasound image contains the target anatomical view at least in part by using the multi-layer convolutional neural network to obtain an output that is indicative of an anatomical view contained in the ultrasound image.

In some embodiments, the computing device is configured to determine whether the ultrasound image contains the target anatomical at least in part by: identifying an anatomical view contained in the ultrasound image using the automated image processing technique; and determining whether the anatomical view contained in the ultrasound image matches the target anatomical view. In some embodiments, the computing device is configured to generate the at least one instruction using the anatomical view contained in the ultrasound image responsive to a determination that the anatomical view contained in the ultrasound image does not match the target anatomical view.

In some embodiments, at least one non-transitory computer-readable storage medium storing processor-executable instructions is provided. The processor-executable instructions, when executed by at least one processor, cause the at least one processor to: obtain an ultrasound image of a subject captured by an ultrasound device; determine, using an automated image processing technique, whether the ultrasound image contains a target anatomical view; responsive to a determination that the ultrasound image does not contain the target anatomical view, provide at least one instruction to an operator of the ultrasound device indicating how to reposition the ultrasound device in furtherance of capturing an ultrasound image of the subject that contains the target anatomical view; and responsive to a determination that the ultrasound image contains the target anatomical view, provide an indication to the operator that the ultrasound device is properly positioned.

In some embodiments, an apparatus is provided comprising at least one processor configured to: obtain an image of a marker on an ultrasound device being used by an operator; and generate an augmented reality interface configured to guide the operator using a pose of the ultrasound device identified based on the marker.

In some embodiments, the apparatus further comprises a display coupled to the at least one processor and configured to display the augmented reality interface to the operator. In some embodiments, the display and the at least one processor are integrated into a computing device. In some embodiments, the at least one processor is configured to generate the augmented reality interface at least in part by overlaying an instruction to the operator of the ultrasound device onto the image using the pose of the ultrasound device. In some embodiments, the at least one processor is configured to obtain an ultrasound image captured by the ultrasound device and generate the instruction to the operator using the ultrasound image. In some embodiments, the at least one processor is configured to identify the pose of the ultrasound device in the image at least in part by identifying a location of the marker in the image. In some embodiments, the at least one processor is configured to identify the pose of the ultrasound device at least in part by analyzing at least one characteristic of the marker in the image. In some embodiments, the at least one processor is configured to analyze the at least one characteristics of the marker in the image at least in part by identifying a color of the marker in the image. In some embodiments, the at least one processor is configured to identify the pose of the ultrasound device at least in part by identifying an orientation of the ultrasound device in the image using the color of the marker in the image. In some embodiments, the marker comprises a hologram or a monochrome pattern.

In some embodiments, a method is provided that comprises using at least one computing device comprising at least one processor to perform: obtaining an image of a marker on an ultrasound device being used by an operator, the image being captured by an imaging device different from an ultrasound device; automatically identifying a pose of the ultrasound device at least in part by analyzing at least one characteristic of the marker in the image; and providing an instruction to the operator of the ultrasound device using the identified pose of the ultrasound device.

In some embodiments, identifying the pose of the ultrasound device comprises identifying a location of the marker in the image. In some embodiments, identifying the pose of the ultrasound device comprises identifying a position of the ultrasound device in the image using the identified location of the marker in the image.

In some embodiments, identifying the pose of the ultrasound device comprises identifying a color of the marker in the image. In some embodiments, identifying the pose of the ultrasound device comprises identifying an orientation of the ultrasound device in the image using the color of the marker.

In some embodiments, obtaining the image of the marker comprises obtaining an image of a hologram or a monochrome pattern. In some embodiments, the method further comprises obtaining an ultrasound image captured by the ultrasound device; and generating the instruction using the ultrasound image. In some embodiments, the method further comprises overlaying the ultrasound image onto the image using the identified pose of the ultrasound device.

In some embodiments, providing the instruction comprises determining a location for the instruction to be overlaid onto the image using the pose of the ultrasound device.

In some embodiments, a system is provided that comprises an imaging device different from an ultrasound device being used by an operator; and at least one processor. The at least one processor is configured to obtain an image of a marker on the ultrasound device being used by the operator captured by the imaging device; automatically identify a pose of the ultrasound device at least in part by analyzing at least one characteristic of the marker in the obtained image; and provide an instruction to the operator of the ultrasound device using the identified pose of the ultrasound device.

In some embodiments, the system further comprises a mobile smartphone or tablet comprising the imaging device and the at least one processor. In some embodiments, the system further comprises the ultrasound device having the marker disposed thereon. In some embodiments, the marker is selected from the group consisting of: a holographic marker, a dispersive marker, and an ArUco marker.

In some embodiments, the system further comprises a display coupled to the at least one processor. In some embodiments, the at least one processor is configured to provide the instruction at least in part by causing the display to provide the instruction to the operator.

In some embodiments, the at least one processor is configured to identify the pose of the ultrasound device at least in part by identifying a location of the marker in the image. In some embodiments, the at least one processor is configured to identify the pose of the ultrasound device at least in part by identifying a position of the ultrasound device in the captured image using the identified location of the marker in the image.

In some embodiments, the at least one processor is configured to identify the pose of the ultrasound device at least in part by identifying a color of the marker in the image. In some embodiments, the at least one processor is configured to identify the pose of the ultrasound device at least in part by identifying an orientation of the ultrasound device in the captured image using the color of the marker.

In some embodiments, the at least one processor is configured to obtain an ultrasound image captured by the ultrasound device and generate the instruction using the ultrasound image.

In some embodiments, at least one non-transitory computer-readable storage medium storing processor-executable instructions is provided. The processor-executable instructions, when executed by at least one processor, cause the at least one processor to: obtain an image of a marker on an ultrasound device being used by an operator, the image being captured by an imaging device different from an ultrasound device; automatically identify a pose of the ultrasound device at least in part by analyzing at least one characteristic of the marker in the obtained image; and provide an instruction to the operator of the ultrasound device using the identified pose of the ultrasound device.

In some embodiments, an apparatus is provided that comprises at least one processor configured to: obtain an ultrasound image of a subject; and identify at least one medical parameter of the subject at least in part by analyzing the ultrasound image using a deep learning technique.

In some embodiments, the at least one processor is configured to identify the at least one medical parameter of the subject at least in part by identifying at least one anatomical feature of the subject in the ultrasound image using the deep learning technique. In some embodiments, the at least one processor is configured to identify the at least one anatomical feature of the subject at least in part by providing the ultrasound image as an input to a multi-layer neural network. In some embodiments, the at least one processor is configured to identify the at least one anatomical feature of the subject at least in part by using the multi-layer neural network to obtain an output that is indicative of the at least one anatomical feature of the subject in the ultrasound image. In some embodiments, the at least one processor is configured to identify the at least one anatomical feature of the subject at least in part by analyzing the ultrasound image using a multi-layer neural network comprising at least one layer selected from the group consisting of: a pooling layer, a rectified linear units (ReLU) layer, a convolution layer, a dense layer, a pad layer, a concatenate layer, and an upscale layer. In some embodiments, the at least one anatomical feature comprises an anatomical feature selected from the group consisting of: a heart ventricle, a heart valve, a heart septum, a heart papillary muscle, a heart atrium, an aorta, and a lung.

In some embodiments, the at least one medical parameter comprises a medical parameter selected from the group consisting of: an ejection fraction, a fractional shortening, a ventricle diameter, a ventricle volume, an end-diastolic volume, an end-systolic volume, a cardiac output, stroke volume, an intraventricular septum thickness, a ventricle wall thickness, and a pulse rate. In some embodiments, the at least one processor is configured to overlay the at least one medical parameter onto the ultrasound image of the subject to form a composite image. In some embodiments, the apparatus further comprises a display coupled to the at least one processor and configured to display the composite image to the operator. In some embodiments, the display and the at least one processor are integrated into a computing device.

In some embodiments, a method is provided that comprises using at least one computing device comprising at least one processor to perform: obtaining an ultrasound image of a subject captured by an ultrasound device; identifying at least one anatomical feature of the subject in the ultrasound image using an automated image processing technique; and identifying at least one medical parameter of the subject using the identified anatomical feature in the ultrasound image.

In some embodiments, identifying the at least one anatomical feature of the subject comprises analyzing the ultrasound image using a deep learning technique. In some embodiments, identifying the at least one anatomical feature of the subject comprises providing the ultrasound image as an input to a multi-layer neural network. In some embodiments, identifying the at least one anatomical feature of the subject comprises using the multi-layer neural network to obtain an output that is indicative of the at least one anatomical feature of the subject in the ultrasound image. In some embodiments, identifying the at least one anatomical feature of the subject comprises analyzing the ultrasound image using a multi-layer neural network comprising at least one layer selected from the group consisting of: a pooling layer, a rectified linear units (ReLU) layer, a convolution layer, a dense layer, a pad layer, a concatenate layer, and an upscale layer.

In some embodiments, identifying the at least one anatomical feature comprises identifying an anatomical feature selected from the group consisting of: a heart ventricle, a heart valve, a heart septum, a heart papillary muscle, a heart atrium, an aorta, and a lung. In some embodiments, identifying the at least one medical parameter comprises identifying a medical parameter selected from the group consisting of: an ejection fraction, a fractional shortening, a ventricle diameter, a ventricle volume, an end-diastolic volume, an end-systolic volume, a cardiac output, a stroke volume, an intraventricular septum thickness, a ventricle wall thickness, and a pulse rate. In some embodiments, obtaining the ultrasound image of the subject comprises obtaining a plurality of ultrasound images of the subject, and wherein identifying the at least one anatomical feature of the subject comprises identifying a ventricle in each of at least some of the plurality of ultrasound images using a multi-layer neural network. In some embodiments, identifying the at least one medical parameter comprises: estimating a ventricle diameter of the identified ventricles in each of the at least some of the plurality of images to obtain a plurality of ventricle diameters including a first ventricle diameter and a second ventricle diameter that is different from the first ventricle diameter; using the first ventricle diameter to estimate an end-diastolic volume; and using the second ventricle diameter to estimate an end-systolic volume. In some embodiments, identifying the at least one medical parameter comprises identifying an ejection fraction of the subject using the estimated end-diastolic volume and the estimated end-systolic volume.

In some embodiments, the method further comprises overlaying the at least one medical parameter onto the ultrasound image to form a composite image; and presenting the composite image.

In some embodiments, obtaining the ultrasound image comprises guiding an operator of the ultrasound device to capture the ultrasound image of the subject. In some embodiments, guiding the operator of the ultrasound device comprises providing the ultrasound image as an input to a first multi-layer neural network and wherein identifying the at least one anatomical feature of the subject comprises providing the ultrasound image as an input to a second multi-layer neural network that is different from the first multi-layer neural network.

In some embodiments, a system is provided that comprises an ultrasound device configured to capture an ultrasound image of a subject; and a computing device communicatively coupled to the ultrasound device. The computing device is configured to: obtain the ultrasound image captured by the ultrasound device; identify at least one anatomical feature of the subject in the ultrasound image using an automated image processing technique; and identify at least one medical parameter of the subject using the identified anatomical feature in the ultrasound image.

In some embodiments, the ultrasound device comprises a plurality of ultrasonic transducers. In some embodiments, the plurality of ultrasonic transducers comprises an ultrasonic transducer selected from the group consisting of: a capacitive micromachined ultrasonic transducer (CMUT), a CMOS ultrasonic transducer (CUT), and a piezoelectric micromachined ultrasonic transducer (PMUT).

In some embodiments, the computing device is a mobile smartphone or a tablet. In some embodiments, the computing device comprises a display, and wherein the computing device is configured to display an indication of the at least one medical parameter using the display.

In some embodiments, the ultrasound image contains an anatomical view selected from the group consisting of: a parasternal long axis (PLAX) anatomical view, a parasternal short-axis (PSAX) anatomical view, an apical four-chamber (A4C) anatomical view, and apical long axis (ALAX) anatomical view.

In some embodiments, at least one non-transitory computer-readable storage medium storing processor-executable instructions is provided. The process-executable instructions, when executed by at least one processor, cause the at least one processor to: obtain an ultrasound image of a subject captured by an ultrasound device; identify at least one anatomical feature of the subject in the ultrasound image using an automated image processing technique; and identify at least one medical parameter of the subject using the identified anatomical feature in the ultrasound image.

In some embodiments, an apparatus is provided that comprises at least one processor configured to: obtain an ultrasound image of a subject; and generate a diagnosis of a medical condition of the subject at least in part by analyzing the ultrasound image using a deep learning technique.

In some embodiments, the at least one processor is configured to generate the diagnosis at least in part by identifying at least one medical parameter of the subject using the ultrasound image. In some embodiments, the at least one medical parameter of the subject comprises a medical parameter selected from the group consisting of: an ejection fraction, a fractional shortening, a ventricle diameter, a ventricle volume, an end-diastolic volume, an end-systolic volume, a cardiac output, a stroke volume, an intraventricular septum thickness, a ventricle wall thickness, and a pulse rate.

In some embodiments, the at least one processor is configured to obtain the ultrasound image at least in part by guiding an operator of the ultrasound device to obtain the ultrasound image. In some embodiments, the at least one processor is configured to guide the operator of the ultrasound device at least in part by providing at least one instruction to the operator to reposition the ultrasound device. In some embodiments, the operator is the subject.

In some embodiments, the at least one processor is configured to receive medical information about the subject and identify a target anatomical view of the subject to image based on the received medical information about the subject. In some embodiments, the medical information about the subject comprises at least one member selected from the group consisting of: a heart rate, a blood pressure, a body surface area, an age, a weight, a height, and a medication being taken by the subject. In some embodiments, the at least one processor is configured to identify the target anatomical view of the subject to be imaged at least in part by identifying an anatomical view of a heart of the subject as the target anatomical view responsive to the medical information about the subject indicating that the subject has experienced paroxysmal nocturnal dyspnea.

In some embodiments, the at least one processor is configured to provide a recommended treatment for the subject to the operator of the ultrasound device using the diagnosed medical condition of the subject.

In some embodiments, a method is provided that comprises using at least one computing device comprising at least one processor to perform: receiving medical information about a subject; identifying, based on the received medical information, a target anatomical view of the subject to be imaged by an ultrasound device; obtaining an ultrasound image containing the target anatomical view captured by the ultrasound device; and generating a diagnosis of a medical condition of the subject using the ultrasound image containing the target anatomical view.

In some embodiments, obtaining the ultrasound image containing the target anatomical view comprises guiding an operator of the ultrasound device to obtain the ultrasound image containing the target anatomical view. In some embodiments, guiding the operator of the ultrasound device to obtain the ultrasound image containing the target anatomical view comprises providing at least one instruction to the operator to reposition the ultrasound device. In some embodiments, guiding the operator comprises guiding the subject.

In some embodiments, receiving the medical information about the subject comprises receiving medical information selected from the group consisting of: a heart rate, a blood pressure, a body surface area, an age, a weight, a height, and a medication being taken by the subject. In some embodiments, identifying the target anatomical view of the subject to be imaged comprises identifying an anatomical view of a heart of the subject as the target anatomical view responsive to the medical information about the subject indicating that the subject has experienced paroxysmal nocturnal dyspnea. In some embodiments, diagnosing the medical condition of the subject comprises identifying an ejection fraction of the subject using the ultrasound image containing the target anatomical view responsive to the medical information about the subject indicating that the subject has experienced paroxysmal nocturnal dyspnea.

In some embodiments, generating the diagnosis of a medical condition of the subject comprises identifying at least one medical parameter of the subject using the ultrasound image containing the target anatomical view. In some embodiments, identifying the at least one medical parameter of the subject comprises identifying a medical parameter selected from the group consisting of: an ejection fraction, a fractional shortening, a ventricle diameter, a ventricle volume, an end-diastolic volume, an end-systolic volume, a cardiac output, a stroke volume, an intraventricular septum thickness, a ventricle wall thickness, and a pulse rate.

In some embodiments, the method further comprises providing a recommended treatment for the subject to the operator of the ultrasound device using the diagnosed medical condition of the subject.

In some embodiments, the method further comprises reading a barcode disposed on the ultrasound device; and sending the barcode to another device to cause the other device to transmit the medical information about the subject to the at least one computing device. In some embodiments, the method further comprises sending the ultrasound image containing the target anatomical view to the other device to cause the other device to add the ultrasound image containing the target anatomical view to a medical file associated with the subject.

In some embodiments, a system is provided that comprises an ultrasound device configured to capture ultrasound images; and a computing device communicatively coupled to the ultrasound device. The computing device is configured to: receive medical information about a subject; identify, based on the received medical information, a target anatomical view of the subject to be imaged by the ultrasound device; obtain an ultrasound image containing the target anatomical view captured by the ultrasound device; and generate a diagnosis of a medical condition of the subject using the ultrasound image containing the target anatomical view.

In some embodiments, the ultrasound device comprises a plurality of ultrasonic transducers. In some embodiments, the plurality of ultrasonic transducers comprises an ultrasonic transducer selected from the group consisting of: a capacitive micromachined ultrasonic transducer (CMUT), a CMOS ultrasonic transducer (CUT), and a piezoelectric micromachined ultrasonic transducer (PMUT).

In some embodiments, the computing device is a mobile smartphone or a tablet. In some embodiments, the computing device is configured to identify the target anatomical view at least in part by identifying an anatomical view of a heart of the subject as the target anatomical view responsive to the medical information about the subject indicating that the subject has experienced paroxysmal nocturnal dyspnea. In some embodiments, the computing device is configured to identify an ejection fraction of the subject using the ultrasound image containing the target anatomical view responsive to the medical information about the subject indicating that the subject has experienced paroxysmal nocturnal dyspnea.

In some embodiments, the computing device is configured to generate the diagnosis of the medical condition of the subject at least in part by identifying at least one medical parameter of the subject using the ultrasound image containing the target anatomical view.

In some embodiments, at least one non-transitory computer-readable storage medium storing processor-executable instructions is provided. The processor-executable instructions, when executed by at least one processor, cause the at least one processor to: receive medical information about a subject; identify, based on the received medical information, a target anatomical view of the subject to be imaged by the ultrasound device; obtain an ultrasound image containing the target anatomical view captured by the ultrasound device; and generate a diagnosis of a medical condition of the subject using the ultrasound image containing the target anatomical view.

In some embodiments, a method for assessing position and orientation of an ultrasonic probe is provided. The method comprises (a) receiving, by a host device, ultrasound image data generated by the ultrasound probe positioned to image a desired feature of a subject, wherein the host device comprises a processor and memory; and (b) providing instructions to reposition the ultrasound probe in order to capture the desired feature, wherein the instructions are determined based at least on the desired feature.

In some embodiments, a method for real-time measurement prediction of ultrasound imaging is provided. The method comprises (a) receiving, by a host device, ultrasound image data generated by a ultrasound probe positioned to image a desired feature of a subject, wherein the host device comprises a processor and memory; and (b) comparing the received ultrasound image data with trained model data to predict, in real time, a landmark of the received ultrasound image data.

In some embodiments, a method to provide real-time ultrasound image acquisition assistance is provided. The method comprises (a) receiving an initial ultrasound image of a patient; (b) comparing attributes of the initial ultrasound image with criteria for a high quality ultrasound image; and (c) directing movement of an ultrasound probe to obtain a subsequent ultrasound image compliant with the criteria for the high quality ultrasound image.

In some embodiments, a method to provide real-time ultrasound image acquisition assistance is provided. The method comprises (a) receiving an acquisition intent instruction for a final ultrasound imagery; (b) receiving a first ultrasound image from an ultrasound probe, the first ultrasound image comprising a perspective of a subject; (c) identifying an infirmity of the first ultrasound image by comparing the first ultrasound image with the acquisition intent instruction; (d) identifying a remedial action to manipulate the ultrasound probe to remedy the infirmity of the first ultrasound imagery based on the acquisition intent instruction; and (e) displaying the identified remedial action to assist in acquisition of the final ultrasound image.

In some embodiments, a clinical diagnostic and therapeutic decision support system is provided. The system comprises a processor, the processor configured to: (a) acquire medical ultrasound image data of a subject to be diagnosed; (b) display a diagnosis determined based on at least the medical ultrasound image data; and (c) display a recommended treatment for the subject based on the diagnosis.

In some embodiments, a method of providing a clinical diagnostic and therapeutic decision is provided. The method comprises (a) acquiring, with a processor, medical ultrasound image data of a subject to be diagnosed; (b) displaying a diagnosis determined based on at least the medical ultrasound image data; and (c) displaying a recommended treatment for the subject, wherein the recommended treatment is determined based on the diagnosis.

In some embodiments, a method for training a convolutional neural network using statistical prior knowledge. The method comprises (a) receiving a training set comprising a plurality of medical images of a plurality of subjects and a training annotation associated with each of the plurality of medical images; (b) receiving statistical prior knowledge of the plurality of the medical images, wherein the statistical prior knowledge comprises statistics associated with variability of the medical images arising from naturally occurring structures of the plurality of subjects; and (c) training the convolutional neural network, using the training set, by incorporating the statistical prior knowledge.

In some embodiments, a method for performing segmentation of a medical image. The method comprises (a) providing the medical image of a feature of a subject; and (b) using a trained convolutional neural network to perform the image segmentation of the medical image, wherein the trained convolutional neural network is trained using statistical prior knowledge.

In some embodiments, a method for performing landmark localization of a medical image. The method comprises (a) providing the medical image of a feature of a subject; and (b) using a trained convolutional neural network to perform the landmark localization of the medical image, wherein the trained convolutional neural network is trained using statistical prior knowledge.

In some embodiments, a method is provided comprising (a) capturing an image of an ultrasound probe positioned relative to a patient; (b) capturing an in vivo ultrasound image of a portion of the patient's body; (c) identifying a location of the ultrasound probe in the captured image of the ultrasound probe, the location identified relative to the patient's body; (d) forming a composite image by overlaying the in vivo ultrasound image onto the image of the ultrasound probe to form a composite image at least in part by positioning the in vivo ultrasound image adjacent to the image of the ultrasound probe; and (e) displaying the composite image.

In some embodiments, the method further comprises displaying a plurality of composite images in real time. In some embodiments, the composite images are displayed on an augmented reality display. In some embodiments, the method further comprises providing instructions in real time based on the plurality of composite images, wherein the instructions guide a user of the ultrasound probe in acquisition of subsequent ultrasound images of the portion of the patient's body.

In some embodiments, a method is provided comprising (a) capturing an image of an ultrasound probe positioned relative to a patient; (b) capturing an in vivo ultrasound image of a portion of the patient's body; (c) identifying a location of the ultrasound probe in the captured image of the ultrasound probe, the location identified relative to the patient's body; (d) forming a composite image by overlaying the in vivo ultrasound image onto the image of the ultrasound probe to form a composite image at least in part by positioning the in vivo ultrasound image adjacent to the image of the ultrasound probe; and (e) displaying the composite image.

In some embodiments, a method of consumer-based use of an ultrasound device is provided. The method comprises (a) operating a portable ultrasound device by a user; (b) capturing an image of the portable ultrasound device using an image capture device; (c) adjusting a position and/or orientation of the ultrasound device in response to feedback provided by a processing device, wherein the feedback is generated by the processing device based at least on analysis of ultrasound data captured by the user using the portable ultrasound device; and (d) storing the ultrasound data captured by the user using the portable ultrasound device.

In some embodiments, operating the portable ultrasound device is performed in the user's home. In some embodiments, the feedback is provided in real time. In some embodiments, the feedback is provided using augmented reality. In some embodiments, the feedback comprises instructions regarding one or more of: (i) where the user should place the portable ultrasound device, (ii) how the user should reposition or orient the portable ultrasound device, (iii) how the user should linearly translate the portable ultrasound device, and (iv) how the user should act to facilitate capture of the ultrasound data. In some embodiments, the method further comprises displaying a diagnosis determined based on at least the medical image data. In some embodiments, the method further comprises displaying a recommended treatment for the subject, wherein the recommended treatment is determined based on the diagnosis.

In some embodiments, a method for training a convolutional neural network for landmark localization is provided. The method comprises (a) receiving a training set comprising a plurality of medical images of a plurality of subjects and a training annotation associated with each of the plurality of medical images; and (b) training the convolutional neural network to regress one or more landmark locations based at least on the training set.

In some embodiments, a method for performing landmark localization of a medical image of a subject is provided. The method comprises (a) providing the medical image of the subject; and (b) using a trained convolutional neural network to perform the landmark localization of the medical image of the subject, wherein the trained convolutional neural network is trained using a training set comprising a plurality of medical images of a plurality of subjects and a training annotation associated with each of the plurality of medical images.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

FIGS. 18A-18B show an exemplary handheld device comprising an ultrasound device and a display according to some embodiments of the disclosure;

FIG. 18F shows an exemplary handheld device comprising an ultrasound device according to some embodiments of the disclosure.

DETAILED DESCRIPTION

Figure 1:
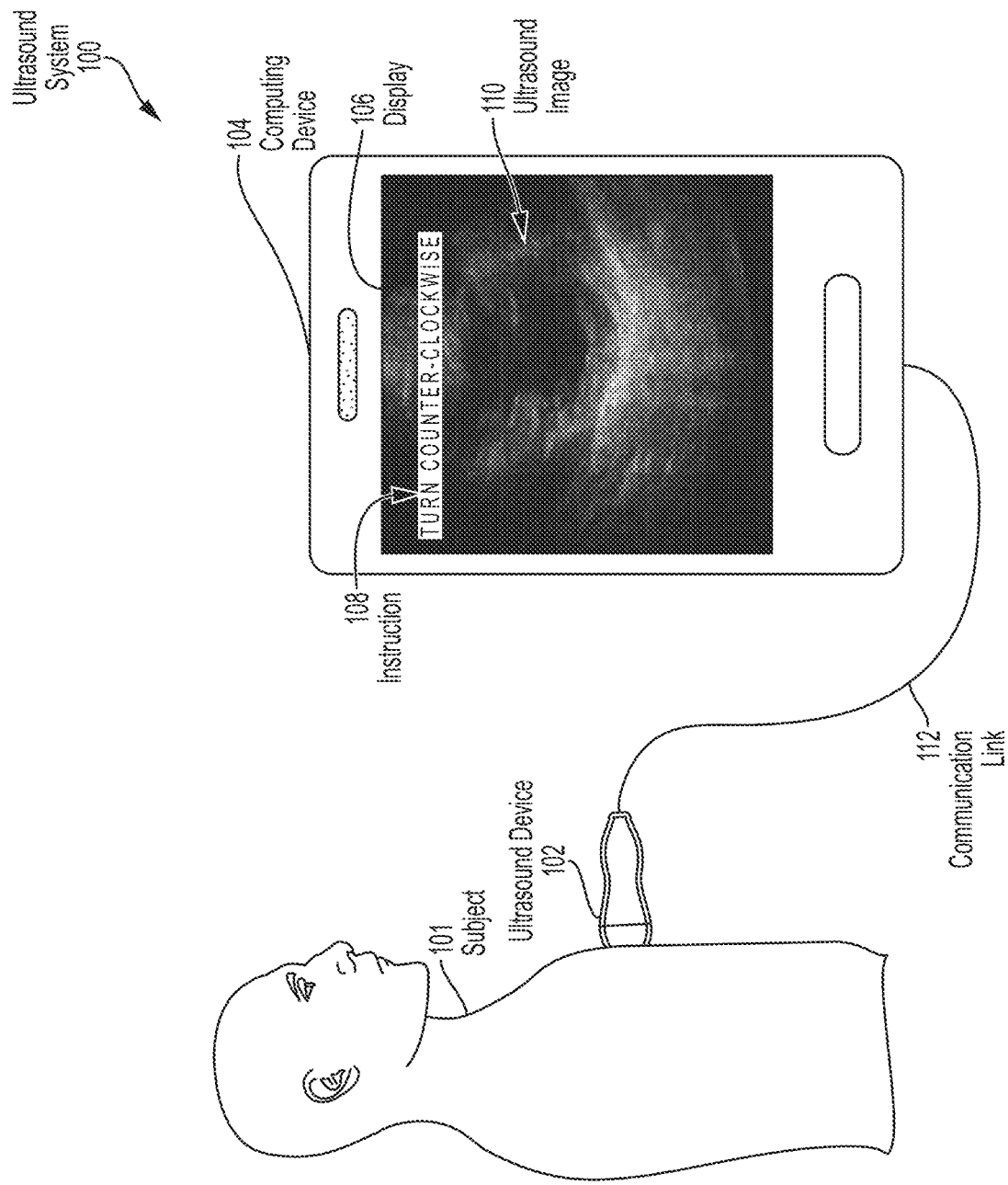
FIG. 1 shows an exemplary ultrasound system according to some embodiments of the disclosure.

Conventional ultrasound systems are large, complex, and expensive systems that are typically only purchased by large medical facilities with significant financial resources. Recently, cheaper and less complex ultrasound imaging devices have been introduced. Such imaging devices may include ultrasonic transducers monolithically integrated onto a single semiconductor die to form a monolithic ultrasound device. Aspects of such ultrasound-on-a chip devices are described in U.S. patent application Ser. No. 15/415,434 titled "UNIVERSAL ULTRASOUND DEVICE AND RELATED APPARATUS AND METHODS," filed on Jan. 25, 2017 (and assigned to the assignee of the instant application), which is incorporated by reference herein in its entirety. The reduced cost and increased portability of these new ultrasound devices may make them significantly more accessible to the general public than conventional ultrasound devices.

The inventors have recognized and appreciated that although the reduced cost and increased portability of ultrasound imaging devices makes them more accessible to the general populace, people who could make use of such devices have little to no training for how to use them. For example, a small clinic without a trained ultrasound technician on staff may purchase an ultrasound device to help diagnose patients. In this example, a nurse at the small clinic may be familiar with ultrasound technology and human physiology, but may know neither which anatomical views of a patient need to be imaged in order to identify medically-relevant information about the patient nor how to obtain such anatomical views using the ultrasound device. In another example, an ultrasound device may be issued to a patient by a physician for at-home use to monitor the patient's heart. In all likelihood, the patient understands neither human physiology nor how to image his or her own heart with the ultrasound device.

Accordingly, the inventors have developed assistive ultrasound imaging technology for guiding an operator of an ultrasound device to properly use the ultrasound device. This technology enables operators, having little or no experience operating ultrasound devices, to capture medically relevant ultrasound images and may further assist the operators in interpreting the contents of the obtained images. For example, some of the techniques disclosed herein may be used to: (1) identify a particular anatomical view of a subject to image with an ultrasound device; (2) guide an operator of the ultrasound device to capture an ultrasound image of the subject that contains the particular anatomical view; and (3) analyze the captured ultrasound image to identify medical information about the subject.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

A. Instructing an Operator of an Ultrasound Device how to Position the Device

The disclosure provides techniques for instructing an operator of an ultrasound device how to position the ultrasound device on a subject to capture a medically relevant ultrasound image. Capturing an ultrasound image of a subject that contains a particular anatomical view may be challenging for novice ultrasound device operators. The operator (e.g., a nurse, a technician or a lay person) needs to know not only where to initially position the ultrasound device on the subject (e.g., a patient), but also how to adjust the position of the device on the subject to capture an ultrasound image containing the target anatomical view. In cases where the subject is also the operator, it may be even more challenging for the operator to identify the appropriate view as the operator may not have a clear view of the ultrasound device. Accordingly, certain disclosed embodiments relate to new techniques for guiding the operator to capture an ultrasound image that contains the target anatomical view. The guidance may be provided via a software application (hereinafter "App") installed on a computing device of the operator (such as: a mobile device, a smartphone or smart-device, tablet, etc.). For example, the operator may install the App on a computing device and connect the computing device to an ultrasound device (e.g., using a wireless connection such as BLUETOOTH or a wired connection such as a Lightning cable). The operator may then position the ultrasound device on the subject and the software application (via the computing device) may provide feedback to the operator indicating whether the operator should reposition the ultrasound device and how he/she should proceed to do so. Following the instructions allows a novice operator to capture medically-relevant ultrasound images containing the target anatomical view.

In some embodiments, the instructions provided to the operator may be generated at least in part by using state-of-the-art image processing technology such as deep learning. For example, the computing device may analyze a captured ultrasound image using deep learning techniques to determine whether the ultrasound image contains the target anatomical view. If the ultrasound image contains the target anatomical view, the computing device may provide a confirmation to the operator that the ultrasound device is properly positioned on the subject and/or atomically start recording ultrasound images. Otherwise, the computing device may instruct the operator how to reposition the ultrasound device (e.g., "MOVE UP," "MOVE LEFT," "MOVE RIGHT," "ROTATE CLOCKWISE," "ROTATE COUNTER-CLOCKWISE," or "MOVE DOWN") to capture an ultrasound image that contains the target anatomical view.

The deep learning techniques described herein may be implemented in hardware, software or a combination of hardware and software. In one embodiment, a deep learning technique is implemented in an App executable on a smart device accessible to the operator. The App may, for example, leverage a display integrated into the smart device to display a user interface screen to the operator. In another embodiment, the App may be executed on a cloud and communicated to the operator through the smart device. In yet another embodiment, the App may be executed on the ultrasound device itself and the instructions may be communicated to the user either through the ultrasound device itself or a smart device associated with the ultrasound device. Thus, it should be noted that the execution of the App may be at a local or a remote device without departing from the disclosed principles.

In some embodiments, techniques for providing instructions to an operator of an ultrasound device regarding how to reposition the ultrasound device to capture an ultrasound image containing a target anatomical view of a subject may be embodied as a method that is performed by, for example, a computing device that is communicatively coupled to an ultrasound device. The computing device may be a mobile smartphone, a tablet, a laptop, a workstation, or any other suitable computing device. The ultrasound device may be configured to transmit acoustic waves into a subject using ultrasonic transducers, detect the reflected acoustic waves, and use them to generate ultrasound data. Example ultrasonic transducers include capacitive micromachined ultrasonic transducers (CMUTs), CMOS ultrasonic transducers (CUTs), and piezoelectric micromachined ultrasonic transducers (PMUTs). The ultrasonic transducers may be monolithically integrated with a semiconductor substrate of the ultrasound device. The ultrasound device may be implemented as, for example, a handheld device or as a patch that is configured to adhere to the subject.

In some embodiments, an exemplary method may include obtaining an ultrasound image of a subject captured using the ultrasound device. For example, the ultrasound device may generate ultrasound sound data and transmit (via a wired or wireless communication link) the ultrasound data to the computing device. The computing device may, in turn, generate the ultrasound image using the received ultrasound data. The method may further include determining whether the ultrasound image contains a target anatomical view using an automated image processing technique. For example, the ultrasound image may be analyzed using the automated image processing technique to identify the anatomical view contained in the ultrasound image. The identified anatomical view may be compared with the target anatomical view to determine whether the identified anatomical view matches the target anatomical view. If the identified anatomical view matches the target anatomical view, then a determination is made that the ultrasound image does contain the target anatomical view. Otherwise, a determination is made that the ultrasound image does not contain the target anatomical view.

It should be appreciated that any of a variety of automated image processing techniques may be employed to determine whether an ultrasound image contains the target anatomical view. Example automated image processing techniques include machine learning techniques such as deep learning techniques. In some embodiments, a convolutional neural network may be employed to determine whether an ultrasound image contains the target anatomical view. For example, the convolutional neural network may be trained with a set of ultrasound images labeled with the particular anatomical view depicted in the ultrasound image. In this example, an ultrasound image may be provided as an input to the trained convolutional neural network and an indication of the particular anatomical view contained in the input ultrasound image may be provided as an output.

In another example, the convolutional neural network may be trained with a set of ultrasound images labeled with either one or more instructions regarding how to move the ultrasound device to capture an ultrasound image containing the target anatomical view or an indication that the ultrasound image contains the target anatomical view. In this example, an ultrasound image may be provided as an input to a trained convolutional neural network and an indication that the ultrasound image contains the target anatomical view or an instruction to provide the operator may be provided as an output. The convolutional neural network may be implemented using a plurality of layers in any suitable combination. Example layers that may be employed in the convolutional neural network include: pooling layers, rectified linear units (ReLU) layers, convolutional layers, dense layers, pad layers, concatenate layers, and/or upscale layers. Examples of specific neural network architectures are provided herein in the Example Deep Learning Techniques section.

In some embodiments, the method may further include providing at least one instruction (or one set of instructions) to an operator of the ultrasound device indicating how to reposition the ultrasound device in furtherance of capturing an ultrasound image of the subject that contains the target anatomical view when a determination is made that the ultrasound image does not contain the target anatomical view. The instruction may be provided to the operator in any of a variety of ways. For example, the instruction may be displayed to the operator using a display (e.g., a display integrated into the computing device, such as the operator's mobile device) or audibly provided to the operator using a speaker (e.g., a speaker integrated into the computing device). Example instructions include "TURN CLOCKWISE," "TURN COUNTER-CLOCKWISE," "MOVE UP," "MOVE DOWN," "MOVE LEFT," and "MOVE RIGHT."

In some embodiments, the method may further include providing an indication to the operator that the ultrasound device is properly positioned when a determination is made that the ultrasound image contains the target anatomical view. The indication to the operator that the ultrasound device is properly positioned may take any of a variety of forms. For example, a symbol may be displayed to the operator such as a checkmark. Alternatively (or additionally), a message may be displayed and/or audibly played to the operator such as "POSITIONING COMPLETE."

The instructions can be computed based on the current position of the ultrasound device with respect to the subject's body. The instructions may be pre-recorded and determined by comparing the current positioning of the ultrasound device relative to one or more prior positions of the ultrasound device which yielded the target ultrasound image.

B. Determining how to Guide an Operator of an Ultrasound Device to Capture a Medically Relevant Ultrasound Image The disclosure provides techniques for guiding an operator of an ultrasound device to capture a medically relevant ultrasound image of a subject. Teaching an individual how to perform a new task, such as how to use an ultrasound device, is a challenging endeavor. The individual may become frustrated if they are provided instructions that are too complex or confusing. Accordingly, certain disclosed embodiments relate to new techniques for providing clear and concise instructions to guide the operator of an ultrasound device to capture an ultrasound image containing a target anatomical view. In some embodiments, the operator may position the ultrasound device on the subject and a computing device (such as a mobile smartphone or a tablet) may generate a guidance plan for how to guide the operator to move the ultrasound device from an initial position on the subject to a target position on the subject. The guidance plan may comprise a series of simple instructions or steps (e.g., "MOVE UP," "MOVE DOWN," "MOVE LEFT," or "MOVE RIGHT") to guide the operator from the initial position to the target position.

The guidance plan may optionally avoid using more complex instructions that may confuse the operator such as instructing the operator to move the ultrasound device diagonally. Once the guidance plan has been generated, instructions from the guidance plan may be provided in a serial fashion to the operator to avoid overloading the operator with information. Thereby, the operator may easily follow the sequence of simple instructions to capture an ultrasound image containing the target anatomical view.

In one embodiment, the guidance plan may be devised by comparing the current ultrasound image with the target ultrasound image and by determining how the positioning of the ultrasound device with respect to the subject should be changed to approach the target ultrasound image.

In some embodiments, techniques for determining how to guide an operator of an ultrasound device to capture an ultrasound image containing a target anatomical view may be embodied as a method that is performed by, for example, a computing device that is communicatively coupled to an ultrasound device. The method may include obtaining an ultrasound image of a subject captured using the ultrasound device. For example, the computing device may communicate with the ultrasound device to generate ultrasound data and send the generated ultrasound data to the computing device. The computing device may, in turn, use the received ultrasound data to generate the ultrasound image.

In some embodiments, the method may further include generating, using the ultrasound image, a guidance plan for how to guide the operator to capture an ultrasound image of the subject containing the target anatomical view when a determination is made that the ultrasound image does not contain the target anatomical view. The guidance plan may comprise, for example, a guide path along which an operator may be guided between an initial position of the ultrasound device on the subject and a target position of the ultrasound device on the subject where an ultrasound image that contains the target anatomical view may be captured. For example, the initial position of the ultrasound device may be identified using the ultrasound image and the target position of the ultrasound device may be identified using the target anatomical view. Once the initial and target positions of the ultrasound device have been identified, a guide path may be determined between the two positions.

In some embodiments, the guide path between the initial position of the ultrasound device and the target position of the ultrasound device may not be the most direct path between the two positions. For example, a longer guide path may be selected that forms an "L" over a direct diagonal line between the two points because the "L" shaped guide path may be easier to communicate to an operator. In some embodiments, the guide path may advantageously minimize travel of the ultrasound device over areas of the subject that contain hard tissue (e.g., bone). Capturing an ultrasound image of bone may yield a blank (or nearly blank) ultrasound image because the acoustic waves emitted by an ultrasound device typically do not penetrate hard tissues. As a result, there may be little or no information contained in the ultrasound image that may be used by the computing device to determine a position of the ultrasound device on the subject. Minimizing travel over these hard tissues may advantageously allow the computing device to more easily track the progress of the ultrasound device as the operator moves the ultrasound device along the guide path by analyzing the captured ultrasound images.

The method may further include providing at least one instruction to the operator based on the determined guidance plan. For example, instructions may be generated that instruct the operator to move the ultrasound device along a determined guide path in the guidance plan. Alternatively (or additionally), the guidance plan may include a sequence of instructions to guide the operator of the ultrasound device to move the device and the instructions may be provided directly from the guidance plan. The instructions may be provided from the guidance plan in a serial fashion (e.g., one at a time).

It should be appreciated that the guidance plan may be updated (e.g., continuously updated) based on the actions actually taken by an operator. In some embodiments, the guidance plan may be updated when the action taken by an operator does not match the instruction provided to the operator. For example, the computing device may issue an instruction for the operator to move the ultrasound device left and the operator may have inadvertently moved the ultrasound device up. In this example, the computing device may generate a new guidance plan between the current position of the ultrasound device and the target position of the ultrasound device.

C. Creating an Augmented Reality Interface to Guide an Operator of an Ultrasound Device The disclosure provides techniques for creating an augmented reality interface that guides an operator of an ultrasound device. Providing written and/or spoken instructions may be challenging for an operator to understand. For example, conveying an instruction to move an ultrasound device in a particular direction (e.g., "MOVE LEFT") may be ambiguous because the point of reference used by the operator may be different. Thereby, the operator may move the ultrasound device in an incorrect direction while believing that they are properly following the instructions. Accordingly, certain disclosed embodiments relate to new techniques for providing instructions to an operator of an ultrasound device through an augmented reality interface. In the augmented reality interface, the instructions may be overlaid onto a view of the operator's real-world environment. For example, the augmented reality interface may include a view of the ultrasound device positioned on the subject and an arrow indicative of the particular direction that the ultrasound device should be moved. Thereby, an operator may easily re-position the ultrasound device by moving the ultrasound device on the subject in a direction consistent with the arrow in the augmented interface.

In some embodiments, techniques for providing an augmented reality interface to guide an operator to capture an ultrasound image containing a target anatomical view may be embodied as a method that is performed by, for example, a computing device having (or being in communication with) a non-acoustic imaging device such as an imaging device configured to detect light. The method may include capturing, using a non-acoustic imaging device, an image of the ultrasound device. For example, an image may be captured of the ultrasound device positioned on a subject.

In some embodiments, the method may further include generating a composite image at least in part by overlaying, onto the image of the ultrasound device, at least one instruction indicating how the operator is to reposition the ultrasound device. For example, a pose (e.g., position and/or orientation) of the ultrasound device in the captured image may be identified using an automated image processing technique (e.g., a deep learning technique) and the information regarding the pose of the ultrasound device may be used to overlay an instruction onto at least part of the ultrasound device in the captured image. Example instructions that may be overlaid onto the image of the ultrasound device include symbols (such as arrows) indicating a direction in which the operator is to move the device.

It should be appreciated that additional elements may be overlaid onto the image of the ultrasound device using the identified pose of the ultrasound device. For example, the ultrasound image captured using the ultrasound device may be overlaid onto the image of the ultrasound device in such a fashion to make the ultrasound image appear as though it is extending outward from the ultrasound device into the subject. Thereby, the operator may gain a better appreciation for the particular region of the subject that is being imaged given the current position of the ultrasound device on the subject.

In some embodiments, the method may further include presenting the composite image to the operator. For example, the computing device may include an integrated display and the composite image may be displayed to the operator using the display.

D. Tracking a Location of an Ultrasound Device Using a Marker on the Ultrasound Device The disclosure provides techniques for tracking a location of an ultrasound device using a marker disposed on the ultrasound device. As discussed above, providing instructions to an operator of an ultrasound device through an augmented reality interface may make the instructions clearer and easier to understand. The augmented reality interface may include a captured image of a real-world environment (e.g., captured by a camera on a mobile smartphone) and one or more instructions overlaid onto the captured image regarding how to move the ultrasound device. Such augmented reality interfaces may be even more intuitive when the instructions are positioned relative to real-world objects in a captured image. For example, an arrow that instructs the operator to move the ultrasound device left may be clearer to the operator when the arrow is positioned proximate the ultrasound device in the captured image. Accordingly, aspects of the technology described herein relate to new techniques for tracking an ultrasound device in a captured image such that instructions may be properly positioned in the augmented reality interface. The problem of identifying the location of the ultrasound device in a captured image may be eased by placing a distinct marker on the ultrasound device that is visible in the captured image. The marker may have, for example, a distinctive pattern, color, and/or image that may be readily identified using automated image processing techniques (such as deep learning techniques). Thereby, the position of the ultrasound device in the captured image may be identified by locating the marker in the captured image. Once the position of the ultrasound device in the captured image has been identified, an instruction may be overlaid onto the captured image at a position proximate the ultrasound device to form a more intuitive augmented reality interface.

In some embodiments, techniques for tracking a location of an ultrasound device in a captured image using a marker disposed on the ultrasound device may be embodied as a method that is performed by, for example, a computing device that is communicatively coupled to an ultrasound device. The location of the ultrasound device in a captured image may be tracked to, for example, properly position an instruction over the captured image so as to form an augmented reality interface. For example, the instruction may be positioned proximate the ultrasound device in the captured image. In some embodiments, these techniques may be embodied as a method that is performed by, for example, a computing device having (or in communication with) a non-acoustic imaging device such as an imaging device configured to detect light. The non-acoustic imaging device may be employed to capture an image of a marker on an ultrasound device. The marker may be constructed to have a distinctive pattern, color, and/or image that may be recognized. The marker may be implemented in any of a variety of ways. For example, the marker may be: a monochrome marker, a holographic marker, and/or a dispersive marker. Monochrome markers may comprise a monochrome pattern such as ArUco markers. Holographic markers may comprise a hologram that presents different images depending upon the particular angle from which the hologram is viewed. Dispersive markers may comprise a dispersive element that presents different colors depending upon the particular angle from which the dispersive element is viewed.

In some embodiments, the method may further include automatically identifying a pose of the ultrasound device at least in part by analyzing at least one characteristic of the marker in the captured image. For example, a location of the marker in the image may be identified to determine a position of the ultrasound device in the image. Additionally (or alternatively), one or more properties of the marker may be analyzed to determine an orientation of the ultrasound device in the image. For example, the marker may be a dispersive marker and the color of the marker may be analyzed to determine an orientation of the ultrasound device. In another example, the marker may be a holographic marker and the particular image presented by the marker may be analyzed to determine an orientation of the ultrasound device.

In some embodiments, the method may further include providing an instruction to an operator of the ultrasound device using the identified pose of the ultrasound device. For example, the instruction may comprise a symbol (e.g., an arrow) overlaid onto the captured image that is presented to the operator. In this example, the identified pose of the ultrasound device in the image may be employed to accurately position the symbol over at least part of the ultrasound device in the captured image.

E. Automatically Interpreting Captured Ultrasound Images

The disclosure provides techniques for automatically interpreting captured ultrasound images to identify medical parameters of a subject. Novice operators of an ultrasound device may not be able to interpret captured ultrasound images to glean medically relevant information about the subject. For example, a novice operator may not know how to calculate medical parameters of the subject from a captured ultrasound image (such as an ejection fraction of a heart of the subject). Accordingly, certain disclosed embodiments relate to new techniques for automatically analyzing a captured ultrasound image to identify such medical parameters of the subject. In some embodiments, the medical parameters may be identified using state of the art image processing technology such as deep learning. For example, deep learning techniques may be employed to identify the presence of particular organs (such as a heart or a lung) in the ultrasound image. Once the organs in ultrasound image have been identified, the characteristics of the organs (e.g., shape and/or size) may be analyzed to determine a medical parameter of the subject (such as an ejection fraction of a heart of the subject).

In some embodiments, techniques for identifying a medical parameter of a subject using a captured ultrasound image may be embodied as a method that is performed by, for example, a computing device that is communicatively coupled to an ultrasound device. The method may include obtaining an ultrasound image of a subject captured using an ultrasound device. For example, the computing device may communicate with the ultrasound device to generate ultrasound data and send the generated ultrasound data to the computing device. The computing device may, in turn, use the received ultrasound data to generate the ultrasound image.

In some embodiments, the method may further include identifying an anatomical feature of the subject in the ultrasound image using an automated image processing technique. Example anatomical features of the subject that may be identified include: a heart ventricle, a heart valve, a heart septum, a heart papillary muscle, a heart atrium, an aorta, and a lung. These anatomical features may be identified using any of a variety of automated image processing techniques such as deep learning techniques.

In some embodiments, the method may further include identifying a medical parameter of the subject using the identified anatomical feature in the ultrasound image. For example, an ultrasound image of a heart may be captured and the ventricle in the ultrasound image may be identified as an anatomical feature. In this example, one or more dimensions of the heart ventricle may be calculated using the portion of the ultrasound image identified as being a heart ventricle to identify medical parameters associated with the heart. Example medical parameters associated with the heart include: an ejection fraction, a fractional shortening, a ventricle diameter, a ventricle volume, an end-diastolic volume, an end-systolic volume, a cardiac output, a stroke volume, an intraventricular septum thickness, a ventricle wall thickness, and a pulse rate.

F. Automatically Generating a Diagnosis of a Medical Condition

The disclosure provides techniques for generating a diagnosis of a medical condition of a subject using a captured ultrasound image. Novice operators of an ultrasound device may be unaware of how to use an ultrasound device to diagnose a medical condition of the subject. For example, the operator may be unsure of which anatomical view of a subject to image to diagnose the medical condition. Further, the operator may be unsure of how to interpret a captured ultrasound image to diagnose the medical condition. Accordingly, certain disclosed embodiments relate to new techniques for assisting an operator of an ultrasound device to diagnose a medical condition of a subject. In some embodiments, these techniques may be employed in a diagnostic App that may be installed on a computing device (e.g., a smartphone) of a health care professional. The diagnostic App may walk the health care professional through the entire process of diagnosing a medical condition of the subject. For example, the diagnostic App may prompt the health care professional for medical information about the subject (e.g., age, weight, height, resting heart rate, blood pressure, body surface area, etc.) that may be employed to determine a particular anatomical view of the subject to image with an ultrasound device. Then, the diagnostic App may guide the health care professional to capture an ultrasound image of the anatomical view. The diagnostic App may employ the captured ultrasound image (or sequence of ultrasound images) and/or raw ultrasound data from the ultrasound device. It should be appreciated that other information (such as the medical information about the subject) may be employed in combination with the ultrasound image(s) and/or raw ultrasound data to diagnose the medical condition of the subject.

In some embodiments, techniques for diagnosing a medical condition of a subject using an ultrasound device may be embodied as a method that is performed by, for example, a computing device that is communicatively coupled to an ultrasound device. The method may include receiving medical information about a subject. Example medical information about a subject includes: heart rate, blood pressure, body surface area, age, weight, height, and medication being taken by the subject. The medical information may be received from an operator by, for example, posing one or more survey questions to the operator. Alternatively (or additionally), the medical information may be obtained from an external device such as an external server.

In some embodiments, the method may further include identifying a target anatomical view of the subject to be captured using an ultrasound device based on the received medical information. Example anatomical views that may be identified include: a parasternal long axis (PLAX) anatomical view, a parasternal short-axis (PSAX) anatomical view, an apical four-chamber (A4C) anatomical view, and an apical long axis (ALAX) anatomical view. In some embodiments, the medical information may be analyzed to determine whether the subject has any health problems associated with a particular organ that may be imaged, such as a heart or a lung. If the medical information indicated that the subject has such health problems, an anatomical view associated with the organ may be identified. For example, the medical information may include an indication that the subject has symptoms of congestive heart failure (such as recently experiencing paroxysmal nocturnal dyspnea). In this example, an anatomical view associated with the heart (such as the PLAX anatomical view) may be identified as the appropriate view to be captured.

In some embodiments, the method may further include obtaining an ultrasound image containing the target anatomical view of the subject. For example, the ultrasound image may be obtained from an electronic health record of the subject. Additionally (or alternatively), the operator may be guided to obtain the ultrasound image containing the target anatomical view. For example, the operator may be provided one or more instructions (e.g., a sequence of instruction) to reposition the ultrasound device on the subject such that the ultrasound device is properly positioned on the subject to capture the target anatomical view.

In some embodiments, the method may further include generating a diagnosis of a medical condition of the subject using the ultrasound image containing the target anatomical view. For example, one or more medical parameters (e.g., an ejection fraction) may be extracted from the ultrasound image (or sequence of ultrasound images) and employed to generate a diagnosis. It should be appreciated that additional information separate from the ultrasound image containing the target anatomical view may be employed to identify a diagnosis of a medical condition of the subject. For example, the medical information regarding the subject may be employed in combination with one or more medical parameters extracted from the ultrasound device to generate the diagnosis.

In some embodiments, the method may further include generating one or more recommended treatments for the subject. The recommended treatments may be generated based on diagnosed medical condition of the subject. For example, the subject may be diagnosed with a heart condition (e.g., congestive heart failure) and the recommended treatment may comprise a pharmaceutical drug employed to treat the heart condition (e.g., a beta blocker drug).

G. Further Description

FIG. 1 shows an example ultrasound system 100 that is configured to guide an operator of an ultrasound device 102 to obtain an ultrasound image of a target anatomical view of a subject 101. As shown, the ultrasound system 100 comprises an ultrasound device 102 that is communicatively coupled to the computing device 104 by a communication link 112. The computing device 104 may be configured to receive ultrasound data from the ultrasound device 102 and use the received ultrasound data to generate an ultrasound image 110. The computing device 104 may analyze the ultrasound image 110 to provide guidance to an operator of the ultrasound device 102 regarding how to reposition the ultrasound device 102 to capture an ultrasound image containing a target anatomical view. For example, the computing device 104 may analyze the ultrasound image 110 to determine whether the ultrasound image 110 contains a target anatomical view, such as a PLAX anatomical view. If the computing device 104 determines that the ultrasound image 110 contains the target anatomical view, the computing device 104 may provide an indication to the operator using a display 106 that the ultrasound device 102 is properly positioned. Otherwise, the computing device 104 may provide an instruction 108 using the display 106 to the operator regarding how to reposition the ultrasound device 102.

The ultrasound device 102 may be configured to generate ultrasound data. The ultrasound device 102 may be configured to generate ultrasound data by, for example, emitting acoustic waves into the subject 101 and detecting the reflected acoustic waves. The detected reflected acoustic wave may be analyzed to identify various properties of the tissues through which the acoustic wave traveled, such as a density of the tissue. The ultrasound device 102 may be implemented in any of variety of ways. For example, the ultrasound device 102 may be implemented as a handheld device (as shown in FIG. 1) or as a patch that is coupled to patient using, for example, an adhesive. Example ultrasound devices are described in detail below in the Example Ultrasound Devices section.

The ultrasound device 102 may transmit ultrasound data to the computing device 104 using the communication link 112. The communication link 112 may be a wired (or wireless) communication link. In some embodiments, the communication link 112 may be implemented as a cable such as a Universal Serial Bus (USB) cable or a Lightning cable. In these embodiments, the cable may also be used to transfer power from the computing device 104 to the ultrasound device 102. In other embodiments, the communication link 112 may be a wireless communication link such as a BLUETOOTH, WiFi, or ZIGBEE wireless communication link.

The computing device 104 may comprise one or more processing elements (such as a processor) to, for example, process ultrasound data received from the ultrasound device 102. Additionally, the computing device 104 may comprise one or more storage elements (such as a non-transitory computer readable medium) to, for example, store instructions that may be executed by the processing element(s) and/or store all or any portion of the ultrasound data received from the ultrasound device 102. It should be appreciated that the computing device 104 may be implemented in any of a variety of ways. For example, the computing device 104 may be implemented as a mobile device (e.g., a mobile smartphone, a tablet, or a laptop) with an integrated display 106 as shown in FIG. 1. In other examples, the computing device 104 may be implemented as a stationary device such as a desktop computer. Additional example implementations of the computing device are described below in the Example Ultrasound Systems section.

The computing device 104 may be configured to provide guidance to an operator of the ultrasound device 102 using the ultrasound data received from the ultrasound device 102. In some embodiments, the computing device 104 may generate the ultrasound image 110 using the received ultrasound data and analyze the ultrasound image 110 using an automated image processing technique to generate the instruction 108 regarding how the operator should re-position the ultrasound device 102 to capture an ultrasound image containing the target anatomical view. For example, the computing device 104 may identify the anatomical view contained in the ultrasound image 110 using a machine learning technique (such as a deep learning technique) and determine whether the anatomical view contained in the ultrasound image 110 matches the target anatomical view. If the identified anatomical view matches the target anatomical view, the computing device 104 may provide an indication that the ultrasound is properly positioned via the display 106. Otherwise, the computing device 104 may identify an instruction to provide the operator to reposition the ultrasound device 102 and provide the instruction via the display 106. In another example, the computing device 104 may generate the instruction 108 without performing the intermediate step of determining whether the ultrasound image 110 contains the target anatomical view. For example, the computing device 104 may use a machine learning technique (such as a deep learning technique) to directly map the ultrasound image 110 to an output to provide to the user such as an indication of proper positioning or an instruction to reposition the ultrasound device 102 (e.g., instruction 108).

Figure 2:
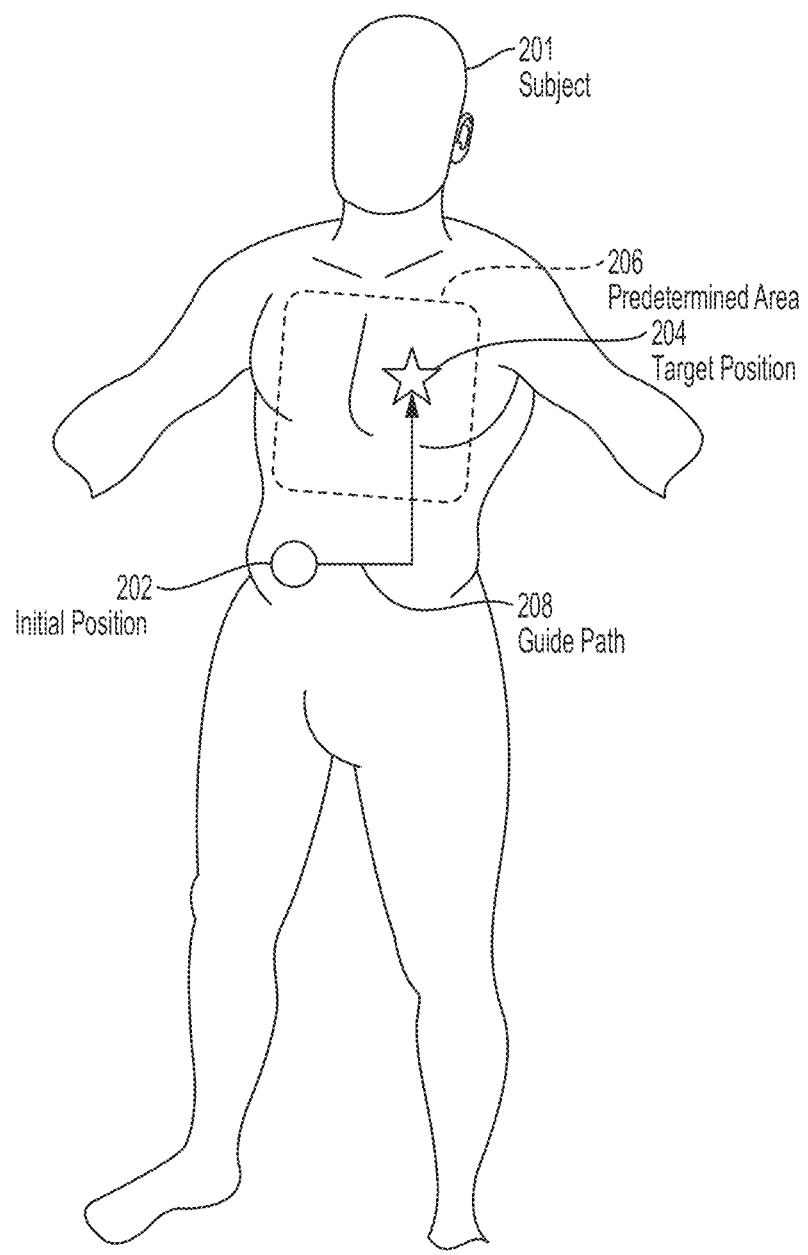
FIG. 2 shows an exemplary guide path along which to move the ultrasound device from an initial position on the subject to a target position on the subject according to some embodiments of the disclosure.

In some embodiments, the computing device 104 may be configured to generate the instruction 108 for the operator regarding how to position the ultrasound device 102 on the subject 101 using a guidance plan. The guidance plan may comprise a guide path indicative of how the operator should be guided to move the ultrasound device 102 from an initial position on the subject 101 to a target position on the subject 101 where an ultrasound image containing the target anatomical view may be captured. An example of such a guide path on a subject is shown in FIG. 2. As shown, the ultrasound device may be initially positioned on a subject 201 at an initial position 202 (on a lower torso of the subject 201) and the computing device may generate a guide path 208 between the initial position 202 and a target position 204. The guide path 208 may be employed by the computing device to generate a sequence of instructions to provide the operator. For example, the computing device may generate a first instruction to "MOVE RIGHT" and a second instruction to "MOVE UP" for the guide path 208. The generated instructions may also include an indication of the magnitude of the movement, such as "MOVE RIGHT 5 CENTIMETERS." The computing device may provide these instructions serially (e.g., one at a time) to avoid overloading the operator with information.

The computing device may identify the initial position 202 by analyzing the ultrasound data received from the ultrasound device using an automated image processing technique (e.g., a deep learning technique). For example, the computing device may provide an ultrasound image (generated using the ultrasound data) as an input to a neural network that is configured (e.g., trained) to provide as an output an indication of the anatomical view contained in the ultrasound image. Then, the computing device may map the identified anatomical view to a position on the subject 201. The mappings between anatomical views and positions on the subject 201 may be, for example, stored locally on the computing device.

The computing device may identify the target position 204 based on the target anatomical view. For example, the computing device may map the target anatomical view to a position on the subject 201. The mappings between target anatomical views and positions on the subject 201 may be, for example, stored locally on the computing device.

Once the initial position 202 and the target position 204 have been identified, the computing device may identify the guide path 208 that an operator should follow to move the ultrasound device from the initial position 202 to the target position 204. The computing device may generate the guide path 208 by, for example, identifying a shortest path between the initial position 202 and the target position 204 (e.g., a diagonal path). Alternatively, the computing device may generate the guide path 208 by identifying a shortest path between the initial position 202 and the target position 204 that satisfies one or more constraints. The one or more constraints may be selected to, for example, ease communication of instructions to the operator to move the ultrasound device along the guide path 208. For example, movement in particular directions (such as diagonal directions) may be more challenging to accurately communicate to an operator. Thereby, the computing device may identify a shortest path that omits diagonal movements as the guide path as shown by the "L" shaped guide path 208 in FIG. 2. Additionally (or alternatively), the guide path 208 may be selected to minimize traversal over hard tissue (e.g., bone) in the subject. Minimizing the travel over such hard tissues may advantageously allow the computing device to more readily track the movement of the ultrasound device along the guide path 208. For example, ultrasound images of bone may be blank (or nearly blank) because the acoustic waves emitted by an ultrasound device typically do not penetrate hard tissues. The computing device may be unable to analyze such ultrasound images to determine which anatomical view they belong to and, thereby, lose track of the position of the ultrasound device on the subject 201. Minimizing travel over these hard tissues may advantageously allow the computing device to more easily track the progress of the ultrasound device as the operator moves the ultrasound device along the guide path 208 by analyzing the captured ultrasound images.

The computing device may store the generated guide path 208 locally and use the guide path to generate a sequence of instructions to provide to the operator. For example, the computing device may use the guide path 208 to generate the sequence of instructions: (1) "MOVE LATERAL," (2) "MOVE UP," and (3) "TWIST CLOCKWISE." These instructions may be, in turn, provided to the operator in a serial fashion to guide the operator to move the ultrasound device from the initial position 202 to the target position 204.

As discussed above, novice operators of an ultrasound device may have little or no knowledge of human physiology. Thereby, the initial position 202 may be far away from the target position 204. For example, an operator may initially place the ultrasound device on a leg of the subject 201 when the target position 204 is on an upper torso of the subject 201. Providing a sequence of individual instructions to move the ultrasound device from the distant initial position 202 to the target position 204 may be a time-consuming process. Accordingly, the computing device may initially provide the operator a coarse instruction to move the ultrasound device to a general area of the subject 201 (such as an upper torso of the subject 201) and subsequently provide one or more fine instructions to move the ultrasound device in particular directions (such as "MOVE UP").

In some embodiments, the computing device may make the determination as to whether to issue a coarse instruction or a fine instruction based on a determination as to whether the ultrasound device is positioned on the subject within a predetermined area 206 on the subject 201. The predetermined area 206 may be an area on the subject 201 that includes the target position 204 and is easy for the operator to identify. For example, the target position 204 may be over a heart of the subject 201 and the predetermined area 206 may comprise an upper torso of the subject. The computing device may provide a fine instruction responsive to the position of the ultrasound device being within the predetermined area 206 and provide a coarse instruction responsive to the ultrasound device being outside of the predetermined area 206. For example, an operator may initially position the ultrasound device on a leg of the subject 201 and the computing device may provide a coarse instruction that instructs the operator to move the ultrasound device to an upper torso (e.g., the predetermined area 206) of the subject 201. Once the operator has positioned the ultrasound device on the upper torso of the subject 201 (and thereby within the predetermined area 206), the computing device may provide a fine instruction including an indication of a particular direction to move the ultrasound device towards the target position 204.

Providing coarse instructions may advantageously expedite the process of guiding the operator of the ultrasound device. For example, an operator may be unfamiliar with human physiology and initially place the ultrasound device on a leg of the subject 201 while the operator is attempting to capture an ultrasound image containing an anatomical view of a heart of the subject 201. In this example, the operator may be provided a coarse instruction including an indication of where to place the ultrasound device (e.g., on an upper torso of the subject) instead of providing a set of instructions for the operator to move the ultrasound device: (1) from the thigh to the lower torso and (2) from the lower torso to the upper torso.

Figure 3B:
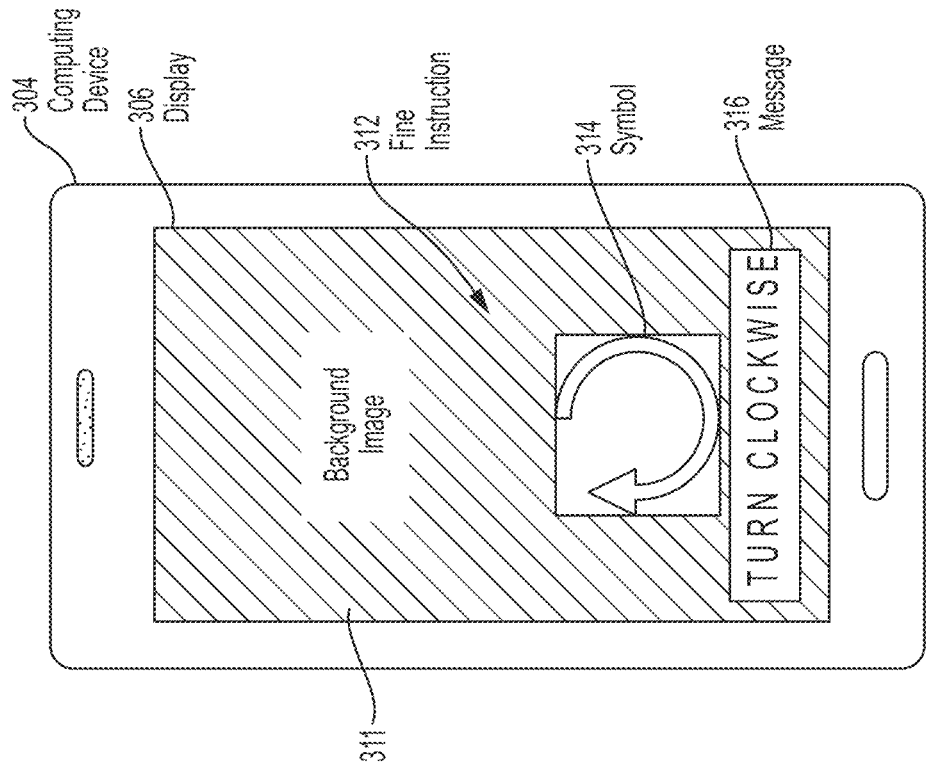
FIG. 3B shows an exemplary fine instruction to be provided to an operator according to some embodiments of the disclosure.
Figure 3A:
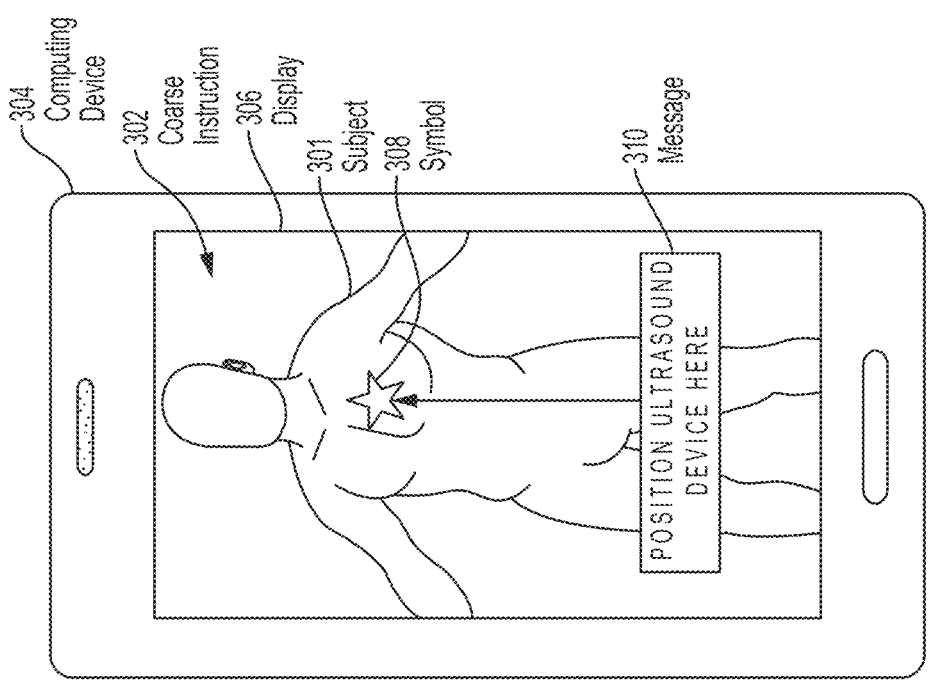
FIG. 3A shows an exemplary coarse instruction to be provided to an operator according to some embodiments of the disclosure.

FIG. 3A shows an example coarse instruction 302 that may be provided to an operator via a display 306 on a computing device 304. The coarse instruction 302 may be provided when the ultrasound device is positioned outside of a predetermined area on the subject. As shown, the coarse instruction 302 includes an indication of where the operator should position the ultrasound device on the subject to be within the predetermined area. In particular, the coarse instruction 302 comprises a symbol 308 (e.g., a star) showing where the predetermined region is located on a graphical image of the subject 301. The coarse instruction 302 also includes a message 310 with an arrow pointing to the symbol 308 instructing the operator to "POSITION ULTRASOUND DEVICE HERE" to communicate to the operator that the ultrasound device should be placed where the symbol 308 is located on the graphical image of the subject 301.

FIG. 3B shows an example fine instruction 312 that may be provided to an operator via the display 306 on the computing device 304. The fine instruction 312 may be provided when the ultrasound device is positioned within the predetermined area on the subject. As shown, the fine instruction 312 includes a symbol 314 indicating which direction the operator should move the ultrasound device. The symbol 314 may be animated in some implementations. For example, the symbol 314 (e.g., an arrow and/or model of the ultrasound device) may move in a direction in which the ultrasound device is to be moved. The fine instruction 312 may also comprise a message 316 that compliments the symbol 314 such as the message "TURN CLOCKWISE." The symbol 314 and/or the message 316 may be overlaid onto a background image 311. The background image 311 may be, for example, an ultrasound image generated using ultrasound data received from the ultrasound device.

Figure 3C:
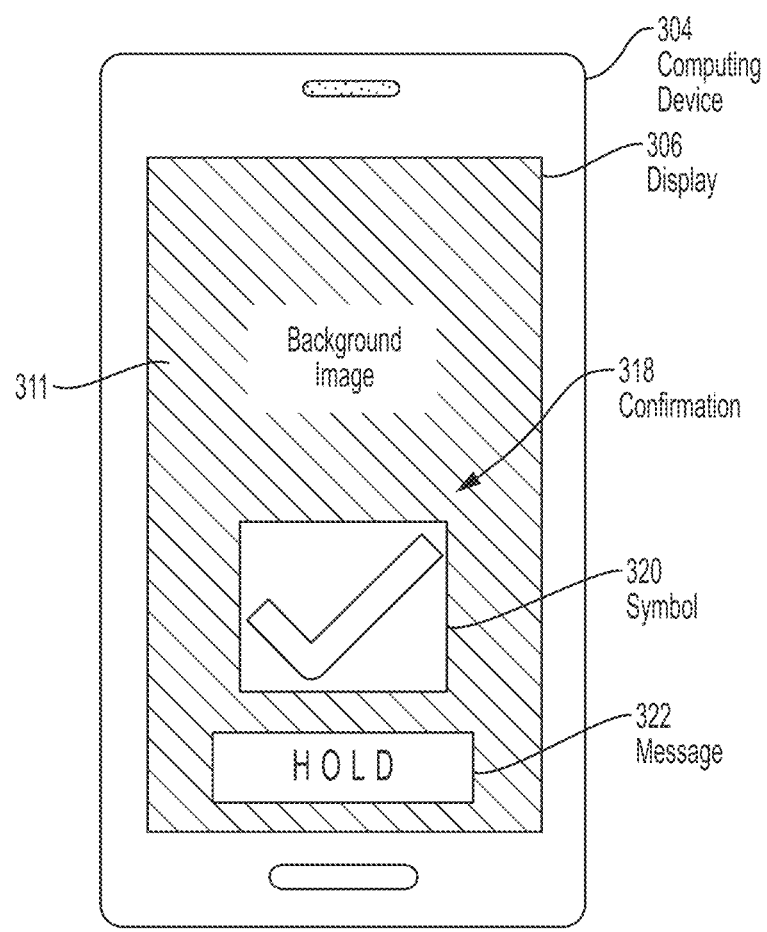
FIG. 3C shows an exemplary confirmation to be provided to an operator according to some embodiments of the disclosure.

FIG. 3C shows an example confirmation 318 that may be provided to an operator via the display 306 on the computing device 304. The confirmation 318 may be provided when the ultrasound device is properly positioned on the subject to capture an ultrasound image containing the target anatomical view. As shown, the confirmation 318 includes a symbol 320 (e.g., a checkmark) indicating that the ultrasound device is properly positioned. The confirmation 318 may also comprise a message 322 that compliments the symbol 320 such as the message "HOLD." The symbol 320 and/or the message 322 may be overlaid onto the background image 311. The background image 311 may be, for example, an ultrasound image generated using ultrasound data received from the ultrasound device.

Once the operator has successfully captured an ultrasound image that contains the target anatomical view, the computing device may be configured to analyze the captured ultrasound image. For example, the computing device may analyze the captured ultrasound image using an automated image processing technique to identify a medical parameter of the subject. Example medical parameters of the subject that may be obtained from the ultrasound image include: an ejection fraction, a fractional shortening, a ventricle diameter, a ventricle volume, an end-diastolic volume, an end-systolic volume, a cardiac output, a stroke volume, an intraventricular septum thickness, a ventricle wall thickness, and a pulse rate. The computing device may identify these medical parameters by, for example, identifying an anatomical feature in the ultrasound image (such as a heart ventricle, a heart valve, a heart septum, a heart papillary muscle, a heart atrium, an aorta, and a lung) and analyzing the identified anatomical feature. The computing device may identify the anatomical feature using an automated imaging processing technique (such as a deep learning technique). For example, the computing device may provide the captured ultrasound image to a neural network that is configured (e.g., trained) to provide as an output an indication of which pixels in the ultrasound image are associated with a particular anatomical feature. It should be appreciated that this neural network may be separate and distinct from any neural networks employed to guide the operator.

Figure 4:
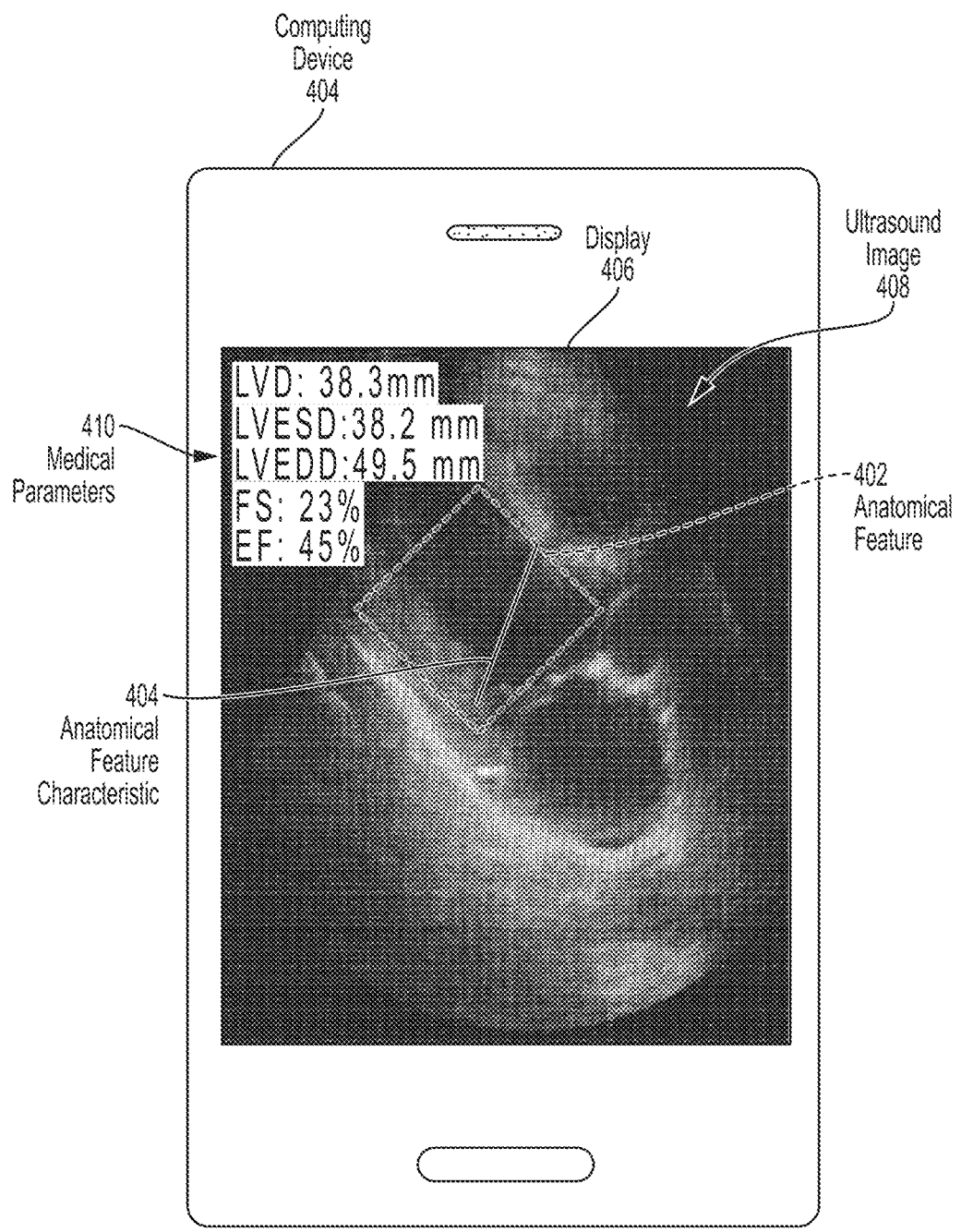
FIG. 4 shows exemplary medical parameters overlaid onto an ultrasound image according to some embodiments of the disclosure.

The generated medical parameters may be overlaid onto the captured ultrasound image as shown in FIG. 4. As shown, a computing device 404 may display (via an integrated display 406) an ultrasound image 408 and a set of medical parameters 410 overlaid onto the ultrasound image 408. The ultrasound image 408 may contain a PLAX view of a subject that includes a view of a heart of the subject. In the ultrasound image 408, the computing device may identify the left ventricle as an anatomical feature 402 and analyze the characteristics of the left ventricle (such as the left ventricle diameter shown as anatomical feature characteristic 404) to identify the medical parameters 410. The medical parameters 410 shown in FIG. 4 comprise: a left ventricle diameter (LVD) of 38.3 millimeters (mm), a left ventricle end-systolic diameter (LVESD) of 38.2 mm, a left ventricle end-diastolic diameter (LVEDD) of 49.5 mm, a fractional shortening (FS) of 23%, an ejection fraction (EF) of 45%.

It should be appreciated that the computing device may identify the medical parameters 410 using more than a single ultrasound image containing the target anatomical view. In some embodiments, a sequence of ultrasound images of the heart may be captured that span at least one complete heartbeat to generate the medical parameters. For example, the ultrasound images may be analyzed to determine which ultrasound image was captured at the end of the contraction of a heart ventricle (referred to as the end-systolic image) and which ultrasound image was captured just before the start of the contraction of a heart ventricle (referred to as the end-diastolic image). The end-systolic image may be identified by, for example, identifying the ultrasound image in the sequence that has a smallest ventricle volume (or diameter). Similarly, the end-diastolic image may be identified by, for example, identifying the ultrasound image in the sequence that has the largest ventricle volume (or diameter). The end-systolic image may be analyzed to determine one or more medical parameters that are measured at the end of the heart contraction such as an end-systolic diameter (ESD) and/or an end-systolic volume (ESV). Similarly, the end-diastolic image may be analyzed to determine one or more medical parameters that are measured just before the start of a heart contraction such as an end-diastolic diameter (EDD) and/or an end-diastolic volume (EDV). Some medical parameters may require analysis of both the end-systolic image and the end-diastolic image. For example, the identification of the EF may require (1) an EDV identified using the end-diastolic image and (2) an ESV identified using the end-systolic image as shown in Equation (1) below:

$$EF = \frac{EDV - ESV}{EDV} * 100 \qquad (1)$$

Similarly, the identification of the FS may require (1) an EDD identified using the end-diastolic image and (2) an ESD identified using the end-systolic image as shown in Equation (2) below:

$$FS = \frac{EDD - ESD}{EDD} * 100 \qquad (2)$$

In some embodiments, the computing device may change a color of the medical parameters 410 shown in the display 406 based on the value of the medical parameters. For example, the medical parameters 410 may be displayed in a first color (e.g., green) to indicate that the values are within a normal range, a second color (e.g., orange) to indicate that the values are in a borderline abnormal range, and a third color (e.g., red) to indicate that the values are in an abnormal range.

Example Augmented Reality Interfaces

Figure 5A:
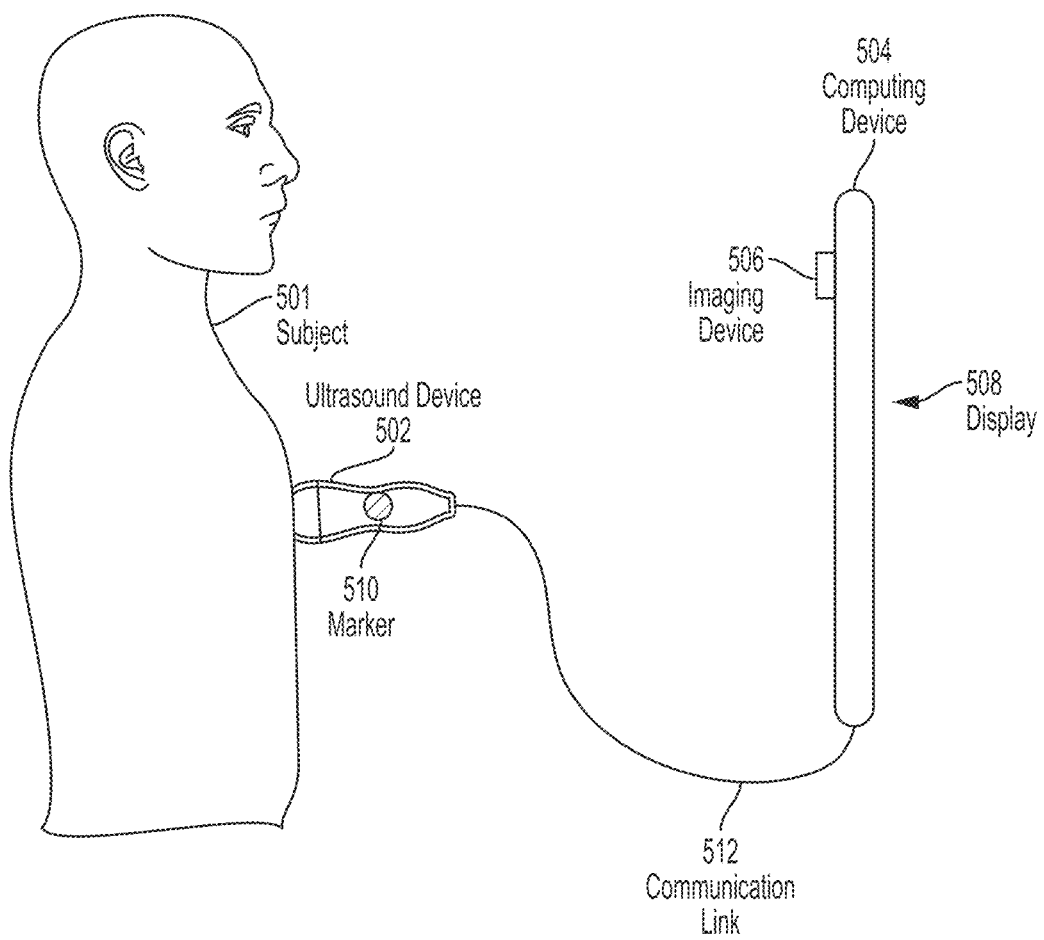
FIGS. 5A and 5B show an exemplary ultrasound system configured to provide an augmented reality interface to an operator according to some embodiments of the disclosure.

The inventors have recognized that providing instructions to an operator through an augmented reality interface may advantageously make the instructions easier to understand for the operator. FIG. 5A shows an example ultrasound system that is configured to provide the operator an augmented reality interface. As shown, the ultrasound system comprises an ultrasound device 502 communicatively coupled to a computing device 504 via a communication link 512. The ultrasound device 502, communication link 512, and/or computing device 504 may be similar to (or the same as) the ultrasound device 102, the communication link 112, and/or the computing device 104, respectively, described above with reference to FIG. 1. The ultrasound system further comprises a marker 510 disposed of the ultrasound device 502. The marker advantageously allow the computing device 504 to more easily track the location of the ultrasound device in non-acoustic images captured by an imaging device 506 (e.g., integrated into the computing device 504). The computing device 504 may use the tracked location of the ultrasound device in the non-acoustic images to overlay one or more elements (e.g., instructions) onto the non-acoustic images to form an augmented reality interface. Such an augmented reality interface may be displayed via a display 508 (e.g., integrated into the computing device 502 and disposed on an opposite side relative to the imaging device 506).

It should be appreciated that the computing device 504 does not need to be implemented as a handheld device. In some embodiments, the computing device 504 may be implemented as a wearable device with a mechanism to display instructions to an operator. For example, the computing device 504 may be implemented as a wearable headset and/or a pair of smart glasses (e.g., GOOGLE GLASS, APPLE AR glasses, and MICROSOFT HOLOLENS).

Figure 5B:
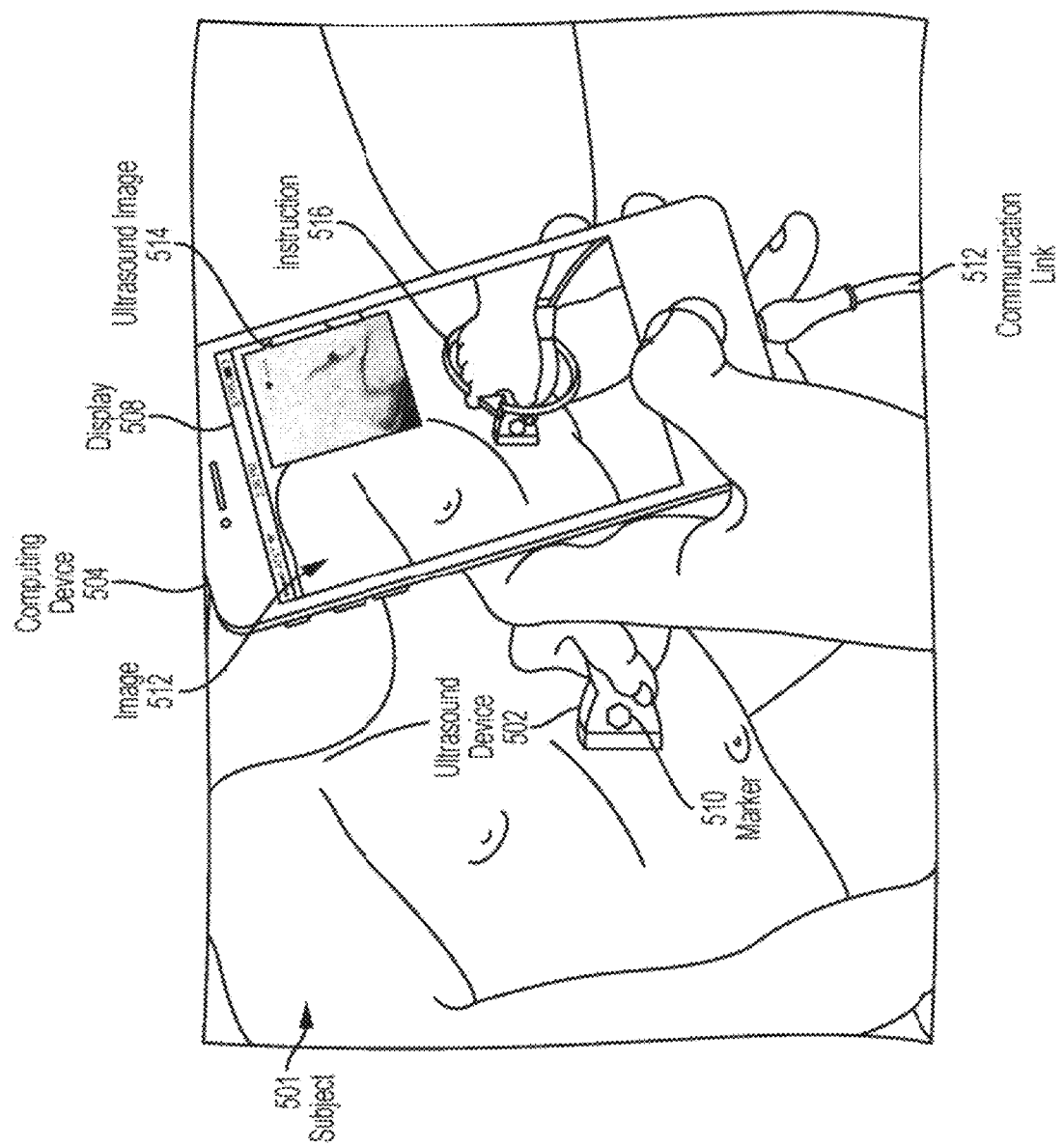

FIG. 5B shows another view of the ultrasound system from the perspective of an operator. As shown, the display 508 in the computing device 504 displays an augmented reality interface comprising a non-acoustic image 512 of the ultrasound device 502 being used on the subject 501 (e.g., captured by the imaging device 506) and one or more elements overlaid onto the image 512. For example, an instruction 516 indicative of a direction for the operator to move the ultrasound device 502, a symbol indicating a location of the target anatomical plane, and/or an ultrasound image 514 captured by the ultrasound device 502 may be overlaid onto the image 512. These elements may be implemented, for example, as: opaque elements (so as to obscure the portion of the image 512 under the element), transparent elements (so as to not obscure the portion of the image 512 under the element), pseudo colorized elements, and/or cutaway elements.

In some embodiments, the instruction 516 may be overlaid onto the image 512 such that at least a portion of the instruction 516 is overlaid onto the ultrasound device 502 in the image 512. The computing device 504 may, for example, use the marker 510 to identify a pose (e.g., a position and/or orientation) of the ultrasound device 502 in the image 512 and position the instruction 516 in the augmented reality interface using the identified pose. The marker 510 may be constructed to have one or more distinctive characteristics that may easily be recognized in the image 512. Example markers include: monochrome markers, holographic markers, and dispersive markers. Monochrome markers may comprise a monochrome pattern such as ArUco markers. Holographic markers may comprise a hologram that presents different images depending on the particular angle from which the hologram is viewed. Dispersive markers may comprise a dispersive element that presents different colors depending on the particular angle from which the dispersive element is viewed. The computing device 504 may identify the pose of the ultrasound device 502 in any of a variety of ways. In some embodiments, the computing device may identify a position of the ultrasound device 502 in the image 512 by identifying a location of the marker 510. The location of the marker 510 may be identified by searching for one or more distinct characteristics of the marker 510 in the image 512. Additionally (or alternatively), the computing device may identify an orientation of the ultrasound device 502 in the image 512 by analyzing one or more characteristics of the marker 512. For example, the marker 510 may be a dispersive marker and the computing device may identify an orientation of the ultrasound device 502 in the image 512 by identifying a color of the marker 510 in the image 512. In another example, the marker 510 may be a holographic marker and the computing device may identify an orientation of the ultrasound device 502 in the image 512 by identifying an image presented by the marker 510 in the image 512. In yet another example, the marker 510 may be a patterned monochrome marker and the computing device may identify an orientation of the ultrasound device 502 in the image 512 by identifying an orientation of the pattern on the marker 510 in the image 512.

It should be appreciated that the pose of the ultrasound device 502 may be identified without the marker 510. For example, the ultrasound device 502 may have distinctive characteristics (e.g., shape and/or color) that may be readily identifiable in the image 512. Thereby, the computing device 504 may identify the pose of the ultrasound device 502 in the image 510 by analyzing one or more characteristics of the ultrasound device 502 in the image 510.

Figure 6:
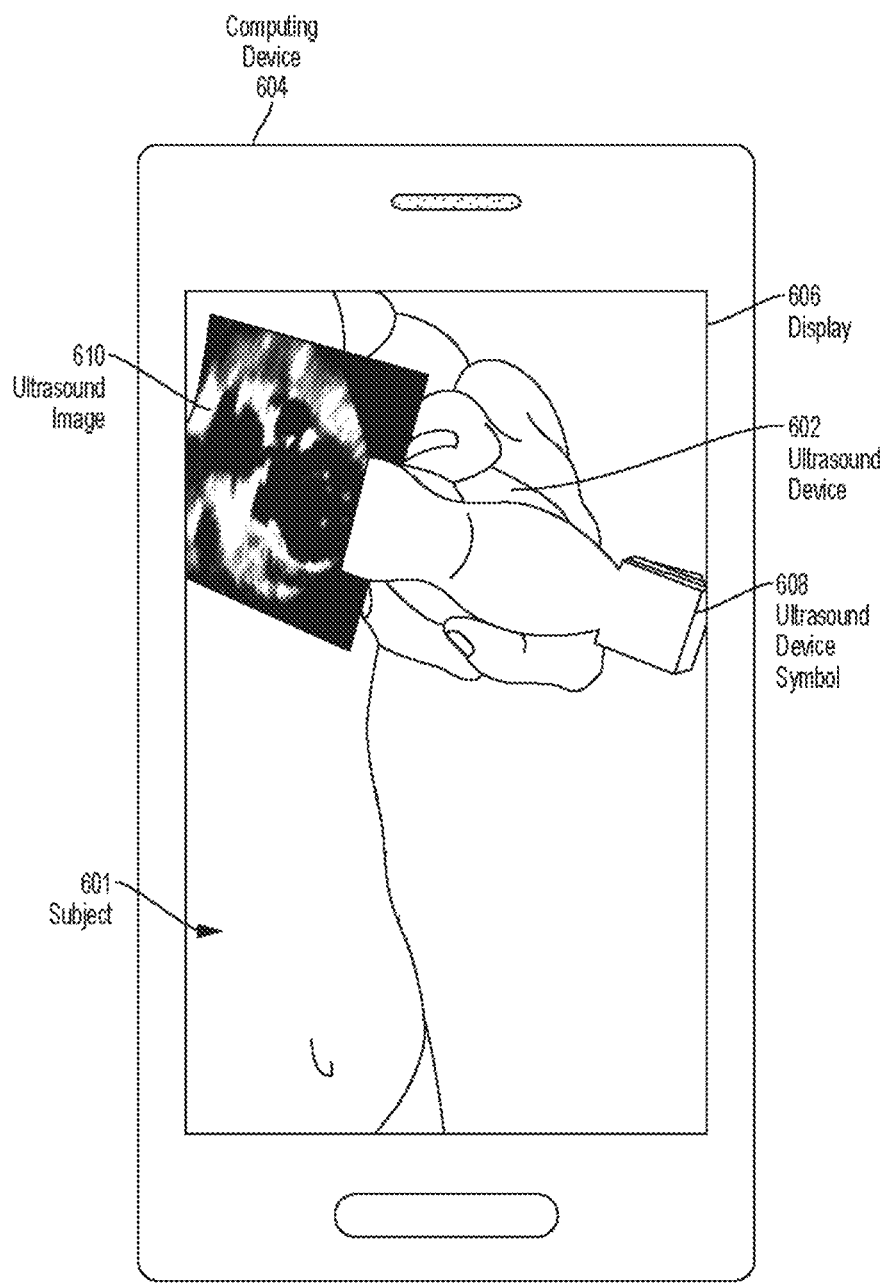
FIG. 6 shows an exemplary augmented reality interface according to some embodiments of the disclosure.

In some embodiments, the identified pose of the ultrasound device 502 in the image 512 may be employed to overlay other elements onto the image 512 separate from the instruction 516. For example, the identified pose of the ultrasound device 502 may be employed to overlay the ultrasound image 514 over the image 512 such that ultrasound image 514 appears to be extending out of the ultrasound device 502 into the subject 501. Such a configuration may advantageously provide an indication to the operator of the particular portion of the subject that is being imaged by the ultrasound device 502. An example of such an augmented reality interface is shown in FIG. 6 being displayed on a display 606 of a computing device 604. The augmented reality interface overlays the ultrasound image 610 and an ultrasound device symbol 608 onto an image of an ultrasound device 602 being used to image the subject 601 (e.g., captured from a front-facing camera in the handheld device computing device 604). As shown, the ultrasound image 610 is overlaid onto the portion of the subject 601 that is being imaged by the ultrasound device 602. In particular, the ultrasound image 610 has been positioned and oriented so as to be extending from the ultrasound device 602 into the subject 601. This position and orientation of the ultrasound image 610 may indicate to the operator the particular portion of the subject 601 that is being imaged. For example, the ultrasound device 602 may be positioned on an upper torso of the subject 601 and the ultrasound image 610 may extend from an end of the ultrasound device 602 in contact with the subject 601 into the upper torso of the subject 601. Thereby, the operator may be informed that the captured image is that of a 2D cross-section of body tissue in the upper torso of subject 601.

It should be appreciated that additional (or fewer) elements may be overlaid onto the image of the ultrasound device 602 being used on the subject 601 in FIG. 6. For example, the ultrasound device symbol 608 overlaid onto the ultrasound device 602 may be omitted. Additionally (or alternatively), the user interface may overlay instructions (e.g., augmented reality arrows) onto the image of the ultrasound device 602 on the subject 601 to provide guidance to the operator.

Example Diagnostic Applications

The inventors have recognized that ultrasound imaging techniques may be advantageously combined with diagnostics and treatment recommendations to provide an ecosystem of intelligent and affordable products and services that democratize access to medical imaging and accelerate imaging into routine clinical practice and/or patient monitoring. This may provide an advance in conventional clinical decision support (CDS) applications by empowering healthcare professionals and/or patients to make diagnostic and treatment decisions at an earlier state of disease, as well as to assist novice imaging users (e.g., consumers) to detect various conditions earlier and monitor patient response to therapy.

The technology improvements described herein may enable, among other capabilities, focused diagnosis, early detection and treatment of conditions by an ultrasound system. The ultrasound system may comprise an ultrasound device that is configured to capture ultrasound images of the subject and a computing device in communication with the ultrasound device. The computing device may execute a diagnostic application that is configured to perform, for example, one or more of the following functions: (1) acquire medical information regarding the subject, (2) identify an anatomical view of the subject to image with the ultrasound device based on the acquired medical information regarding the subject, (3) guide the operator to capture ultrasound image(s) that contain the identified anatomical view, (4) provide a diagnosis (or pre-diagnosis) of a medical condition of the subject based on the captured ultrasound images, and (5) provide one or more recommended treatments based on the diagnosis.

FIGS. 7A-7H show an example user interface for a diagnostic application that is configured to assist an operator determine whether a subject is experiencing heart failure. The diagnostic application may be designed to be used by, for example, a health care professional such as a doctor, a nurse, or a physician assistant. The diagnostic application may be executed by, for example, a computing device 704. The computing device 704 may comprise an integrated display 706 that is configured to display one or more user interface screens of the diagnostic application. The computing device 704 may be communicatively coupled to an ultrasound device (not shown) using a wired or wireless communication link.

Figure 7B:
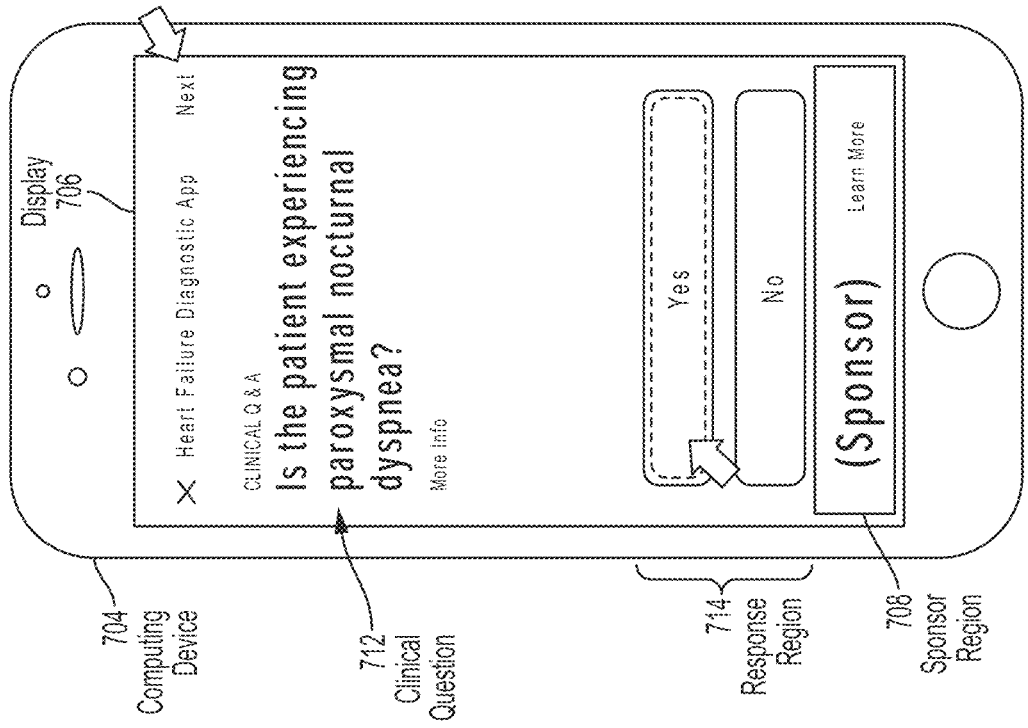
FIGS. 7A-7H show an exemplary user interface for a diagnostic application according to some embodiments of the disclosure.
Figure 7A:
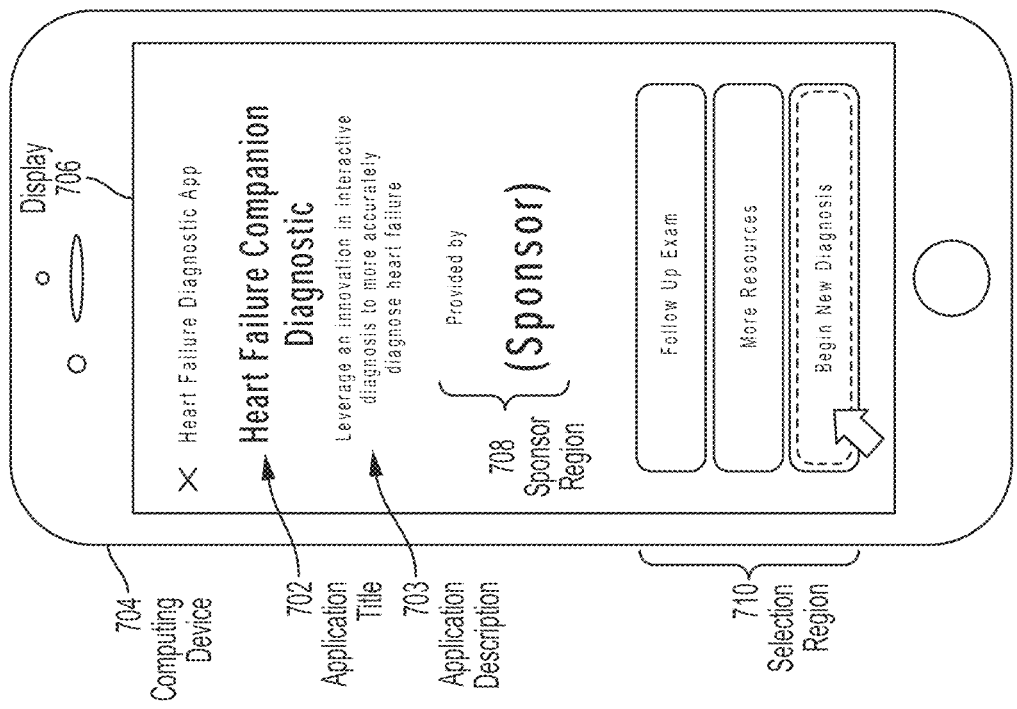

FIG. 7A shows an example home screen that may be displayed upon the diagnostic application being launched. Information that may be presented on the home screen include an application title 702, an application description 703, and a sponsor region 708. The sponsor region 708 may display information, for example, indicating the name, symbol, or logo of any sponsoring entity providing the diagnostic application. In the case of a heart failure diagnostic application, a pharmaceutical manufacturer that provides one or more medications or therapies for treating such a condition may sponsor the application. The home screen may further include a selection region that allows the operator to perform various functions within the diagnostic application such as: schedule a follow-up examination with the subject, access more medical resources, or begin a new diagnosis.

The computing device 704 may transition from the home screen to a clinical Q&A screen shown in FIG. 7B responsive to the "Begin New Diagnosis" button in selection region 710 being activated in the home screen shown in FIG. 7A. The clinical Q&A screen may pose one or more clinical questions 712 to the operator. For a heart failure diagnosis application, an appropriate clinical question 712 posed to the operator may be: "Is the patient experiencing paroxysmal nocturnal dyspnea?" Paroxysmal nocturnal dyspnea may be attacks of severe shortness of breath and coughing that generally occur at night. Such attacks may be a symptom of congestive heart failure. The diagnostic application may receive an answer to the clinical question in the response region 712. As will also be noted from FIG. 7B, the sponsor region 708 may continue to be provided in the diagnostic application. The sponsor region 708 may comprise a link to exit the diagnostic application to a site hosted by the sponsor.

The computing device 704 may transition from the clinical Q&A screen to an examination screen responsive to the "Yes" button being activated in response region 714. The examination screen may pose one or more examination questions 718 to the operator. For a heart failure diagnostic application, the examination question 718 may be to determine a current heart rate of the subject to be diagnosed. The diagnostic application may receive a response through the response region 720. For example, the operator may indicate that the heart rate of the subject is below a first value (e.g., less than 91 beats per minute (bpm)), within a range between the first value and a second value (e.g., between 91 and 110 bpm), or above the second value (e.g., more than 110 bpm) in the response region 720.

Figure 7D:
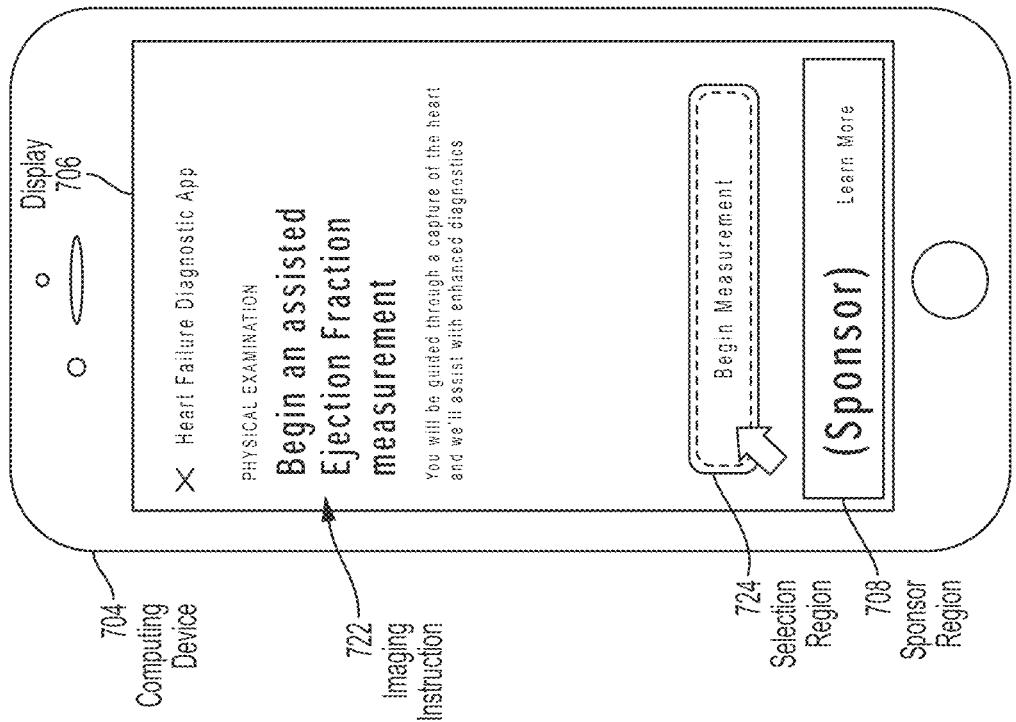
Figure 7C:
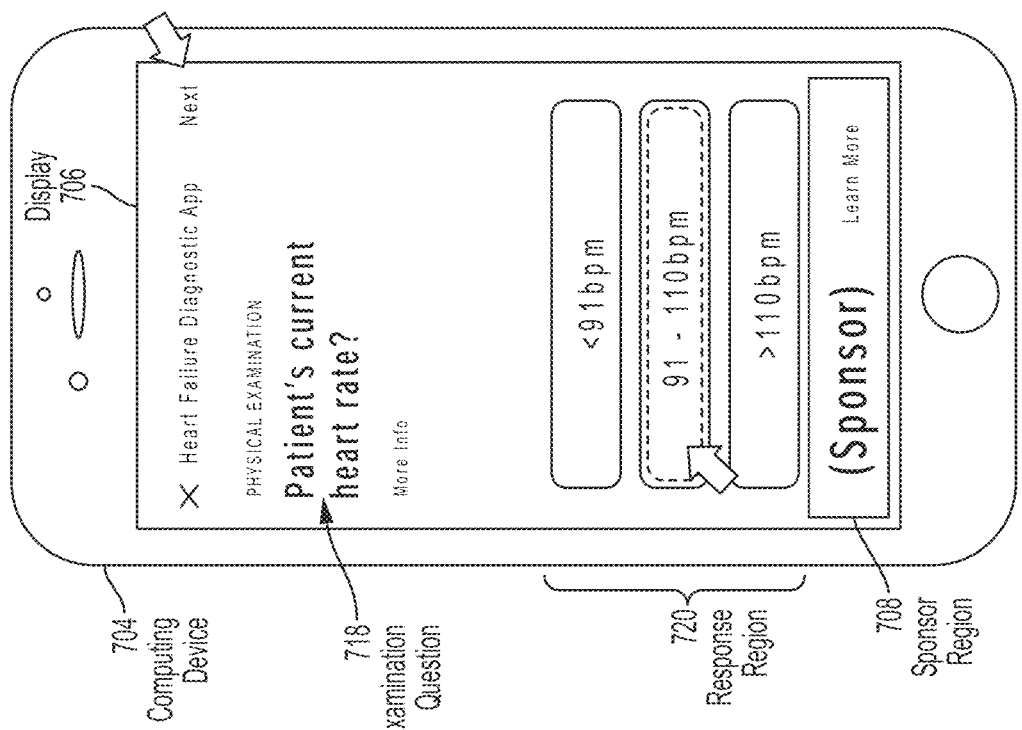

Once the computing device 704 has received a response to the examination question 718, the computing device 704 may transition from the examination screen shown in FIG. 7C to an ultrasound image acquisition screen shown in FIG. 7D. The ultrasound image acquisition screen may present an imaging instruction 722 to the operator. For a heart failure diagnostic application, the imaging instruction 722 may instruct the operator to begin an assisted ejection fraction (EF) measurement of the subject. EF may be a measure of how much blood a heart ventricle pumps out with each contraction. The EF may be identified be computed by, for example, analyzing one or more ultrasound images of a heart of the subject. The computing device 704 may begin an assisted EF measurement process responsive to the "Begin Measurement" button in selection region 724 being activated.

The computing device 702 may communicate with an ultrasound device to capture ultrasound images response to the "Begin Measurement" button being activated in the selection region 724. The computing device 702 may also transition from the image acquisition screen shown in FIG. 7D to an image acquisition assistance screen shown in FIG. 7E. The image acquisition assistance screen may display an ultrasound image 726 captured using the ultrasound device. In some embodiments, the image acquisition assistance screen may display one or more instructions regarding how to reposition the ultrasound device to obtain an ultrasound image that contains the target anatomical view (e.g., a PLAX view). Once the ultrasound device has been properly positioned, the image acquisition assistance screen may display an indication that the ultrasound device is properly positioned. When a suitable (clinically relevant) image(s) is obtained, the operator may confirm the acquisition via the "Confirm" button.

Figure 7F:
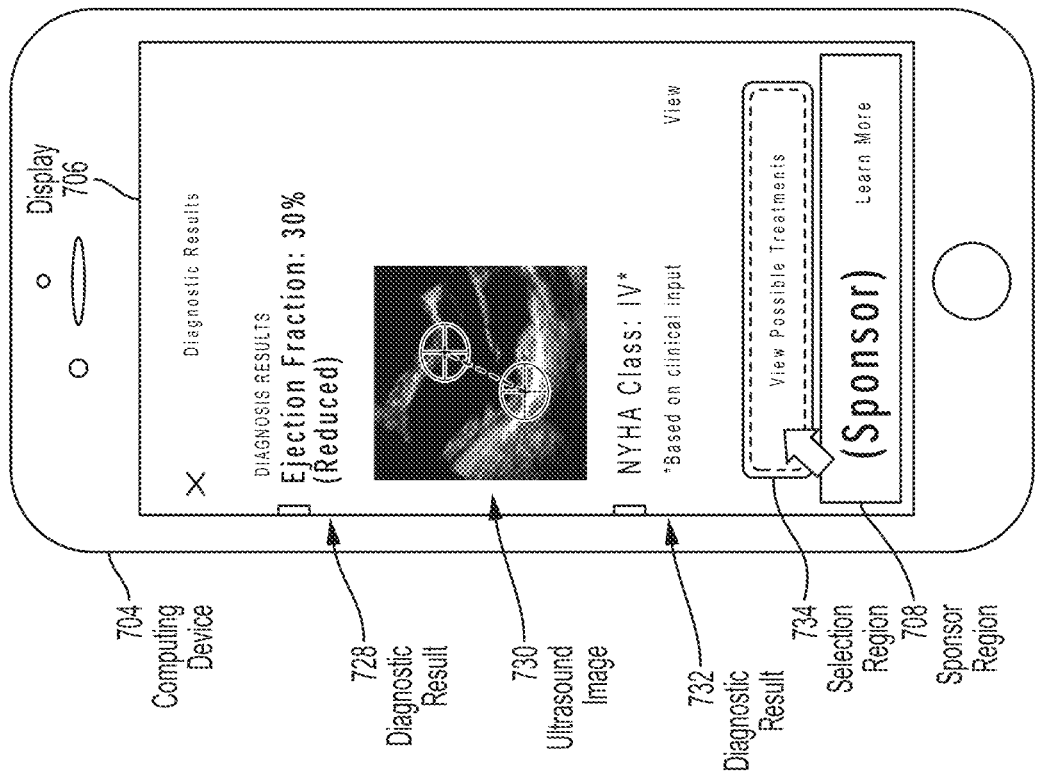
Figure 7E:
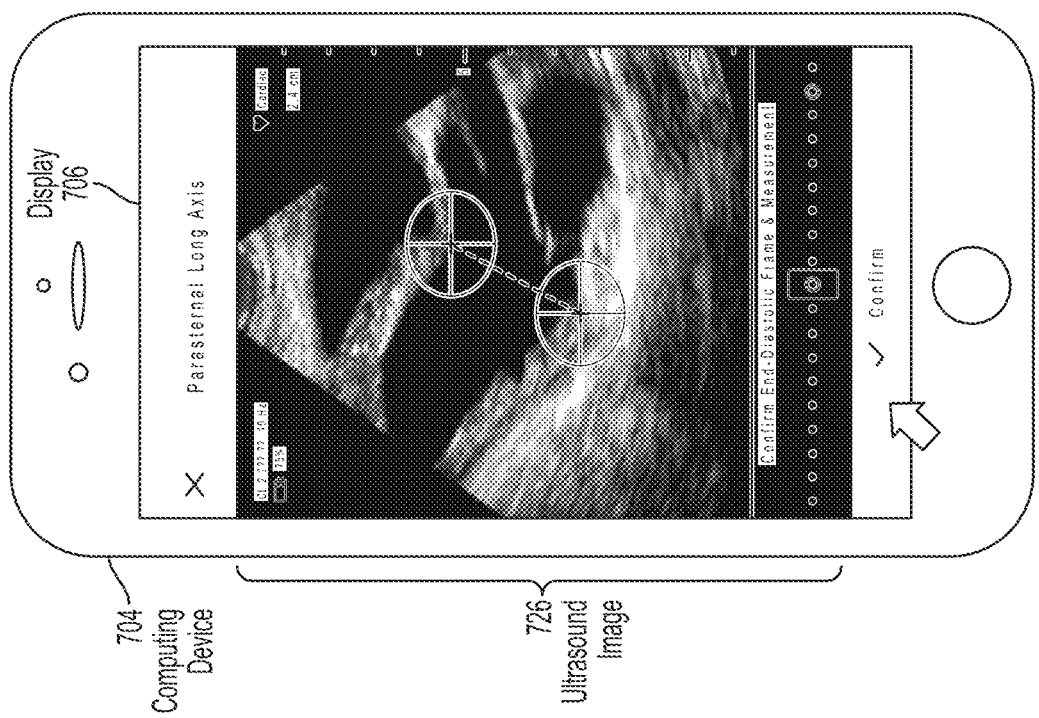

The computing device 704 may transition from the image acquisition assistance screen shown in FIG. 7E to a diagnostic results screen shown in FIG. 7F once the ultrasound images have been confirmed by the operator. The diagnostic results screen may display diagnostic results 728, 732 determined from analyzing the captured ultrasound image 730. As shown, the diagnostic results screen may display an EF of 30% for the subject and an associated New York Heart Association (NYHA) classification of IV. This classification system utilizes four categories of heart failure, from I-IV with IV being the most severe.

Figure 7H:
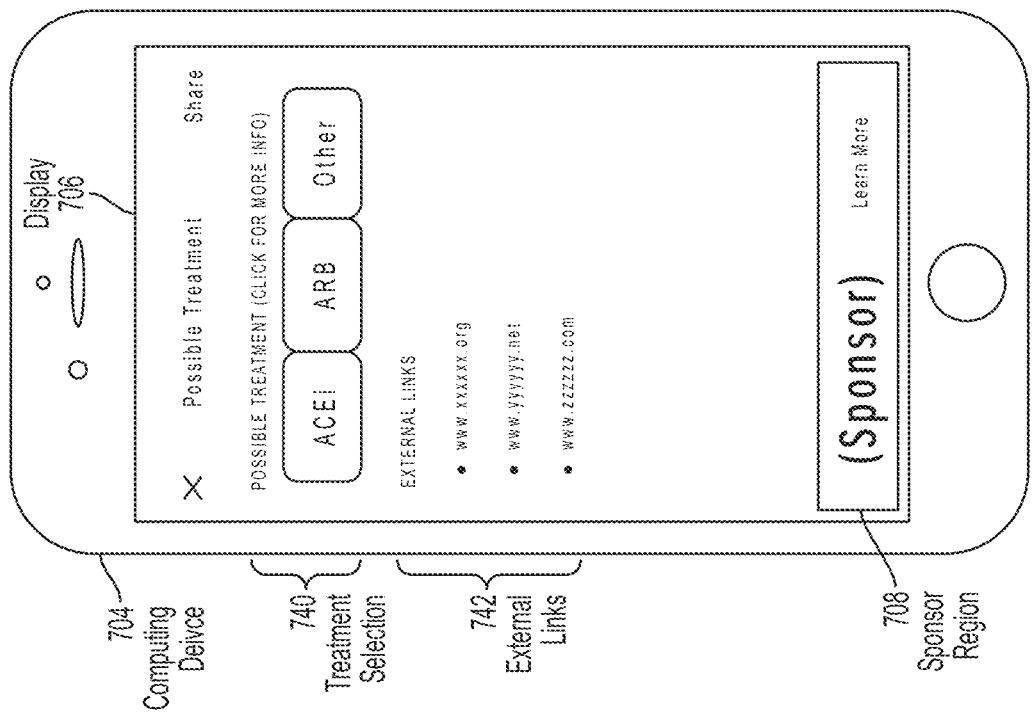
Figure 7G:
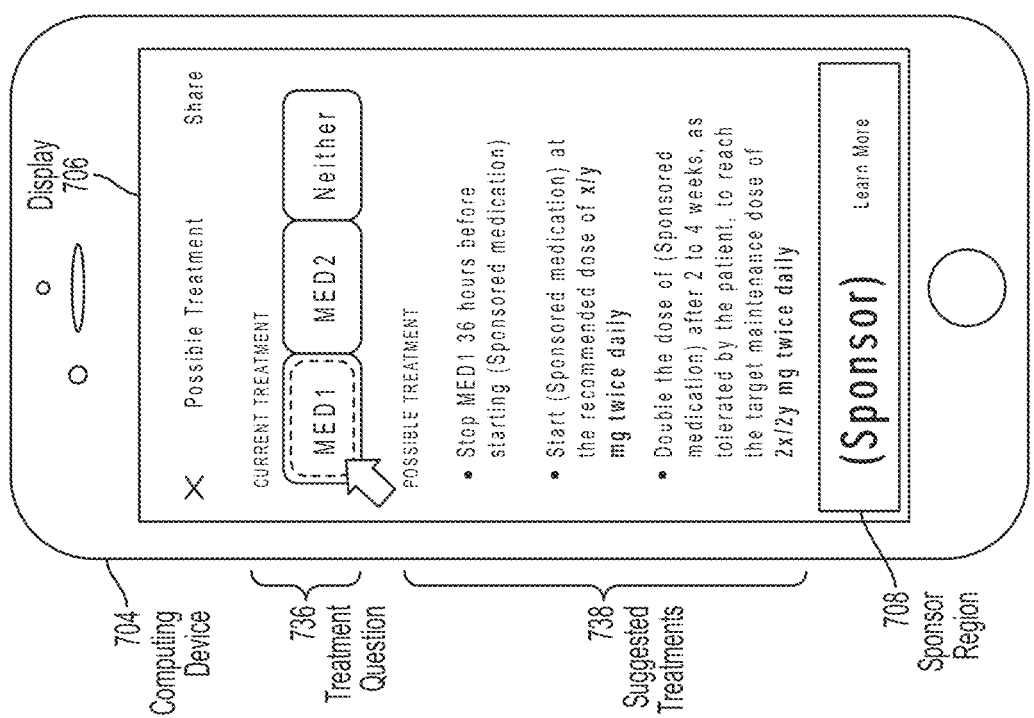

The computing device 704 may transition from the diagnostic results screen shown in FIG. 7F to one or more of the treatment screens shown in FIGS. 7G and 7H responsive to the "view possible treatments" button being activated in selection region 734. The treatment screen shown in FIG. 7G may display a treatment question 736 regarding a current treatment being provided to the subject and suggested treatments 738 determined based on, for example, any one of the following: (1) a response to the treatment question 736, (2) diagnostic results, (3) the captured ultrasound image, (4) a response to the physical examination question, and/or (5) a response to the clinical question. The treatment screen shown in FIG. 7H may be an extension of the treatment screen in FIG. 7G. For example, an operator may access the treatment screen in FIG. 7H by scrolling down from the treatment screen shown in FIG. 7G. The treatment screen in FIG. 7H may display a treatment selection 740 where an operator may select which treatment they want to provide to the subject. As shown, the treatment selection 740 may allow an operator to pick between one or more medications to treat heart failure such as angiotensin-converting-enzyme inhibitors (ACE inhibitors), angiotensin receptor blockers (ARB), or other alternatives. The diagnostic application may, then, display one or more external links 742 based on the selected treatment to provide more information to the operator regarding the treatment.

It should be appreciated that diagnostic application shown in FIGS. 7A-7H is only one example implementation and other diagnostic applications may be created for other conditions separate and apart from congestive heart failure. Further, diagnostic applications may be created for use by a subject at-home (instead of a physician). For example, a physician may issue an ultrasound device configured for in-home use by a subject to monitor a condition of the subject using the ultrasound device. A diagnostic application may also be provided to the subject to use with the ultrasound device. Such a diagnostic application may be installed on a personal mobile smartphone or tablet of the subject. The diagnostic application may be configured to assist the subject to operate the ultrasound device and store (and/or upload) the captured ultrasound images for analysis by the physician. Thereby, the physician may be able to remotely monitor a condition of the subject without making the subject remain in inpatient care.

FIGS. 8A-8D show an example user interface for such a diagnostic application that is designed to be used by a subject in an at-home environment. The diagnostic application may be configured to assist an operator (e.g., the subject) use an ultrasound device to capture ultrasound images in an at-home setting. The diagnostic application may be executed by, for example, a computing device 804 (such as a mobile smartphone or a tablet of the subject). The computing device 804 may comprise an integrated display 806 that is configured to display one or more user interface screens of the diagnostic application. The computing device 804 may be communicatively coupled to an ultrasound device (not shown) using a wired or wireless communication link. The computing device may also comprise an imaging device 805 (e.g., a camera) that is configured to capture non-acoustic images. The imaging device 805 may be disposed on a same side as the display 806 to allow the operator to simultaneously capture images of themselves holding an ultrasound device while viewing one or more instructions displayed on the display 806.

Figures 8A, 8B:
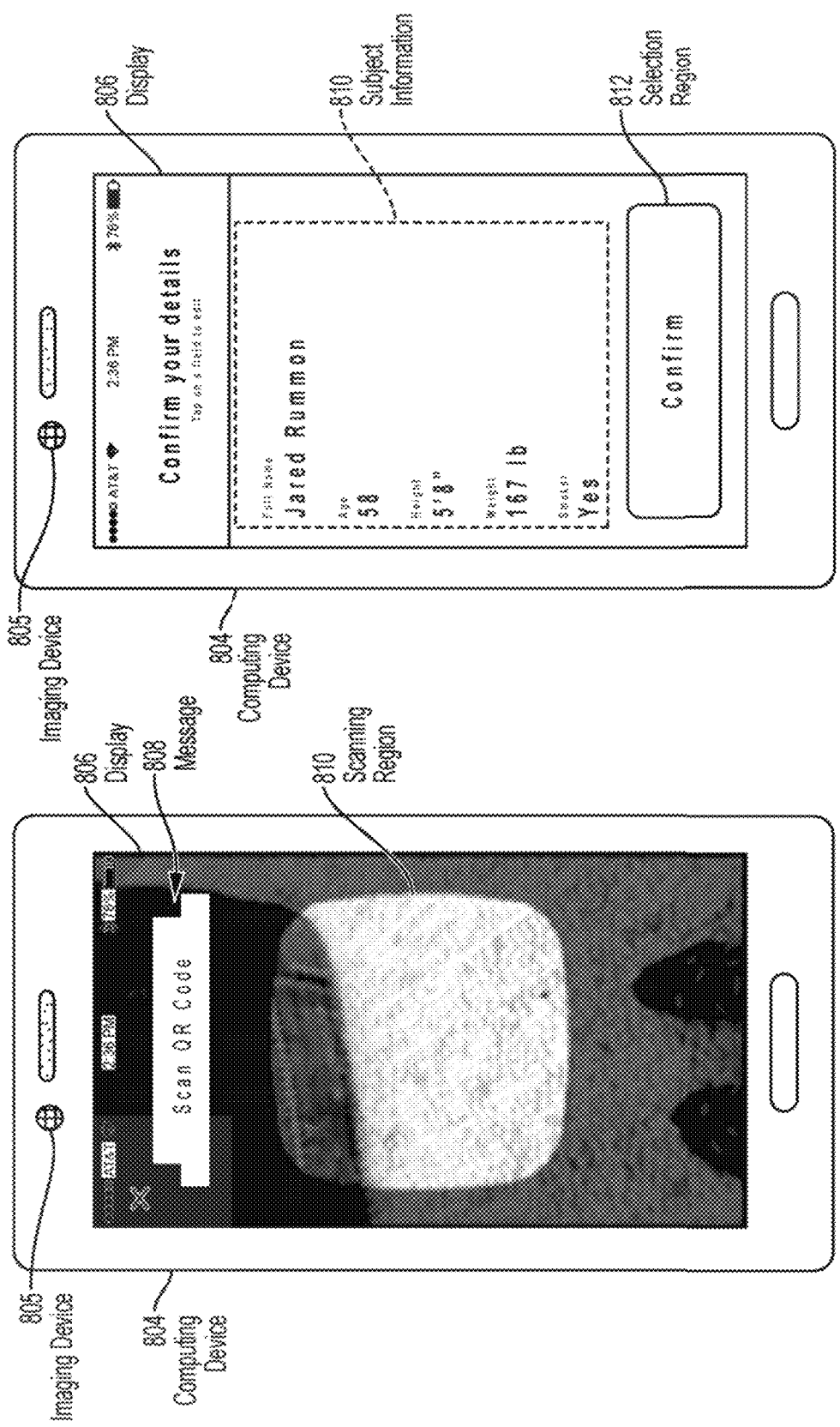
FIGS. 8A-8D show an exemplary user interface for an at-home diagnostic application according to some embodiments of the disclosure.

FIG. 8A shows an example home screen that may be displayed upon the diagnostic application being launched. The home screen includes a message 808 to the operator to instruct the operator to scan a quick response (QR) code associated with the ultrasound device. The QR code may be, for example, disposed on the ultrasound device itself and/or disposed on a packaging associated with the ultrasound device. The home screen may also display images captured by an imaging device (e.g., integrated into the computing device 804 and disposed on a side opposite the display 806). The home screen may show a scanning region 810 in the captured images to illustrate where a user should place the QR code in the field of view of the imaging device to have the QR code read.

Once the computing device 804 reads the QR code, the computing device 804 may transition from the home screen shown in FIG. 8A to a subject information screen shown in FIG. 8B. The subject information screen may include a display of subject information 810 obtained by the computing device 804 using the scanned QR code. For example, the computing device 804 may have employed the scanned QR code to access medical records of the subject in a remote server. Once the operator has confirmed that the subject information 810 is correct, the operator may activate the confirm button in the selection region 812.

It should be appreciated that other types of bar codes may be employed separate from QR codes. Other example bar codes include: MaxiCode bar codes, Codabar bar codes, and Aztec bar codes.

Figures 8C, 8D:
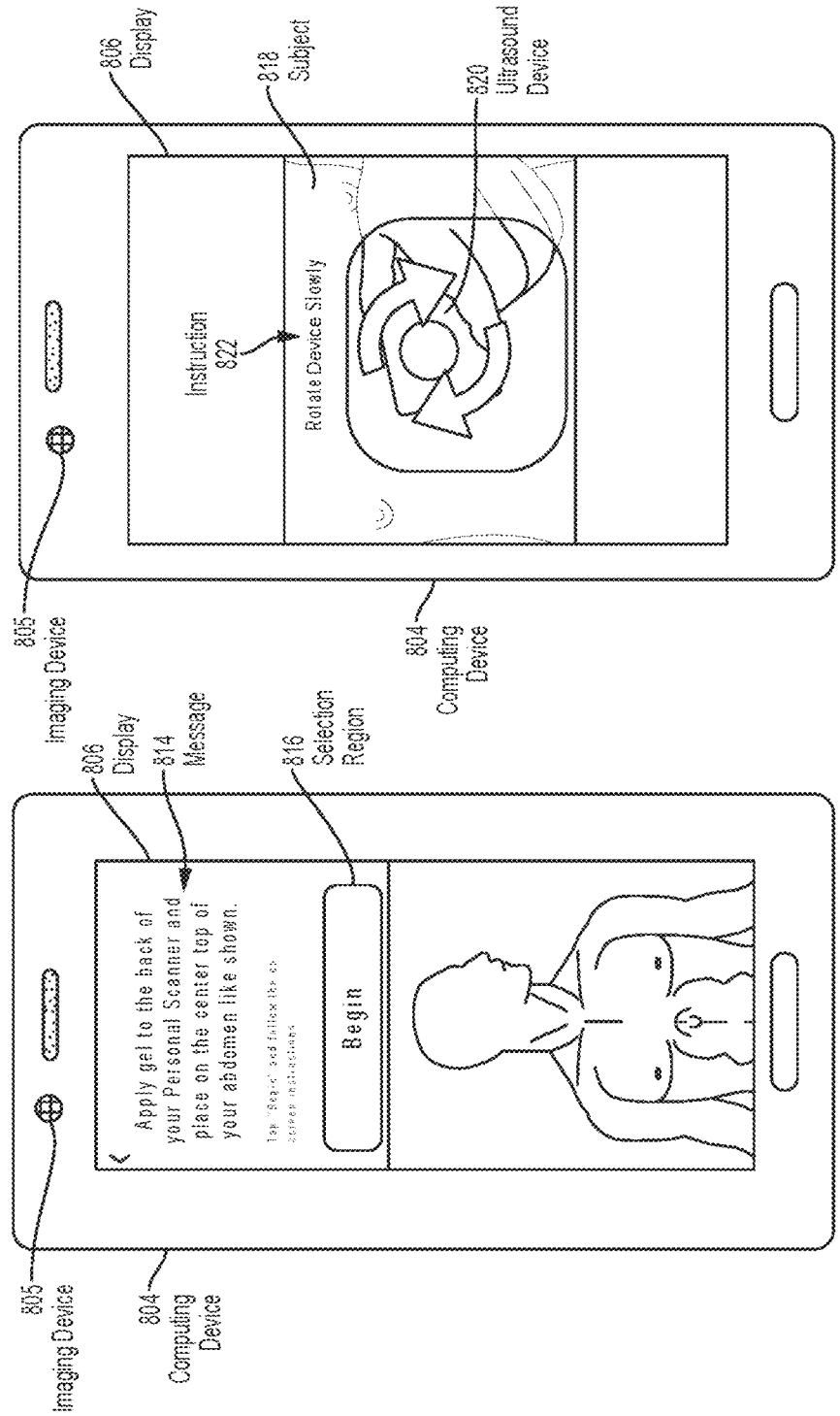

The computing device 804 may transition from the subject information screen shown in FIG. 8B to the image acquisition screen shown in FIG. 8C responsive to the "Confirm" button being activated in the selection region 812. As shown, the image acquisition screen includes a message 814 for the operator to apply gel to the ultrasound device and a selection region 816 including a being button for the operator to begin acquisition of ultrasound images.

The computing device 804 may transition from the image acquisition screen shown in FIG. 8C to the image acquisition assistance screen shown in FIG. 8D responsive to the "Begin" button being activated in the selection region 816. As shown, the image acquisition assistance screen may include a non-acoustic image (e.g., captured by the imaging device 805) of a subject 818 holding an ultrasound device 820. An instruction 822 may be superimposed over the captured non-acoustic image to guide the operator (e.g., the subject) to capture an ultrasound image containing a target anatomical view. Once the computing device 804 has captured the ultrasound image containing the target anatomical view, the computing device 804 may locally store the captured ultrasound image for later retrieval by a physician and/or upload the image to an external server to be added to a set of medical records associated with the subject. The computing device 804 may further display a confirmation to the operator that the ultrasound image was successfully captured.

Example Processes

Figure 9:
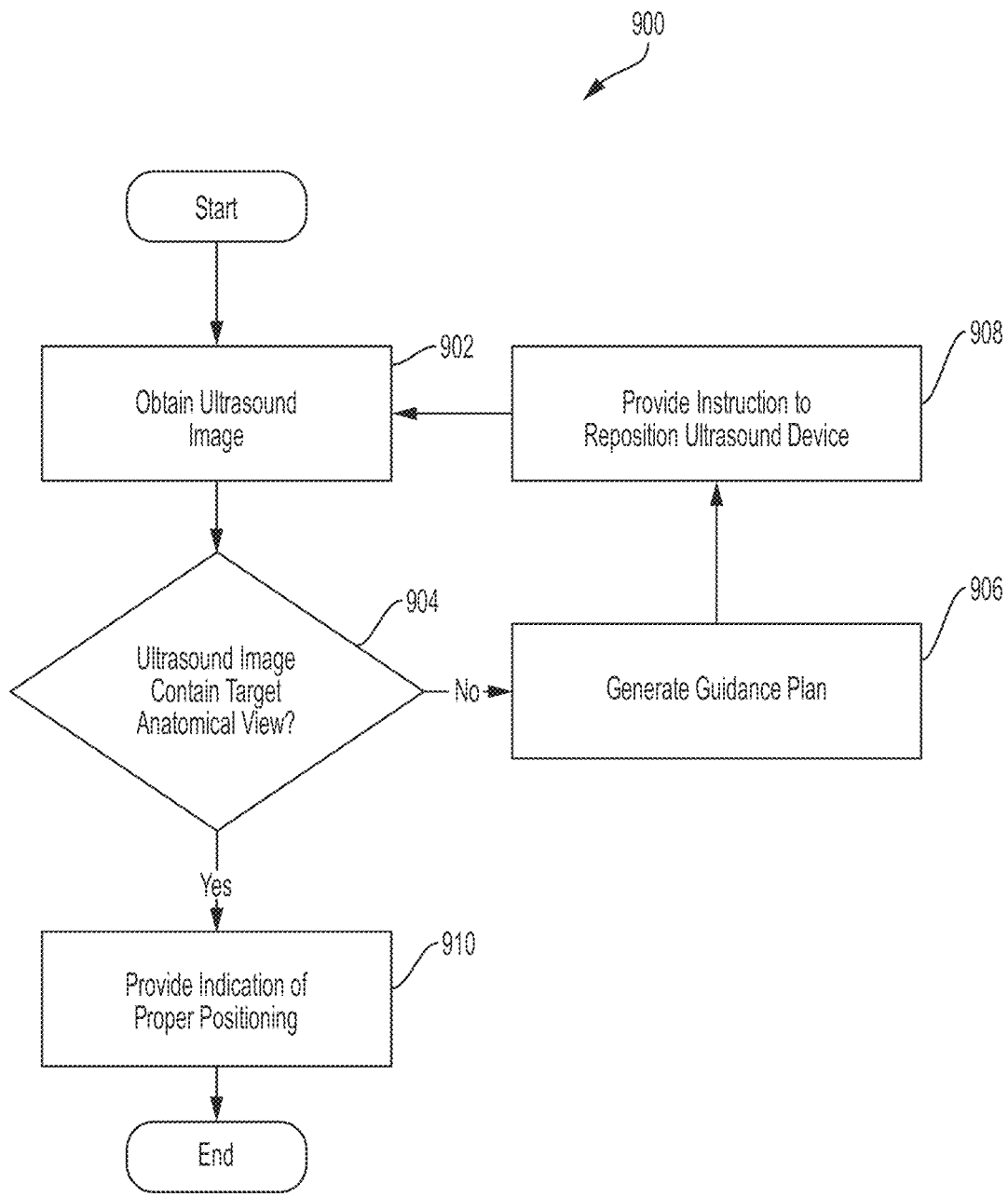
FIG. 9 shows an exemplary method of guiding an operator of an ultrasound device to capture an ultrasound image containing a target anatomical view according to some embodiments of the disclosure.

FIG. 9 shows an example process 900 for guiding an operator of an ultrasound device to capture an ultrasound image that contains a target anatomical view. The process 900 may be performed by, for example, a computing device in an ultrasound system. As shown, the process 900 comprises an act 902 of obtaining an ultrasound image, an act 904 of determining whether the ultrasound image contains the target anatomical view, an act 906 of generating a guidance plan, an act 908 of providing instructions to reposition the ultrasound device, and an act 910 of providing an indication of proper positioning.

In act 902, the computing device may obtain an ultrasound image of the subject. The computing device may obtain the ultrasound image by communicating with an ultrasound device communicatively coupled to the computing device. For example, the computing device may send an instruction to the ultrasound device to generate ultrasound data and send the ultrasound data to the computing device. The computing device may, in turn, use the received ultrasound data to generate the ultrasound image. Additionally (or alternatively), the ultrasound image may be generated by the ultrasound device and the computing device may retrieve the ultrasound image from the ultrasound device.

In act 904, the computing device may determine whether the ultrasound image contains the target anatomical view. If the computing device determines that the ultrasound image contains the target anatomical view, the computing device may proceed act 910 and provide an indication of proper positioning. Otherwise the system may proceed to act 906 to generate a guidance plan for the operator to move the ultrasound device.

In some embodiments, the computing device may employ an automated image processing technique, such as a deep learning technique, to determine whether the ultrasound image contains the target anatomical view. For example, the ultrasound image may be provided as input to a neural network that is trained to identify an anatomical view contained in the ultrasound image. The output of such a neural network may be an indication of the particular anatomical view that is contained in the ultrasound image. In this example, the identified anatomical view may be compared with the target anatomical view to determine whether they match. If the identified anatomical view and the target anatomical view match, the computing device may determine that the ultrasound image contains the target anatomical view. Otherwise, the computing device may determine that the ultrasound image does not contain the anatomical view. In another example, the neural network may be configured to directly provide an indication of an instruction for the operator based on an input ultrasound image. Thereby, the neural network may provide as an output a confirmation that the ultrasound devices properly positioned or an instruction to move the ultrasound device in a particular direction. In this example, the computing device may determine that the ultrasound image contains the target anatomical view responsive to the neural network providing a confirmation as an output. Otherwise, the computing device may determine that the ultrasound image does not contain the anatomical view.

In act 906, the computing device may generate a guidance plan regarding how to guide the operator to move the ultrasound device. In some embodiments, the guidance plan may comprise a guide path along which the operator should move the ultrasound device from an initial position to a target position where an ultrasound image containing the target anatomical view may be captured. In these embodiments, the computing device may identify the initial position of the ultrasound device on the subject at least in part by: identifying an anatomical view contained in the ultrasound image (e.g., using deep learning techniques) and map the identified anatomical view to a position on the subject. The target position may be identified by, for example, mapping the target anatomical view to a position on the subject. Once the initial and target positions have been identified, the computing device may identify a guide path between the initial and target positions along which the ultrasound device should move. The guide path may comprise a sequence of directions (e.g., translational directions or rotational directions) for the ultrasound device to travel along to reach the target position. The generated guide path may not be the shortest path between the initial position of the ultrasound device in the target position of the ultrasound device. For example, the generated path may avoid using diagonal movements that may be challenging to properly convey to the operator. Alternatively (or additionally), the generated path may avoid certain areas of the subject such as areas comprising hard tissues. Once the guide path between the initial position and the target position of the ultrasound device has been determined, the computing device may generate a sequence of one or more instructions to provide to the operator to instruct the operator to move the ultrasound device along the guide path.

In act 908, the computing device may provide an instruction to reposition the ultrasound device to the operator. The instruction may be, for example, an audible instruction played through a speaker, a visual instruction displayed using a display, and/or a tactile instruction provided using a vibration device (e.g., integrated into the computing device and/or the ultrasound device). The instruction may be provided based on, for example, the sequence of instructions in the guidance plan generated in act 906. For example, the computing device may identify a single instruction from the sequence of instructions and provide the identified instruction. It should be appreciated that the instruction need not originate from a guidance plan. For example, as discussed above, a neural network may be configured to directly output an instruction based on a received ultrasound image. In this example, the output instruction may be directly provided and the act 906 of generating a guidance plan may be omitted.

Once the computing device has provided the instruction to reposition the ultrasound device, the computing device may repeat one or more of acts 902, 904, 906 and/or 908 to provide the operator additional instructions.

In act 910, the computing device may provide an indication of proper positioning. For example, the computing device may provide an audible confirmation played through a speaker, a visual confirmation displayed using a display, or a tactile confirmation provided through a vibration device.

Figure 10:
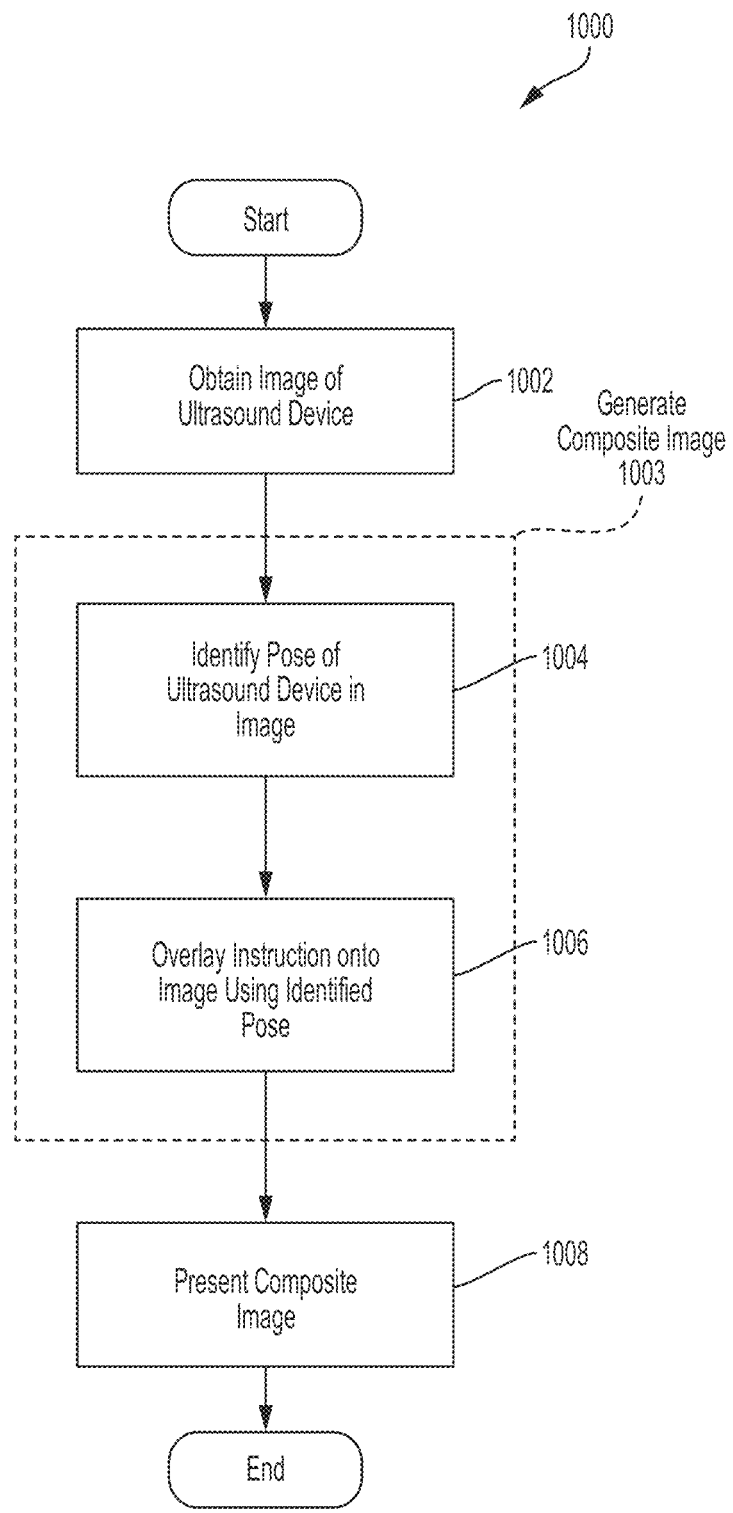
FIG. 10 shows an exemplary method of providing an augmented reality interface to an operator of an ultrasound device embodiments of the disclosure.

FIG. 10 shows an example process 1000 for providing an augmented reality interface for an operator. The augmented reality interface may include a non-acoustic image of a real-world environment including an ultrasound device and one or more elements (such as instructions) overlaid onto the non-acoustic image. The process 1000 may be performed by, for example, a computing device in an ultrasound system. As shown in FIG. 10, the process 1000 comprises an act 1002 of obtaining an image of an ultrasound device, an act 1003 of generating a composite image, and an act 1008 of presenting the composite image. The act 1003 of generating the composite image may comprise an act 1004 of identifying a pose of an ultrasound device in the image and an act 1006 of overlaying the instruction onto the image using the identified pose.

In act 1002, the computing device may capture an image (e.g., a non-acoustic image) of the ultrasound device. The non-acoustic image may be captured by an imaging device (e.g., a camera) integrated into the computing device. For example, the non-acoustic image may be captured using a front-facing camera of a mobile smartphone (e.g., on the same side as the display) when the operator is also the subject. In another example, the non-acoustic image may be captured using a rear-facing camera of a mobile smartphone (e.g., on the opposite side as the display) when the operator is a person (or group of people) separate from the subject.

In act 1003, the computing may generate the composite image. The composite image may comprise the non-acoustic image captured in act 1002 and one or more elements overlaid onto the non-acoustic image. The one or more elements overlaid onto the non-acoustic image may be, for example, one or more instructions designed to provide feedback to the operator regarding how to reposition the ultrasound device to obtain an ultrasound image that contains a target anatomical view. The computing device may generate the composite image in any of a variety of ways. In some embodiments, the computing device may be configured to generate the composite image by performing acts 1004 and 1006.

In act 1004, the computing device may identify a pose (e.g., position and/or orientation) of the ultrasound device in the non-acoustic image. The computing device may identify the pose of the ultrasound device in the captured image using an automated image processing technique (e.g., a deep learning technique). For example, the non-acoustic image may be provided as an input to a neural network that is configured to identify which pixels in the non-acoustic image are associated with the ultrasound device. In this example, the computing device may use the identified pixels to determine a position of the ultrasound device in the non-acoustic image. In some embodiments, the ultrasound device may have a marker disposed thereon that is visible in the image to ease identification of the ultrasound device in the non-acoustic image. The marker may have a distinct shape, color, and/or image that is easy to recognize using an automated image processing technique. Additional information may also be employed to identify the pose of the ultrasound device in combination with (or in place of) the information extracted from the non-acoustic image. For example, the ultrasound device may comprise one or more sensors configured to detect movement (e.g., accelerometers, gyroscopes, compasses, and/or inertial measurement units). In this example, movement information from these sensors in the ultrasound device may be employed to determine the pose of the ultrasound device. In another example, the ultrasound device (e.g., ultrasound device 502) and a computing device (e.g., computing device 504) connected to the ultrasound device may comprise sensors configured to detect movement. In this example, the movement information from the sensors in both the ultrasound device and the computing device may be used in concert to identify the pose of the ultrasound device relative to the computing device and, thereby, identify the pose of the ultrasound device in the captured non-acoustic image.

In act 1006, the computing device may overlay an instruction onto the non-acoustic image using the identified pose to form an augmented reality interface. For example, the computing device may overlay an instruction regarding how to move the ultrasound device (e.g., a directional arrow) onto the non-acoustic image so as to be proximate and/or partially covering the ultrasound device. Additionally (or alternatively), the pose may be employed to position other elements in the augmented reality interface. For example, the pose of the ultrasound device may be employed to position an ultrasound image in the augmented reality interface. In this example, the ultrasound image may be positioned in the augmented reality interface so as to appear to be extending from the ultrasound device in the non-acoustic image into the subject. Thereby, the operator may gain an appreciation for the particular portion of the subject that is being imaged with the ultrasound device.

In act 1008, the computing device may present a composite image to the operator. For example, the computing device may present the composite image to the operator using a display integrated into the computing device. Alternative (or additionally), the computing device may transmit the composite image to another device (e.g., to be presented on a display of the other device).

Figure 11:
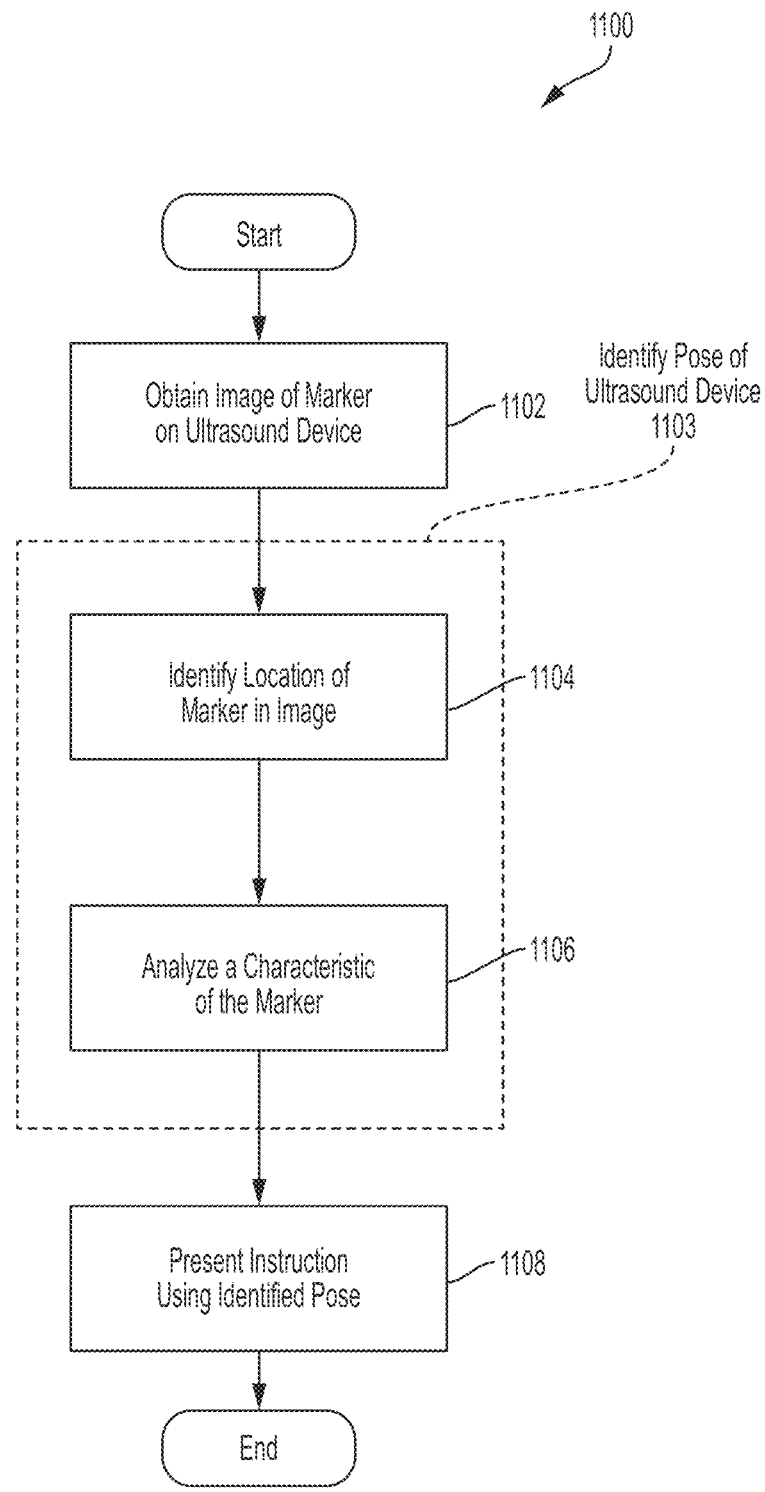
FIG. 11 shows an exemplary method of tracking a location of an ultrasound device according to some embodiments of the disclosure.

FIG. 11 shows an example process 1100 for tracking the location of an ultrasound device in non-acoustic images using a marker disposed thereon. The process 1100 may be performed by, for example, a computing device in an ultrasound system. As shown, the process 1100 comprises an act 1102 of obtaining an image of a marker disposed on an ultrasound device, an act 1103 of identifying a pose of the ultrasound device, and an act 1108 of presenting an instruction using the identified pose. The act 1103 of identifying the pose of the ultrasound device may comprise an act 1104 of identifying the location of the marker in the image and an act 1106 of analyzing a characteristic of the marker.

In act 1102, the computing device may capture a non-acoustic image of the marker on the ultrasound device. The non-acoustic image may be captured by an imaging device (e.g., a camera) integrated into the computing device. For example, the non-acoustic image may be captured using a front-facing camera of a mobile smartphone (e.g., on the same side as the display) when the operator is also the subject. In another example, the non-acoustic image may be captured using a rear-facing camera of a mobile smartphone (e.g., on the opposite side as the display) when the operator is person (or group of people) separate from the subject.

In act 1103, the computing device may identify a pose (e.g., a position and/or orientation) of the ultrasound device in the captured image using the marker. The computing device may identify the pose of the ultrasound device in the captured image in any of a variety of ways. In some embodiments, the computing device may identify the pose of the ultrasound device in the non-acoustic image by performing acts 1104 and 1106.

In act 1104, the computing device may identify a location of the marker in the non-acoustic image. The computing device may use the identified location of the marker to identify a position of the ultrasound device on which the marker is disposed. The location of the marker may be determined by, for example, locating one or more features characteristic to the marker, such as a shape, color, and/or image, in the image using an automated image processing technique.

In act 1106, the computing device may analyze a characteristic of the marker. The computing device may analyze a characteristic of the marker to, for example, determine an orientation of the ultrasound device in the captured image. The particular way in which the computing device determines the orientation using characteristics of the marker may depend on, for example, the particular marker employed. In one example, the marker may be a monochrome marker comprising a pattern. In this example, the pattern may be analyzed in order to determine in orientation of the pattern and, thereby, determine an orientation of the ultrasound device in the non-acoustic image. In another example, the marker may be a dispersive marker that is configured to present different colors depending on the viewing angle. In this example, the computing device may identify a color of the marker in the non-acoustic image and use the identified color to determine an orientation of the marker and, thereby, an orientation of the ultrasound device. In yet another example, the marker may be a holographic marker that is configured to present different images depending on the viewing angle. In this example, the computing device may identify an image presented by the holographic marker and use the identified image to determine an orientation of the marker, and thereby, an orientation of the ultrasound device.

In act 1108, the computing device may present an instruction using the identified pose. In some embodiments, the computing device may overlay the instruction onto the non-acoustic image obtained in act 1102 using the identified pose to form a composite image for an augmented reality interface. For example, the computing device may overlay an instruction regarding how to move the ultrasound device (e.g., a directional arrow) onto the non-acoustic image so as to be proximate and/or partially covering the ultrasound device. Additionally (or alternatively), the pose may be employed to position other elements in the augmented reality interface. For example, the pose of the ultrasound device may be employed to position an ultrasound image in the augmented reality interface. In this example, the ultrasound image may be positioned in the augmented reality interface so as to appear to be extending from the ultrasound device in the non-acoustic image into the subject. Thereby, the operator may gain an appreciation for the particular portion of the subject that is being imaged with the ultrasound device.

Figure 12:
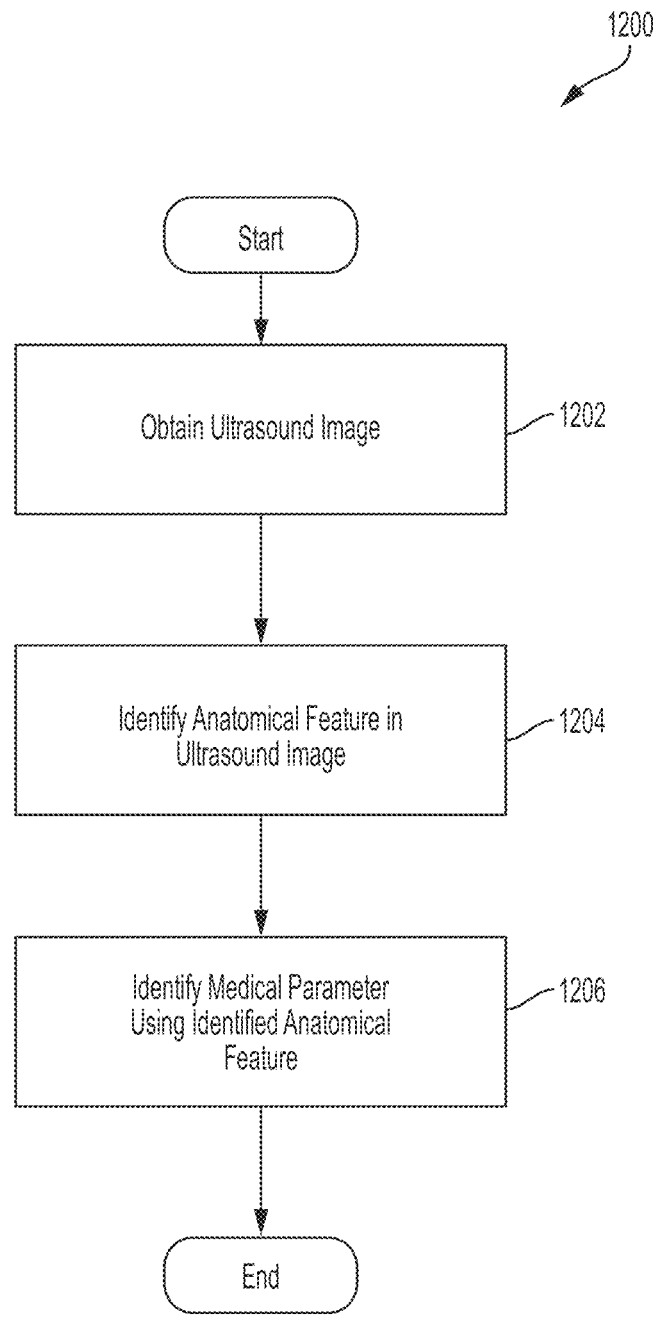
FIG. 12 shows an exemplary method of identifying a medical parameter of a subject using an ultrasound image according to some embodiments of the disclosure.

FIG. 12 shows an example process 1200 for analyzing captured ultrasound images to identify a medical parameter of the subject. The process 1200 may be performed by, for example, a computing device in an ultrasound system. As shown, the process 1200 comprises an act 1202 of obtaining an ultrasound image, an act 1204 of identifying an anatomical feature in the ultrasound image, and an act 1206 of identifying a medical parameter using the identified anatomical feature.

In act 1202, the computing device may obtain an ultrasound image of the subject. The computing device may obtain the ultrasound image by communicating with an ultrasound device communicatively coupled to the computing device. For example, the computing device may send an instruction to the ultrasound device to generate ultrasound data and send the ultrasound data to the computing device. The computing device may, in turn, use the received ultrasound data to generate the ultrasound image.

In act 1204, the computing device may identify an anatomical feature in the ultrasound image. For example, the computing device may identify a heart ventricle, a heart valve, a heart septum, a heart papillary muscle, a heart atrium, an aorta, or a lung as an anatomical feature in the ultrasound image. The computing device may identify the anatomical feature using an automated image processing technique, such as a deep learning technique. For example, the computing device may provide the ultrasound image as an input to a neural network that is configured (e.g., trained) to provide, as an output, an indication of which pixels in the ultrasound image are associated with an anatomical feature. It should be appreciated that this neural network may be separate and distinct from any neural networks employed to guide an operator to obtain an ultrasound image containing a target anatomical view (such as those employed in process 900 described above).

In act 1206, the computing device may identify a medical parameter using the identified anatomical feature. For example, the computing device may determine an ejection fraction, a fractional shortening, a ventricle diameter, a ventricle volume, an end-diastolic volume, an end-systolic volume, a cardiac output, a stroke volume, an intraventricular septum thickness, a ventricle wall thickness, or a pulse rate of the subject. In some embodiments, the computing device may identify the medical parameters by analyzing one or more characteristics of the identified anatomical feature. For example, the computing device may identify a heart ventricle in the ultrasound image and the dimensions of the heart ventricle may be extracted from the ultrasound image to determine a ventricle volume and/or a ventricle diameter. It should be appreciated that the computing device may analyze more than a single ultrasound image to identify the medical parameter. For example, the computing device may identify a ventricle volume in each of a plurality of ultrasound images and select a lowest ventricle volume as the end-systolic volume and select the highest ventricle volume as the end-diastolic volume. Further, the end-systolic and end-diastolic volumes may be employed to determine another medical parameter, such as an EF.

Figure 13:
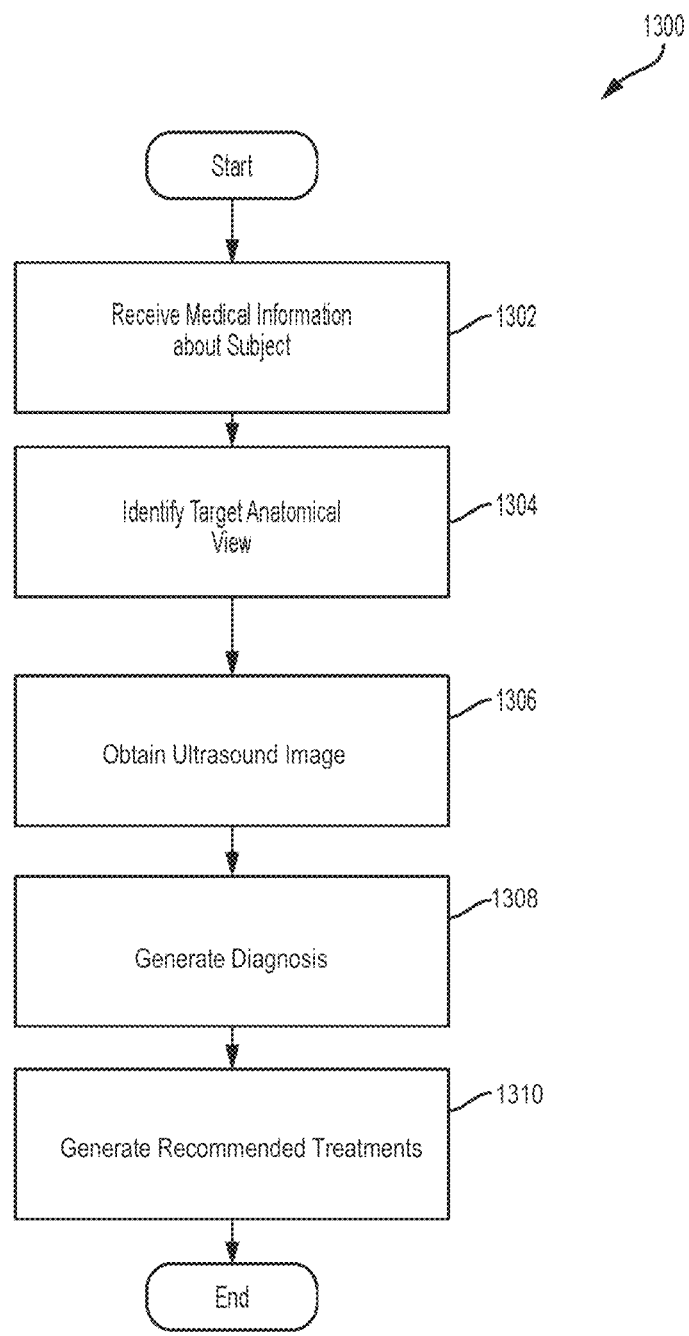
FIG. 13 shows an exemplary method of generating a diagnosis of a medical condition of a subject according to some embodiments of the disclosure.

FIG. 13 shows an example process 1300 for generating a diagnosis of a medical condition of a subject. The process 1300 may be performed by, for example, a computing device in an ultrasound system. As shown, the process 1300 comprises an act 1302 of receiving medical information about the subject, an act 1304 of identifying a target anatomical view, an act 1306 of obtaining an ultrasound image containing the target anatomical view, an act 1308 of generating a diagnosis of a medical condition of a subject, and an act 1310 of generating recommended treatments for the subject.

In act 1302, the computing device may receive medical information about the subject. Example medical information about the subject that may be received includes: a heart rate, a blood pressure, a body surface area, an age, a weight, a height, and a medication being taken by the subject. The computing device may receive the medical information by, for example, posing one or more questions to an operator and receiving a response. Additionally (or alternatively), the computing device may communicate with an external system to obtain the medical information. For example, the operator may scan a barcode (e.g., a QR code) on the ultrasound device using the computing device and the computing device may use information obtained from the barcode to access medical records associated with the subject on a remote server.

In act 1304, the computing device may identify a target anatomical view based on the received medical information. The computing device may analyze the received medical information to identify one or more organs that may be functioning abnormally. Then, the computing device may identify an anatomical view that contains the identified one or more organs. For example, the medical information about the subject may indicate that the heart of the subject is functioning abnormally (e.g., the patient has symptoms of congestive heart failure) and identify a PLAX view as the anatomical view to image.

In act 1306, the computing device may obtain an ultrasound image containing the target anatomical view. For example, the computing device may retrieve an ultrasound image of the subject containing the target anatomical view from an electronic health record of the patient. Alternatively (or additionally), the computing device may guide the operator to obtain an ultrasound image that contains the target anatomical view. For example, the computing device may issue one or more instructions regarding how the operator should position the ultrasound device on the subject to obtain an ultrasound image containing the target anatomical view. The computing device may generate and/or provide these instructions in any of a variety of ways. For example, the computing device may perform a process that is similar to (or identical to) the process 900 described above.

In act 1308, the computing device may generate a diagnosis of a medical condition of the subject using the ultrasound image containing the target anatomical view. In some embodiments, the computing device may analyze the ultrasound image containing the target anatomical view to identify one or more medical parameters (e.g., an EF of the subject) and use the identified one or more medical parameters (alone or in combination with other information such as medical information of the subject) to generate the diagnosis. In these embodiments, the computing device may perform one or more acts in process 1200 to identify a medical parameter of the subject. For example, the computing device may determine an ejection fraction of the subject by performing acts 1202, 1204, and/or 1206 and compare the resulting ejection fraction value with a threshold to determine whether the subject is likely suffering from congestive heart failure. The computing device may combine the information regarding the medical parameters with other information (such as the medical information about the subject received in act 1302) to diagnose a medical condition of the subject. For example, the computing device may diagnose a patient with congestive heart failure responsive to the computing device determining that the ejection fraction of the subject is below a threshold and that the subject has reported symptoms of congestive heart failure (such as experiencing paroxysmal nocturnal dyspnea). It should be appreciated that the computing device may be configured to diagnose any of a variety of medical conditions such as: heart conditions (e.g., congestive heart failure, coronary artery disease, and congenital heart disease), lung conditions (e.g., lung cancer), kidney conditions (e.g., kidney stones), and/or joint conditions (e.g., arthritis).

In act 1310, the computing device may generate one or more recommended treatments for the subject. The computing device may generate the one or more recommended treatments based on the diagnosis of the subject. Example recommended treatments include: a change in diet, a change in exercise routine, a pharmaceutical drug, a biologic (e.g., vaccines, gene therapies, cellular therapies), radiotherapy, chemotherapy, and surgical intervention. For example, the subject may be diagnosed with congestive heart failure and the computing device generate a recommended treatment of: angiotensin-converting-enzyme inhibitors (ACE inhibitors), angiotensin receptor blockers (ARB), or other alternatives.

It should be appreciated that the computing device may use information other than the diagnosis to generate the recommended treatment, such as medical information of the subject and/or one or more medical parameters extracted from the ultrasound image. For example, the medical information of the subject may indicate that the subject is a smoker and the computing device may include a recommended treatment of quitting smoking when the subject is diagnosed with congestive heart failure. In another example, the medical information of the subject may include one or more drug allergies of the subject and the computing device may not recommend any treatments that involve administration of a drug to which the subject is allergic. In yet another example, the medical information of the subject may include one or more drugs taken by the subject and the computing device may not recommend any treatments that would adversely interact with one or more of the drugs already taken by the subject.

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined. For example, the process 1300 of identifying an anatomical view to image based on medical information about the subject may be combined with the process 1200 for analyzing captured ultrasound images to identify a medical parameter of the subject. Thereby, the computing device may (1) identify an anatomical view to image, (2) guide the operator to capture an ultrasound image containing the anatomical view, and (3) analyze the captured ultrasound image to identify medical parameters of the subject. In this example, the ultrasound device may additionally make one or more treatment recommendations based on the identified medical parameters and/or medical information regarding the subject.

Example Deep Learning Techniques

Aspects of the technology described herein relate to the application of automated image processing techniques to analyze images, such as ultrasound images and non-acoustic images. In some embodiments, the automated image processing techniques may comprise machine learning techniques such as deep learning techniques. Machine learning techniques may comprise techniques that seek to identify patterns in a set of data points and use the identified patterns to make predictions for new data points. These machine learning techniques may involve training (and/or building) a model using a training data set to make such predictions. The trained model may be used as, for example, a classifier that is configured to receive a data point as an input and provide an indication of a class to which the data point likely belongs as an output.

Deep learning techniques may include those machine learning techniques that employ neural networks to make predictions. Neural networks typically comprise a collection of neural units (referred to as neurons) that each may be configured to receive one or more inputs and provide an output that is a function of the input. For example, the neuron may sum the inputs and apply a transfer function (sometimes referred to as an "activation function") to the summed inputs to generate the output. The neuron may apply a weight to each input to, for example, weight some inputs higher than others. Example transfer functions that may be employed include step functions, piecewise linear functions, and sigmoid functions. These neurons may be organized into a plurality of sequential layers that each comprise one or more neurons. The plurality of sequential layers may include an input layer that receives the input data for the neural network, an output layer that provides the output data for the neural network, and one or more hidden layers connected between the input and output layers. Each neuron in a hidden layer may receive inputs from one or more neurons in a previous layer (such as the input layer) and provide an output to one or more neurons in a subsequent layer (such as an output layer).

A neural network may be trained using, for example, labeled training data. The labeled training data may comprise a set of example inputs and an answer associated with each input. For example, the training data may comprise a plurality of ultrasound images that are each labeled with an anatomical view that is contained in the respective ultrasound image. In this example, the ultrasound images may be provided to the neural network to obtain outputs that may be compared with the labels associated with each of the ultrasound images. One or more characteristics of the neural network (such as the interconnections between neurons (referred to as edges) in different layers and/or the weights associated with the edges) may be adjusted until the neural network correctly classifies most (or all) of the input images.

In some embodiments, the labeled training data may comprise sample patient images are obtained that need not all be "standard" or "good" image of an anatomic structure. For example, one or more of the sample patient images may be "non-ideal" for training purposes. Each of these sample patient images may be evaluated by a trained clinician. The trained clinician may add a qualitative label to each of the sample patient images. In the specific example of a PLAX image, the clinician may determine that the given image is "normal" (i.e., depicts a good view of the structure for analysis purposes). In the alternative, if the image is not ideal, the clinician may provide a specific label for the image that describes the problem with it. For example, the image may represent an image taken because the ultrasound device was oriented "too counterclockwise" or perhaps "too clockwise" on the patient. Any number of specific errors may be assigned to a sample given image.

Once the training data has been created, the training data may be loaded to a database (e.g., an image database) and used to train a neural network using deep learning techniques. Once the neural network has been trained, the trained neural network may be deployed to one or more computing devices. It should be appreciated that the neural network may be trained with any number of sample patient images. For example, a neural network may be trained with as few as 7 or so sample patient images, although it will be appreciated that the more sample images used, the more robust the trained model data may be.

Convolutional Neural Networks

Figure 14:
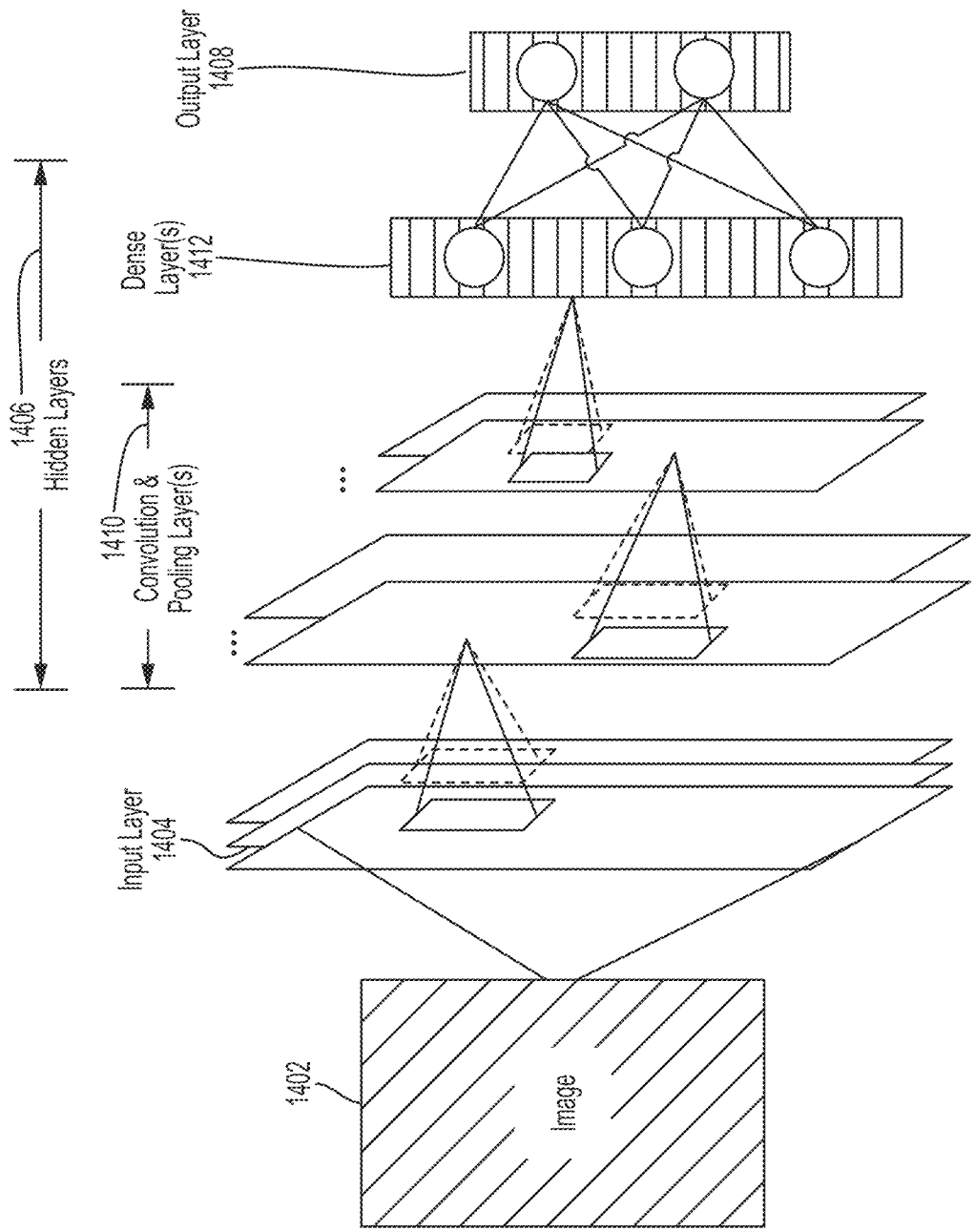
FIG. 14 shows an exemplary convolutional neural network according to some embodiments of the disclosure.

In some applications, a neural network may implemented using one or more convolution layers to form a convolutional neural network. An example convolutional neural network is shown in FIG. 14 that is configured to analyze an image 1402. As shown, the convolutional neural network comprises an input layer 1404 to receive the image 1402, an output layer 1408 to provide the output, and a plurality of hidden layers 1406 connected between the input layer 1404 and the output layer 1408. The plurality of hidden layers 1406 comprises convolution and pooling layers 1410 and dense layers 1412.

The input layer 1404 may receive the input to the convolutional neural network. As shown in FIG. 14, the input the convolutional neural network may be the image 1402. The image 1402 may be, for example, an ultrasound image or a non-acoustic image.

The input layer 1404 may be followed by one or more convolution and pooling layers 1410. A convolutional layer may comprise a set of filters that are spatially smaller (e.g., have a smaller width and/or height) than the input to the convolutional layer (e.g., the image 1402). Each of the filters may be convolved with the input to the convolutional layer to produce an activation map (e.g., a 2-dimensional activation map) indicative of the responses of that filter at every spatial position. The convolutional layer may be followed by a pooling layer that down-samples the output of a convolutional layer to reduce its dimensions. The pooling layer may use any of a variety of pooling techniques such as max pooling and/or global average pooling. In some embodiments, the down-sampling may be performed by the convolution layer itself (e.g., without a pooling layer) using striding.

The convolution and pooling layers 1410 may be followed by dense layers 1412. The dense layers 1412 may comprise one or more layers each with one or more neurons that receives an input from a previous layer (e.g., a convolutional or pooling layer) and provides an output to a subsequent layer (e.g., the output layer 1408). The dense layers 1412 may be described as "dense" because each of the neurons in a given layer may receive an input from each neuron in a previous layer and provide an output to each neuron in a subsequent layer. The dense layers 1412 may be followed by an output layer 1408 that provides the output of the convolutional neural network. The output may be, for example, an indication of which class, from a set of classes, the image 1402 (or any portion of the image 1402) belongs to.

It should be appreciated that the convolutional neural network shown in FIG. 14 is only one example implementation and that other implementations may be employed. For example, one or more layers may be added to or removed from the convolutional neural network shown in FIG. 14. Additional example layers that may be added to the convolutional neural network include: a rectified linear units (ReLU) layer, a pad layer, a concatenate layer, and an upscale layer. An upscale layer may be configured to upsample the input to the layer. An ReLU layer may be configured to apply a rectifier (sometimes referred to as a ramp function) as a transfer function to the input. A pad layer may be configured to change the size of the input to the layer by padding one or more dimensions of the input. A concatenate layer may be configured to combine multiple inputs (e.g., combine inputs from multiple layers) into a single output.

Convolutional neural networks may be employed to perform any of a variety of functions described herein. For example, a convolutional neural networks may be employed to: (1) identify an anatomical view contained in an ultrasound image, (2) identify an instruction to provide an operator, (3) identify an anatomical feature in an ultrasound image, or (4) identify a pose of ultrasound device in a non-acoustic image. It should be appreciated that more than a single convolutional neural network may be employed to perform one or more of these functions. For example, a first convolutional neural network may be employed to identify an instruction to provide an operator based on an input ultrasound image and a second, different convolutional neural network may be employed to identify an anatomical feature in an ultrasound image. The first and second neural networks may comprise a different arrangement of layers and/or be trained using different training data.

An example implementation of a convolutional network is shown below in Table 1. The convolutional neural network shown in Table 1 may be employed to classify an input image (e.g., an ultrasound image). For example, the convolutional network shown in Table 1 may be configured to receive an input ultrasound image and provide an output that is indicative of which instruction from a set of instructions should be provided to an operator to properly position the ultrasound device. The set of instructions may include: (1) tilt the ultrasound device inferomedially, (2) rotate the ultrasound device counterclockwise, (3) rotate the ultrasound device clockwise, (4) move the ultrasound device one intercostal space down, (5) move the ultrasound device one intercostal space up, and (6) slide the ultrasound device medially. In Table 1, the sequence of the layer is denoted by the "Layer Number" column, the type of the layer is denoted by the "Layer Type" column, and the input to the layer is denoted by the "Input to Layer" column.

TABLE 1

Example Layer Configuration for Convolutional neural network

| Layer Number | Layer Type | Input to Layer |
| --- | --- | --- |
| 1 | Input Layer | Input Image |
| 2 | Convolution Layer | Output of Layer 1 |
| 3 | Convolution Layer | Output of Layer 2 |
| 4 | Pooling Layer | Output of Layer 3 |
| 5 | Convolution Layer | Output of Layer 4 |
| 6 | Convolution Layer | Output of Layer 5 |
| 7 | Pooling Layer | Output of Layer 6 |
| 8 | Convolution Layer | Output of Layer 7 |
| 9 | Convolution Layer | Output of Layer 8 |
| 10 | Pooling Layer | Output of Layer 9 |
| 11 | Convolution Layer | Output of Layer 10 |
| 12 | Convolution Layer | Output of Layer 11 |
| 13 | Pooling Layer | Output of Layer 12 |
| 14 | Fully Connected Layer | Output of Layer 13 |
| 15 | Fully Connected Layer | Output of Layer 14 |
| 16 | Fully Connected Layer | Output of Layer 15 |

Another example implementation of a convolutional neural network is shown below in Table 2. The convolutional neural network in Table 2 may be employed to identify two points on the basal segments of the left ventricle in an ultrasound image. In Table 2, the sequence of the layer is denoted by the "Layer Number" column, the type of the layer is denoted by the "Layer Type" column, and the input to the layer is denoted by the "Input to Layer" column.

TABLE 2

Example Layer Configuration for Convolutional neural network

| Layer Number | Layer Type | Input to Layer |
| --- | --- | --- |
| 1 | Input Layer | Input Image |
| 2 | Convolution Layer | Output of Layer 1 |
| 3 | Convolution Layer | Output of Layer 2 |
| 4 | Pooling Layer | Output of Layer 3 |
| 5 | Convolution Layer | Output of Layer 4 |
| 6 | Convolution Layer | Output of Layer 5 |
| 7 | Pooling Layer | Output of Layer 6 |
| 8 | Convolution Layer | Output of Layer 7 |
| 9 | Convolution Layer | Output of Layer 8 |
| 10 | Pooling Layer | Output of Layer 9 |
| 11 | Convolution Layer | Output of Layer 10 |
| 12 | Convolution Layer | Output of Layer 11 |
| 13 | Convolution Layer | Output of Layer 12 |
| 14 | Fully Connected Layer | Output of Layer 13 |
| 15 | Fully Connected Layer | Output of Layer 14 |
| 16 | Fully Connected Layer | Output of Layer 15 |

Yet another example implementation of convolutional neural network is shown below in Table 3. The convolutional neural network shown in Table 3 may be configured to receive an ultrasound image and classify each pixel in the input image as belonging to the foreground (anatomical structure, e.g., left ventricle) or to the background. Relative to the convolutional neural networks shown in Tables 1 and 2, upsampling layers have been introduced to increase the resolution of the classification output. The output of the upsampled layers is combined with the output of other layers to provide accurate classification of individual pixels. In Table 3, the sequence of the layer is denoted by the "Layer Number" column, the type of the layer is denoted by the "Layer Type" column, and the input to the layer is denoted by the "Input to Layer" column.

TABLE 3

Example Layer Configuration for Convolutional neural network

| Layer Number | Layer Type | Input to Layer |
|---|---|---|
| 1 | Input Layer | Input Image |
| 2 | Convolution Layer | Output of Layer 1 |
| 3 | Convolution Layer | Output of Layer 2 |
| 4 | Pooling Layer | Output of Layer 3 |
| 5 | Convolution Layer | Output of Layer 4 |
| 6 | Convolution Layer | Output of Layer 5 |
| 7 | Pooling Layer | Output of Layer 6 |
| 8 | Convolution Layer | Output of Layer 7 |
| 9 | Convolution Layer | Output of Layer 8 |
| 10 | Pooling Layer | Output of Layer 9 |
| 11 | Convolution Layer | Output of Layer 10 |
| 12 | Convolution Layer | Output of Layer 11 |
| 13 | Convolution Layer | Output of Layer 12 |
| 14 | Upscale Layer | Output of Layer 13 |
| 15 | Convolution Layer | Output of Layer 14 |
| 16 | Pad Layer | Output of Layer 15 |
| 17 | Concatenate Layer | Output of Layers 9 and 16 |
| 18 | Convolution Layer | Output of Layer 17 |
| 19 | Convolution Layer | Output of Layer 18 |
| 20 | Upscale Layer | Output of Layer 19 |
| 21 | Convolution Layer | Output of Layer 20 |
| 22 | Pad Layer | Output of Layer 21 |
| 23 | Concatenate Layer | Output of Layers 6 and 22 |
| 24 | Convolution Layer | Output of Layer 23 |
| 25 | Convolution Layer | Output of Layer 24 |
| 26 | Upscale Layer | Output of Layer 25 |
| 27 | Convolution Layer | Output of Layer 26 |
| 28 | Pad Layer | Output of Layer 27 |
| 29 | Concatenate Layer | Output of Layers 3 and 28 |
| 30 | Convolution Layer | Output of Layer 29 |
| 31 | Convolution Layer | Output of Layer 30 |
| 32 | Convolution Layer | Output of Layer 31 |

Integrating Statistical Knowledge into Convolutional Neural Networks

In some embodiments, statistical prior knowledge may be integrated into a convolutional neural network. For example, prior statistical knowledge, obtained through principal components analysis (PCA), may be integrated into a convolutional neural network in order to obtain robust predictions even when dealing with corrupted or noisy data. In these embodiments, the network architecture may be trained end-to-end and include a specially designed layer which incorporates the dataset modes of variation discovered via PCA and produces predictions by linearly combining them. Further, a mechanism may be included to focus the attention of the convolutional neural network on specific regions of interest of an input image in order to obtain refined predictions.

The complexity of anatomical structures along with the presence of noise, artifacts, visual clutter, and poorly defined image areas often cause ambiguities and errors in image analysis. In the medical domain, many of these errors can be resolved by relying on statistical prior knowledge. For example, in segmentation it is useful to incorporate prior knowledge about the segmentation contour. Landmark localization tasks can benefit from the semantic relationships between different landmarks and how their positions are allowed to change with respect to each other. Finally, statistical models capturing the appearance of selected regions have been shown to improve results in a number of cases.

Shape models have also been used to constrain segmentation algorithms that are based on machine learning. This has been done by learning a posterior distribution of PCA coefficients and by re-projecting portions of ground truth contours onto unseen examples. These models rely on shallow architectures, manually engineered or learned features and shape constraints being imposed as part of a regularization or post-processing step.

Deep learning approaches and convolutional neural networks in particular, have shown astonishing capabilities to learn a hierarchy of features directly from raw data. Deep learning models are organized in multiple layers, where features are extracted in a cascaded fashion. As the depth of the network increases, the extracted features refer to bigger image regions and therefore recognize higher level concepts compared to the ones extracted in earlier layers.

Unfortunately, the applicability of deep learning approaches in medical image analysis is often limited by the requirement to train with large annotated datasets. Supplying more annotated data during the learning process allows a larger amount of challenging, real-world situations to be captured and therefore partly overcomes the difficulty to integrate prior statistical knowledge in the learning process. In the medical domain, it is often difficult to obtain large annotated datasets due to limitations on data usage and circulation and the tediousness of the annotation process. Moreover, medical images typically exhibit large variability in the quality and appearance of the structures across different scans, which further hampers the performances of machine vision algorithms. Ultrasound images, in particular, are often corrupted by noise, shadows, signal drop regions, and other artifacts that make their interpretation challenging even to human observers. Additionally, ultrasound scans exhibit high intra- and inter-operator acquisition variability, even when scanned by experts.

In some embodiments, PCA may be employed to advantageously discover the principal modes of variation of training data. Such discovered principle modes of variation may be integrated into a convolutional neural network. The robustness of the results is increased by constraining the network predictions with prior knowledge extracted by statistically analyzing the training data. This approach makes it possible to process cases where the anatomy of interest appears only partially, its appearance is not clear, or it visually differs from the observed training examples.

A convolutional network architecture may be employed that includes a new PCA layer that incorporates the dataset modes of variation and produces predictions as a linear combination of the modes. This process is used in procedure that focuses the attention of the subsequent convolutional neural network layers on the specific region of interest to obtain refined predictions. Importantly, the network is trained end-to-end with the shape encoded in a PCA layer and the loss imposed on the final location of the points. The end-to-end training makes it possible to start from a random configuration of network parameters and find the optimal set of filters and biases according to the estimation task and training data. This method may be applied to, for example, the landmark localization in 2D echocardiography images acquired from the parasternal long axis view and to the left ventricle segmentation of the heart in scans acquired from the apical four chamber view.

Incorporating statistical prior knowledge obtained through PCA into a convolutional neural network may advantageously overcome the limitations of previous deep learning approaches which lack strong shape priors and the limitations of active shape models which lack advanced pattern recognition capabilities. This approach may be fully automatic and therefore differs from most previous methods based on ASM which required human interaction. The neural network outputs the prediction in a single step without requiring any optimization loop.

In some embodiments, a training set containing N images and the associated ground truth annotations consisting of coordinates referring to P key-points which describe the position of landmarks may be employed. The training set may be used to first obtain the principal modes of variation of the coordinates in Y and then train a convolutional neural network that leverages it. The information used to formulate our predictions is obtained after multiple convolution and pooling operations and therefore fine-grained, high-resolution details might be lost across the layers. For this reason, a mechanism may be employed that focuses the attention of the network on full-resolution details by cropping portions of the image in order to refine the predictions. The architecture may be trained end-to-end, and all the parameters of the network may be updated at every iteration.

Much of the variability of naturally occurring structures, such as organs and anatomical details of the body, is not arbitrary. By simple observation of a dataset of shapes representative of a population, for example, one can notice the presence of symmetries and correlations between different shape parts. In the same way, it is often possible to observe correlations in the position of different landmarks of the body since they are tightly entangled with each other. PCA can be used to discover the principal modes of variation of the dataset at hand. When shapes are described as aligned point sets across the entire dataset, PCA reveals what correlations exist between different points and defines a new coordinates frame where the principal modes of variation correspond to the axes. Having a matrix Y containing the dataset, where each observation $y_i$ constitutes one of its columns, its principal components may be obtained by first de-meaning Y through equation (3):

$$\tilde{Y} = Y - \mu, \text{ with } \mu = \frac{1}{N}\sum_i y_i \quad (3)$$

and then by computing the eigenvectors of the covariance matrix $\tilde{Y}\tilde{Y}^T$. This corresponds to U in equation (4):

$$\tilde{Y} = U\Sigma V^T \quad (4)$$

Which is obtained via singular value decomposition (SVD). The matrix $\tilde{Y}=U\Sigma V^T$ is diagonal and contains the eigenvalues of the covariance matrix and represent the variance associated with each principle component in the eigenbase.

Any example in the dataset can be synthesized as a linear combination of the principle components as shown in Equation (5):

$$y_i = Uw + \mu \quad (5)$$

Each coefficient of the linear combination governs not only the position of one, but multiple correlated points that may describe the shape at hand. Imposing constraints on the coefficients weighting the effect of each principal component, or reducing their number until the correct balance between percent-age of retained variance and number of principal components is reached, it is possible to synthesize shapes that respect the concept of "legal shape" introduced before.

The convolutional neural network may not be trained to perform regression on the weights w in Equation 5. Instead, an end-to-end architecture may be used where the network directly uses the PCA eigenbase to make predictions from an image in the form of key-points locations. This has direct consequences on the training process. The network learns, by minimizing the loss, to steer the coefficients while being "aware" of their effect on the results. Each of the weights controls the location of multiple correlated key-points simultaneously. Since the predictions are obtained as a linear combination of the principal components, they obey the concept of "legal shape" and therefore are more robust to missing data, noise, and artifacts.

The network may comprises two branches. The first branch employs convolutional, pooling, and dense layers, and produces a coarse estimate of the key-point locations via PCA. The second branch operates on full resolution patches cropped from the input image around the coarse key-point locations. The output of the second network refines the predictions made by the first by using more fine-grained visual information. Both the branches are trained simultaneously and are fully differentiable. The convolutions are all applied without padding and they use kernels of size 3×3 in the first convolutional neural network branch and 5×5 in the second, shallower, branch. The nonlinearities used throughout the network are rectified linear functions. All the inputs of the PCA layer, are not processed through nonlinearities.

The PCA layer implements a slightly modified of the synthesis equation in 5. In addition to the weights w, which are supplied by a dense layer of the network, a global shift s that is applied to all the predicted points is also supplied. Through the bi-dimensional vector s, translations of the anatomy of interest are able to be handled. With a slight abuse of notation, Equation 5 may be re-written as shown in Equation (6):

$$y_i = Uw + \mu + s \quad (6)$$

The layer performing cropping follows an implementation inspired to spatial transformers which ensures differentiability. A regular sampling pattern is translated to the coarse key-point locations and the intensity values of the surrounding area are sampled using bilinear interpolation. Having P key-points, P patches may be obtained for each of the K images in the mini-batch. The resulting KP patches are then processed through a 3-layers deep convolutional neural network using 8 filters applied without padding, which reduces their size by a total of 12 pixels. After the convolution layers, the patches are again arranged into a batch of K elements having P×8 channels, and further processed through three dense layers, which ultimately compute $w_A$ having the same dimensionality of w. The refined weights $w_F$ which are employed in the PCA layer to obtain a more accurate key-point prediction, are obtained as $w_F = w_A + w$.

This approach has been tested on two different ultrasound dataset depicting the human heart with the aim to solve two different tasks with good results. The first task is segmentation of the left ventricle (LV) of the heart form scans acquired from the apical view, while the second task is a landmark localization problem where the aim is to localize 14 points of interest in images acquired from the parasternal long axis view. In the first case, the model leverages prior statistical knowledge relative to the shape of the structures of interest, while in the second case the model captures the spatiotemporal relationships between landmarks across cardiac cycles of different patients. For the segmentation task a total of 1100 annotated images, 953 for training and 147 for testing, were employed.

Techniques for Landmark Localization Using Convolutional Neural Networks

The inventors have appreciated that accurate landmark localization in ultrasound video sequences is challenging due to noise, shadows, anatomical differences, and scan plane variation. Accordingly, the inventors have conceived and developed a fully convolutional neural network trained to regress the landmark locations that may address such challenges. In this convolutional neural network, a series of convolution and pooling layers is followed by a collection of upsampling and convolution layers with feature forwarding from the earlier layers. The final location estimates are produced by computing a center of mass of the regression maps in the last layer. In addition, uncertainty of the estimates are computed as the standard deviations of the predictions. The temporal consistency of the estimates is achieved by a Long Short-Term memory cells which processes several previous frames in order to refine the estimate in the current frame. The results on automatic measurement of left ventricle in parasternal long axis views and subsequent ejection fraction computation show accuracy on par with inter-user variability.

Regression modeling is an approach for describing relationship between an independent variable and one or more dependent variables. In machine learning, this relationship is described by a function whose parameters are learned from training examples. In deep learning models, this function is a composition of logistic (sigmoid), hyperbolic tangent, or more recently rectified linear functions at each layer of the network. In many applications, the function learns a mapping between input image patches and a continuous prediction variable.

Regression modeling has been used to detect organ or landmark locations in images, visually track objects and features, and estimate body poses. The deep learning approaches have outperformed previous techniques especially when a large annotated training data set is available. The proposed architectures used cascade of regressors, refinement localization stages, and combining cues from multiple landmarks to localize landmarks. In medical images, the requirements on accurate localization are high since the landmarks are used as measurement points to help in diagnosis. When tracking the measurements in video sequences, the points must be accurately detected in each frame while ensuring temporal consistency of the detections.

A fully convolutional network architecture for accurate localization of anatomical landmark points in video sequences has been devised. The advantage of the fully convolutional network is that the responses from multiple windows covering the input image can be computed in a single step. The network is trained end-to-end and outputs the locations of the landmarks. The aggregation of the regressed locations at the last convolution layer is ensured by a new center-of-mass layer which computes mean position of the predictions. The layer makes it possible to use new regularization technique based on variance of the predicted candidates and to define new loss based on relative locations of landmarks. The evaluation is fast to process each frame of a video sequence at near frame rate speeds. The temporal consistency of the measurements is improved by Convolutional Long Short-term Memory (CLSTM) cells which process the feature maps from several previous frames and produce updated features for the current frame in order to refine the estimate.

Denote an input image of width w and height h as I (independent variable) and the position of k landmarks stacked columnwise into p (dependent variable). The goal of the regression is to learn a function $f(I; \theta)=p$ parametrized by $\theta$. $f$ may be approximated by a convolutional neural network and train the parameters params using a database of images and their corresponding annotations. Typically, a Euclidean loss is employed to train $f$ using each annotated image.

Previously, regression estimates were obtained directly from the last layer of the network, which was fully connected to previous layer. This is a highly non-linear mapping, where the estimate is computed from the fully connected layers after convolutional blocks. Instead of fully connected network, we propose to regress landmark locations using a fully convolutional architecture (FCNN). Their advantage is that the estimates can be computed in a single evaluation step. In the proposed architecture, landmark coordinate estimates may be obtained at each image location.

The aggregated landmark coordinate estimates are computed in a new center of mass layer from input at each predicting location $l_{ij}$:

$$\hat{p} = \frac{1}{w \times h} \sum_{i=1}^{h} \sum_{j=1}^{w} I_{ij} \quad (7)$$

Recurrent neural networks (RNN) can learn sequential context dependencies by accepting input $x_t$ and updating a hidden vector $h_t$ at every time step t. The RNN network can be composed of Long-short Term Memory (LSTM) units, each controlled by a gating mechanism with three types of updates, $i_t$, $f_t$, $o_t$ that range between 0 and 1. The value $i_t$ controls the update of each memory cell, $f_t$ controls the forgetting of each memory cell, and $o_t$ controls the influence of the memory state on the hidden vector. In Convolutional LSTMs (CLSTMs), the input weights and hidden vector weights are convolved instead of multiplied to model spatial constraints. The function introduces a non-linearity, which may be chosen to be tanh. Denoting the convolutional operator as * for equations 8-10, the values at the gates are computed as follows:

$$\text{forget gate: } f_t = \text{sigm}(W_f * [h_{t-1}, x_t] + b_f) \quad (8)$$

$$\text{input gate: } i_t = \text{sigm}(W_i * [h_{t-1}, x_t] + b_i) \quad (9)$$

$$\text{output gate: } o_t = \text{sigm}(W_o * [h_{t-1}, x_t] + b_o) \quad (10)$$

The parameters of the weights W and biases b are learned from training sequences. In addition to the gate values, each CLSTM unit computes state candidate values:

$$g_t = \tanh(W_g * [h_{t-1}, x_t] + b_g) \quad (11)$$

where $g_t$ ranges between −1 and 1 and influences memory contents. The memory cell is updated by $$c_t = f_t \odot c_{t-1} + i_t \odot g_t \quad (12)$$

which additively modifies each memory cell. The update process results in the gradients being distributed during backpropagation. The symbol denotes the Hadamard product. Finally, the hidden state is updated as:

$$h_t = o_t \odot \tanh(c_t) \quad (13)$$

In sequential processing of image sequences, the inputs into the LSTM consist of the feature maps computed from a convolutional neural network. In this work, two architectures are proposed to compute the feature maps. The first architecture is a neural network with convolution and pooling layers. After sequential processing the feature maps in CLSTM, the output is fed into fully connected layers to compute the landmark location estimate. In the second architecture, the CLSTM inputs is the final layer of a convolutional path of the fully convolutional architecture (FCN). The landmark location estimates are computed from the CLSTM output processed through the transposed convolutional part of the FCN network.

Example Ultrasound Systems

Figure 15A:
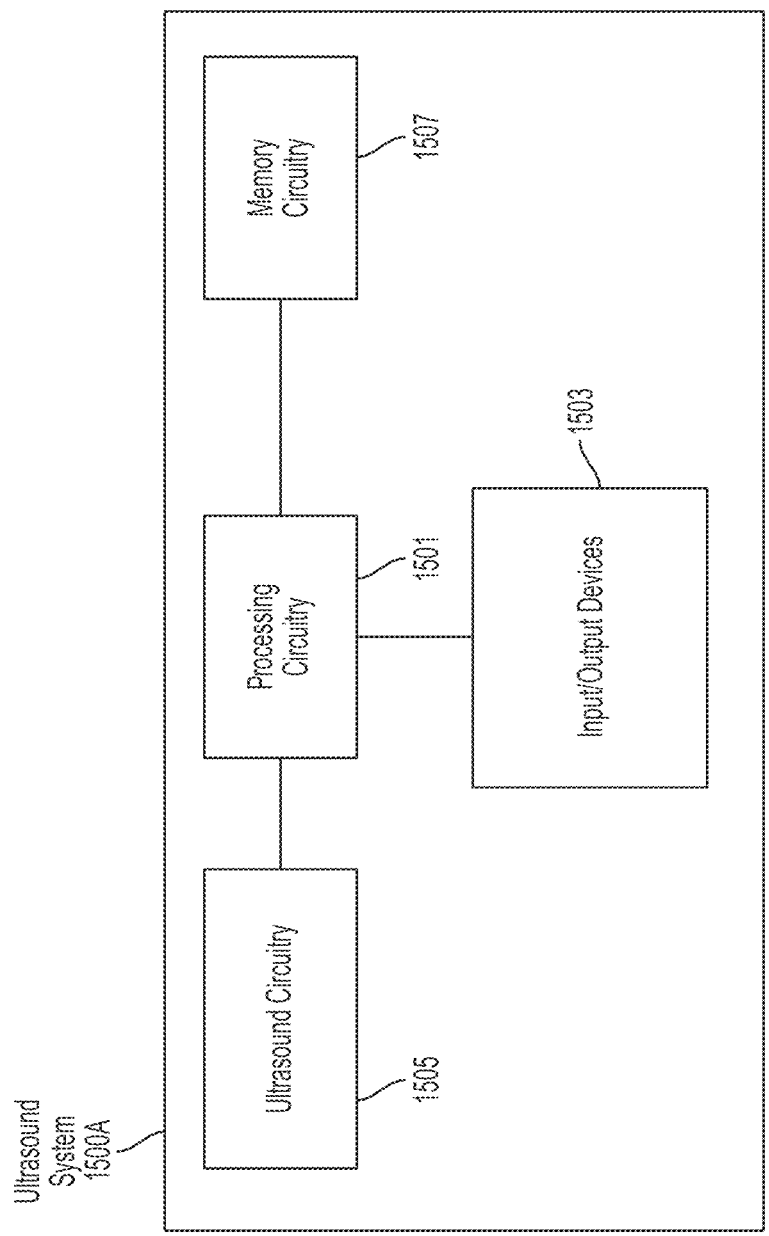
FIG. 15A shows a block diagram of an exemplary ultrasound system according to some embodiments of the disclosure.

FIG. 15A is a schematic block diagram illustrating aspects of an example ultrasound system 1500A upon which various aspects of the technology described herein may be practiced. For example, one or more components of the ultrasound system 1500A may perform any of the processes described herein. As shown, the ultrasound system 1500A comprises processing circuitry 1501, input/output devices 1503, ultrasound circuitry 1505, and memory circuitry 1507.

The ultrasound circuitry 1505 may be configured to generate ultrasound data that may be employed to generate an ultrasound image. The ultrasound circuitry 1505 may comprise one or more ultrasonic transducers monolithically integrated onto a single semiconductor die. The ultrasonic transducers may include, for example, one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the ultrasonic transducers may be formed the same chip as other electronic components in the ultrasound circuitry 1505 (e.g., transmit circuitry, receive circuitry, control circuitry, power management circuitry, and processing circuitry) to form a monolithic ultrasound device.

The processing circuitry 1501 may be configured to perform any of the functionality described herein. The processing circuitry 1501 may comprise one or more processors (e.g., computer hardware processors). To perform one or more functions, the processing circuitry 1501 may execute one or more processor-executable instructions stored in the memory circuitry 1507. The memory circuitry 1507 may be used for storing programs and data during operation of the ultrasound system 1500B. The memory circuitry 1507 may comprise one or more storage devices such as non-transitory computer-readable storage media. The processing circuitry 1501 may control writing data to and reading data from the memory circuitry 1507 in any suitable manner.

In some embodiments, the processing circuitry 1501 may comprise specially-programmed and/or special-purpose hardware such as an application-specific integrated circuit (ASIC). For example, the processing circuitry 1501 may comprise one or more tensor processing units (TPUs). TPUs may be ASICs specifically designed for machine learning (e.g., deep learning). The TPUs may be employed to, for example, accelerate the inference phase of a neural network.

The input/output (I/O) devices 1503 may be configured to facilitate communication with other systems and/or an operator. Example I/O devices that may facilitate communication with an operator include: a keyboard, a mouse, a trackball, a microphone, a touch screen, a printing device, a display screen, a speaker, and a vibration device. Example I/O devices that may facilitate communication with other systems include wired and/or wireless communication circuitry such as BLUETOOTH, ZIGBEE, WiFi, and/or USB communication circuitry.

It should be appreciated that the ultrasound system 1500A may be implemented using any number of devices. For example, the components of the ultrasound system 1500A may be integrated into a single device. In another example, the ultrasound circuitry 1505 may be integrated into an ultrasound device that is communicatively coupled with a computing device that comprises the processing circuitry 1501, the input/output devices 1503, and the memory circuitry 1507.

Figure 15B:
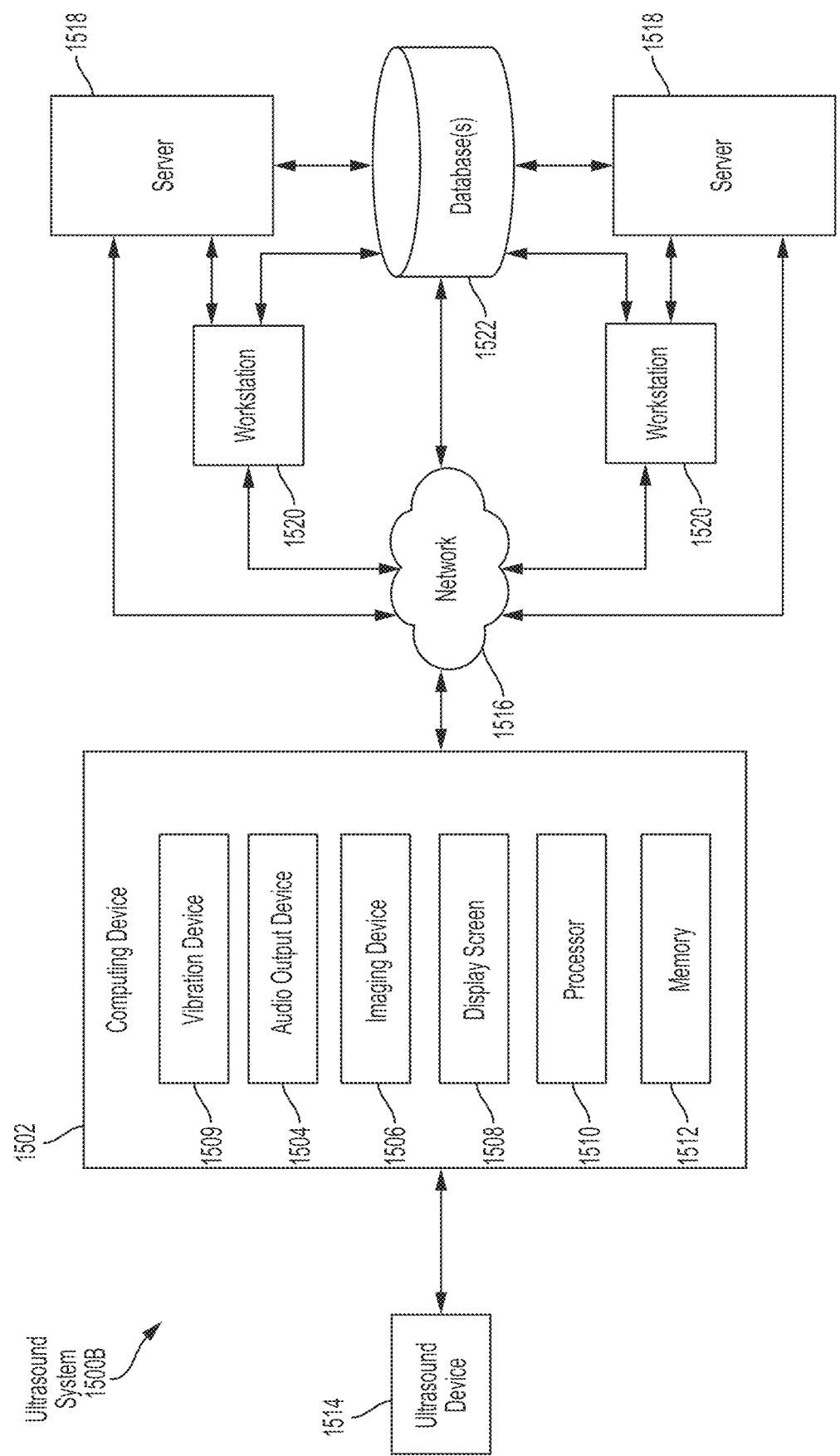
FIG. 15B shows a block diagram of another exemplary ultrasound system according to some embodiments of the disclosure.

FIG. 15B is a schematic block diagram illustrating aspects of another example ultrasound system 1500B upon which various aspects of the technology described herein may be practiced. For example, one or more components of the ultrasound system 1500B may perform any of the processes described herein. As shown, the ultrasound system 1500B comprises an ultrasound device 1514 in wired and/or wireless communication with a computing device 1502. The computing device 1502 comprises an audio output device 1504, an imaging device 1506, a display screen 1508, a processor 1510, a memory 1512, and a vibration device 1509. The computing device 1502 may communicate with one or more external devices over a network 1516. For example, the computing device 1502 may communicate with one or more workstations 1520, servers 1518, and/or databases 1522.

The ultrasound device 1514 may be configured to generate ultrasound data that may be employed to generate an ultrasound image. The ultrasound device 1514 may be constructed in any of a variety of ways. In some embodiments, the ultrasound device 1514 includes a transmitter that transmits a signal to a transmit beamformer which in turn drives transducer elements within a transducer array to emit pulsed ultrasonic signals into a structure, such as a patient. The pulsed ultrasonic signals may be back-scattered from structures in the body, such as blood cells or muscular tissue, to produce echoes that return to the transducer elements. These echoes may then be converted into electrical signals, or ultrasound data, by the transducer elements and the electrical signals are received by a receiver. The electrical signals representing the received echoes are sent to a receive beamformer that outputs ultrasound data.

The computing device 1502 may be configured to process the ultrasound data from the ultrasound device 1514 to generate ultrasound images for display on the display screen 1508. The processing may be performed by, for example, the processor 1510. The processor 1510 may also be adapted to control the acquisition of ultrasound data with the ultrasound device 1514. The ultrasound data may be processed in real-time during a scanning session as the echo signals are received. In some embodiments, the displayed ultrasound image may be updated a rate of at least 5 Hz, at least 10 Hz, at least 20 Hz, at a rate between 5 and 60 Hz, at a rate of more than 20 Hz. For example, ultrasound data may be acquired even as images are being generated based on previously acquired data and while a live ultrasound image is being displayed. As additional ultrasound data is acquired, additional frames or images generated from more-recently acquired ultrasound data are sequentially displayed. Additionally, or alternatively, the ultrasound data may be stored temporarily in a buffer during a scanning session and processed in less than real-time.

Additionally (or alternatively), the computing device 1502 may be configured to perform any of the processes described herein (e.g., using the processor 1510) and/or display any of the user interfaces described herein (e.g., using the display screen 1508). For example, the computing device 1502 may be configured to provide instructions to an operator of the ultrasound device 1514 to assist the operator select a target anatomical view of a subject to image and to guide the operator capture an ultrasound image containing the target anatomical view. As shown, the computing device 1502 may comprise one or more elements that may be used during the performance of such processes. For example, the computing device 1502 may comprise one or more processors 1510 (e.g., computer hardware processors) and one or more articles of manufacture that comprise non-transitory computer-readable storage media such as the memory 1512. The processor 1510 may control writing data to and reading data from the memory 1512 in any suitable manner. To perform any of the functionality described herein, the processor 1510 may execute one or more processor-executable instructions stored in one or more non-transitory computer-readable storage media (e.g., the memory 1512), which may serve as non-transitory computer-readable storage media storing processor-executable instructions for execution by the processor 1510.

In some embodiments, the computing device 1502 may comprise one or more input and/or output devices such as the audio output device 1504, the imaging device 1506, the display screen 1508, and the vibration device 1509. The audio output device 1504 may be a device that is configured to emit audible sound such as a speaker. The imaging device 1506 may be configured to detect light (e.g., visible light) to form an image such as a camera. The display screen 1508 may be configured to display images and/or videos such as a liquid crystal display (LCD), a plasma display, and/or an organic light emitting diode (OLED) display. The vibration device 1509 may be configured to vibrate one or more components of the computing device 1502 to provide tactile feedback. These input and/or output devices may be communicatively coupled to the processor 1510 and/or under the control of the processor 1510. The processor 1510 may control these devices in accordance with a process being executed by the process 1510 (such as any of the processes shown in FIGS. 9-13). For example, the processor 1510 may control the display screen 1508 to display any of the above described user interfaces, instructions, and/or ultrasound images. Similarly, the processor 1510 may control the audio output device 1504 to issue audible instructions and/or control the vibration device 1509 to change an intensity of tactile feedback (e.g., vibration) to issue tactile instructions. Additionally (or alternatively), the processor 1510 may control the imaging device 1506 to capture non-acoustic images of the ultrasound device 1514 being used on a subject to provide an operator of the ultrasound device 1514 an augmented reality interface (e.g., as shown in FIGS. 5B and 6).

It should be appreciated that the computing device 1502 may be implemented in any of a variety of ways. For example, the computing device 1502 may be implemented as a handheld device such as a mobile smartphone or a tablet. Thereby, an operator of the ultrasound device 1514 may be able to operate the ultrasound device 1514 with one hand and hold the computing device 1502 with another hand. In other examples, the computing device 1502 may be implemented as a portable device that is not a handheld device such as a laptop. In yet other examples, the computing device 1502 may be implemented as a stationary device such as a desktop computer.

In some embodiments, the computing device 1502 may communicate with one or more external devices via the network 1516. The computing device 1502 may be connected to the network 1516 over a wired connection (e.g., via an Ethernet cable) and/or a wireless connection (e.g., over a WiFi network). As shown in FIG. 15B, these external devices may include servers 1518, workstations 1520, and/or databases 1522. The computing device 1502 may communicate with these devices to, for example, off-load computationally intensive tasks. For example, the computing device 1502 may send an ultrasound image over the network 1516 to the server 1518 for analysis (e.g., to identify an anatomical feature in the ultrasound image and/or identify an instruction to provide the operator) and receive the results of the analysis from the server 1518. Additionally (or alternatively), the computing device 1502 may communicate with these devices to access information that is not available locally and/or update a central information repository. For example, the computing device 1502 may access the medical records of a subject being imaged with the ultrasound device 1514 from a file stored in the database 1522. In this example, the computing device 1502 may also provide one or more captured ultrasound images of the subject to the database 1522 to add to the medical record of the subject.

The terms "program," "application," or "software" are used herein in a generic sense to refer to any type of computer code or set of processor-executable instructions that may be employed to program a computer or other processor to implement various aspects of embodiments as discussed above. Additionally, according to one aspect, one or more computer programs that when executed perform methods of the disclosure provided herein need not reside on a single computer or processor, but may be distributed in a modular fashion among different computers or processors to implement various aspects of the disclosure provided herein.

Processor-executable instructions may be in many forms, such as program modules, executed by one or more computers or other devices. Generally, program modules include routines, programs, objects, components, data structures, etc. that perform particular tasks or implement particular abstract data types. Typically, the functionality of the program modules may be combined or distributed.

Also, data structures may be stored in one or more non-transitory computer-readable storage media in any suitable form. For simplicity of illustration, data structures may be shown to have fields that are related through location in the data structure. Such relationships may likewise be achieved by assigning storage for the fields with locations in a non-transitory computer-readable medium that convey relationship between the fields. However, any suitable mechanism may be used to establish relationships among information in fields of a data structure, including through the use of pointers, tags or other mechanisms that establish relationships among data elements.

Example Ultrasound Devices

Figure 16:
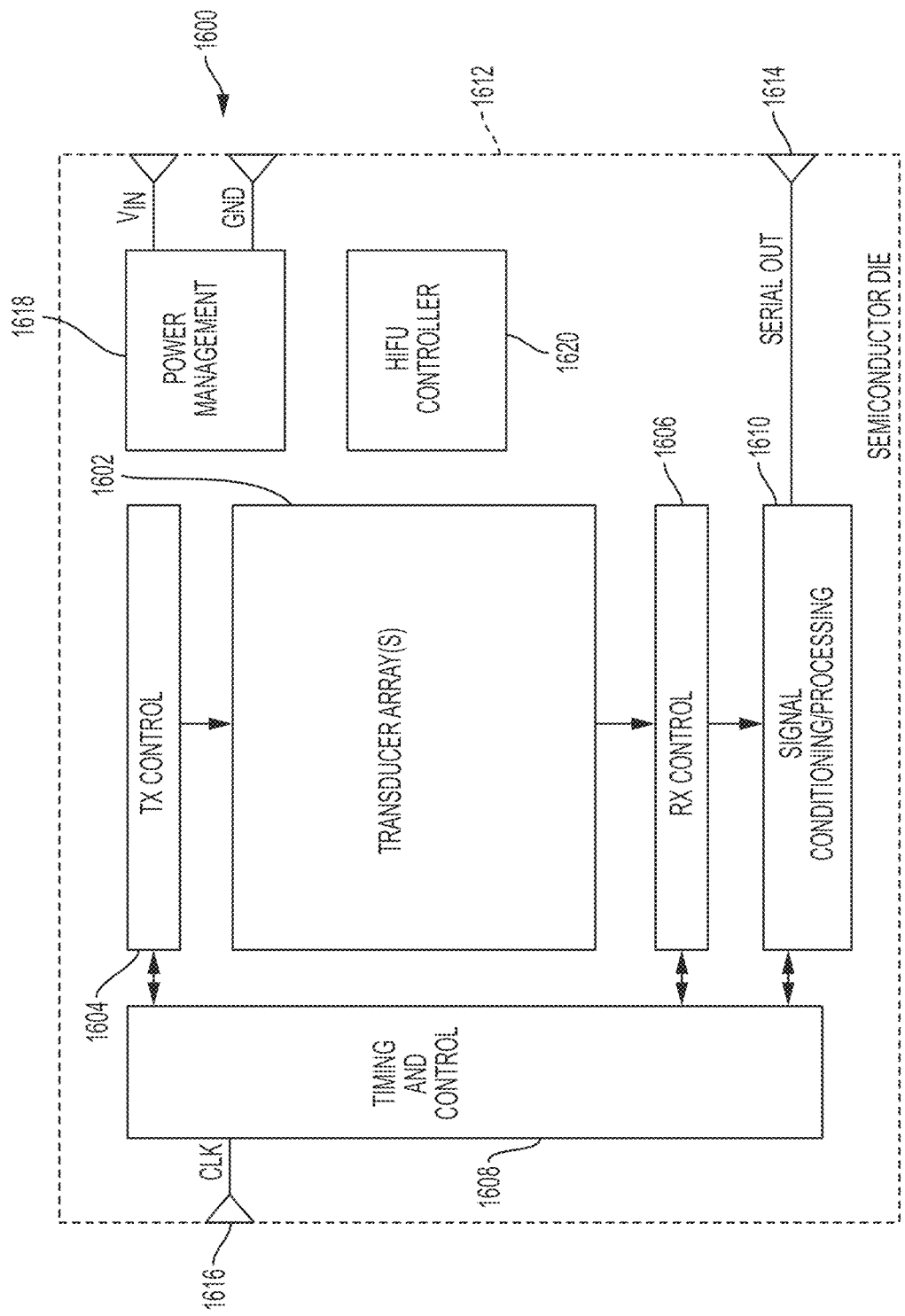
FIG. 16 shows a block diagram of an exemplary ultrasound device according to some embodiments of the disclosure.

FIG. 16 shows an illustrative example of a monolithic ultrasound device 1600 that may be employed as any of the ultrasound devices described above such as ultrasound devices 102, 502, 602, and 1514 or any of the ultrasound circuitry described herein such as ultrasound circuitry 1505. As shown, the ultrasound device 1600 may include one or more transducer arrangements (e.g., arrays) 1602, transmit (TX) circuitry 1604, receive (RX) circuitry 1606, a timing and control circuit 1608, a signal conditioning/processing circuit 1610, a power management circuit 1618, and/or a high-intensity focused ultrasound (HIFU) controller 1620. In the embodiment shown, all of the illustrated elements are formed on a single semiconductor die 1612. It should be appreciated, however, that in alternative embodiments one or more of the illustrated elements may be instead located off-chip. In addition, although the illustrated example shows both TX circuitry 1604 and RX circuitry 1606, in alternative embodiments only TX circuitry or only RX circuitry may be employed. For example, such embodiments may be employed in a circumstance where one or more transmission-only devices 1600 are used to transmit acoustic signals and one or more reception-only devices 1600 are used to receive acoustic signals that have been transmitted through or reflected off of a subject being ultrasonically imaged.

It should be appreciated that communication between one or more of the illustrated components may be performed in any of numerous ways. In some embodiments, for example, one or more high-speed busses (not shown), such as that employed by a unified Northbridge, may be used to allow high-speed intra-chip communication or communication with one or more off-chip components.

The one or more transducer arrays 1602 may take on any of numerous forms, and aspects of the present technology do not necessarily require the use of any particular type or arrangement of transducer cells or transducer elements. Indeed, although the term "array" is used in this description, it should be appreciated that in some embodiments the transducer elements may not be organized in an array and may instead be arranged in some non-array fashion. In various embodiments, each of the transducer elements in the array 1602 may, for example, include one or more capacitive micromachined ultrasonic transducers (CMUTs), one or more CMOS ultrasonic transducers (CUTs), one or more piezoelectric micromachined ultrasonic transducers (PMUTs), and/or one or more other suitable ultrasonic transducer cells. In some embodiments, the transducer elements of the transducer array 102 may be formed on the same chip as the electronics of the TX circuitry 1604 and/or RX circuitry 1606. The transducer elements 1602, TX circuitry 1604, and RX circuitry 1606 may, in some embodiments, be integrated in a single ultrasound device. In some embodiments, the single ultrasound device may be a handheld device. In other embodiments, the single ultrasound device may be embodied in a patch that may be coupled to a patient. The patch may be configured to transmit, wirelessly, data collected by the patch to one or more external devices for further processing.

A CUT may, for example, include a cavity formed in a CMOS wafer, with a membrane overlying the cavity, and in some embodiments sealing the cavity. Electrodes may be provided to create a transducer cell from the covered cavity structure. The CMOS wafer may include integrated circuitry to which the transducer cell may be connected. The transducer cell and CMOS wafer may be monolithically integrated, thus forming an integrated ultrasonic transducer cell and integrated circuit on a single substrate (the CMOS wafer).

The TX circuitry 1604 (if included) may, for example, generate pulses that drive the individual elements of, or one or more groups of elements within, the transducer array(s) 1602 so as to generate acoustic signals to be used for imaging. The RX circuitry 1606, on the other hand, may receive and process electronic signals generated by the individual elements of the transducer array(s) 102 when acoustic signals impinge upon such elements.

In some embodiments, the timing and control circuit 1608 may, for example, be responsible for generating all timing and control signals that are used to synchronize and coordinate the operation of the other elements in the device 1600. In the example shown, the timing and control circuit 1608 is driven by a single clock signal CLK supplied to an input port 1616. The clock signal CLK may, for example, be a high-frequency clock used to drive one or more of the on-chip circuit components. In some embodiments, the clock signal CLK may, for example, be a 1.5625 GHz or 2.5 GHz clock used to drive a high-speed serial output device (not shown in FIG. 16) in the signal conditioning/processing circuit 1610, or a 20 Mhz or 40 MHz clock used to drive other digital components on the semiconductor die 1612, and the timing and control circuit 1608 may divide or multiply the clock CLK, as necessary, to drive other components on the die 1612. In other embodiments, two or more clocks of different frequencies (such as those referenced above) may be separately supplied to the timing and control circuit 1608 from an off-chip source.

The power management circuit 1618 may, for example, be responsible for converting one or more input voltages VIN from an off-chip source into voltages needed to carry out operation of the chip, and for otherwise managing power consumption within the device 1600.

In some embodiments, for example, a single voltage (e.g., 12V, 80V, 100V, 120V, etc.) may be supplied to the chip and the power management circuit 1618 may step that voltage up or down, as necessary, using a charge pump circuit or via some other DC-to-DC voltage conversion mechanism. In other embodiments, multiple different voltages may be supplied separately to the power management circuit 1618 for processing and/or distribution to the other on-chip components.

As shown in FIG. 16, in some embodiments, a HIFU controller 1620 may be integrated on the semiconductor die 1612 so as to enable the generation of HIFU signals via one or more elements of the transducer array(s) 1602. In other embodiments, a HIFU controller for driving the transducer array(s) 1602 may be located off-chip, or even within a device separate from the device 1600. That is, aspects of the present disclosure relate to provision of ultrasound-on-a-chip HIFU systems, with and without ultrasound imaging capability. It should be appreciated, however, that some embodiments may not have any HIFU capabilities and thus may not include a HIFU controller 1620.

Moreover, it should be appreciated that the HIFU controller 1620 may not represent distinct circuitry in those embodiments providing HIFU functionality. For example, in some embodiments, the remaining circuitry of FIG. 16 (other than the HIFU controller 1620) may be suitable to provide ultrasound imaging functionality and/or HIFU, i.e., in some embodiments the same shared circuitry may be operated as an imaging system and/or for HIFU. Whether or not imaging or HIFU functionality is exhibited may depend on the power provided to the system. HIFU typically operates at higher powers than ultrasound imaging. Thus, providing the system a first power level (or voltage level) appropriate for imaging applications may cause the system to operate as an imaging system, whereas providing a higher power level (or voltage level) may cause the system to operate for HIFU. Such power management may be provided by off-chip control circuitry in some embodiments.

In addition to using different power levels, imaging and HIFU applications may utilize different waveforms. Thus, waveform generation circuitry may be used to provide suitable waveforms for operating the system as either an imaging system or a HIFU system.

In some embodiments, the system may operate as both an imaging system and a HIFU system (e.g., capable of providing image-guided HIFU). In some such embodiments, the same on-chip circuitry may be utilized to provide both functions, with suitable timing sequences used to control the operation between the two modalities.

In the example shown, one or more output ports 1614 may output a high-speed serial data stream generated by one or more components of the signal conditioning/processing circuit 1610. Such data streams may, for example, be generated by one or more USB 3.0 modules, and/or one or more 10 GB, 40 GB, or 100 GB Ethernet modules, integrated on the semiconductor die 1612. In some embodiments, the signal stream produced on output port 1614 can be fed to a computer, tablet, or smartphone for the generation and/or display of 2-dimensional, 3-dimensional, and/or tomographic images. In embodiments in which image formation capabilities are incorporated in the signal conditioning/processing circuit 1610, even relatively low-power devices, such as smartphones or tablets which have only a limited amount of processing power and memory available for application execution, can display images using only a serial data stream from the output port 1614. As noted above, the use of on-chip analog-to-digital conversion and a high-speed serial data link to offload a digital data stream is one of the features that helps facilitate an "ultrasound on a chip" solution according to some embodiments of the technology described herein.

Devices 1600 such as that shown in FIG. 16 may be used in any of a number of imaging and/or treatment (e.g., HIFU) applications, and the particular examples discussed herein should not be viewed as limiting. In one illustrative implementation, for example, an imaging device including an N×M planar or substantially planar array of CMUT elements may itself be used to acquire an ultrasonic image of a subject, e.g., a person's abdomen, by energizing some or all of the elements in the array(s) 1602 (either together or individually) during one or more transmit phases, and receiving and processing signals generated by some or all of the elements in the array(s) 1602 during one or more receive phases, such that during each receive phase the CMUT elements sense acoustic signals reflected by the subject. In other implementations, some of the elements in the array(s) 1602 may be used only to transmit acoustic signals and other elements in the same array(s) 1602 may be simultaneously used only to receive acoustic signals. Moreover, in some implementations, a single imaging device may include a P×Q array of individual devices, or a P×Q array of individual N×M planar arrays of CMUT elements, which components can be operated in parallel, sequentially, or according to some other timing scheme so as to allow data to be accumulated from a larger number of CMUT elements than can be embodied in a single device 1600 or on a single die 1612.

In yet other implementations, a pair of imaging devices can be positioned so as to straddle a subject, such that one or more CMUT elements in the device(s) 1600 of the imaging device on one side of the subject can sense acoustic signals generated by one or more CMUT elements in the device(s) 1600 of the imaging device on the other side of the subject, to the extent that such pulses were not substantially attenuated by the subject. Moreover, in some implementations, the same device 1600 can be used to measure both the scattering of acoustic signals from one or more of its own CMUT elements as well as the transmission of acoustic signals from one or more of the CMUT elements disposed in an imaging device on the opposite side of the subject.

Figure 17:
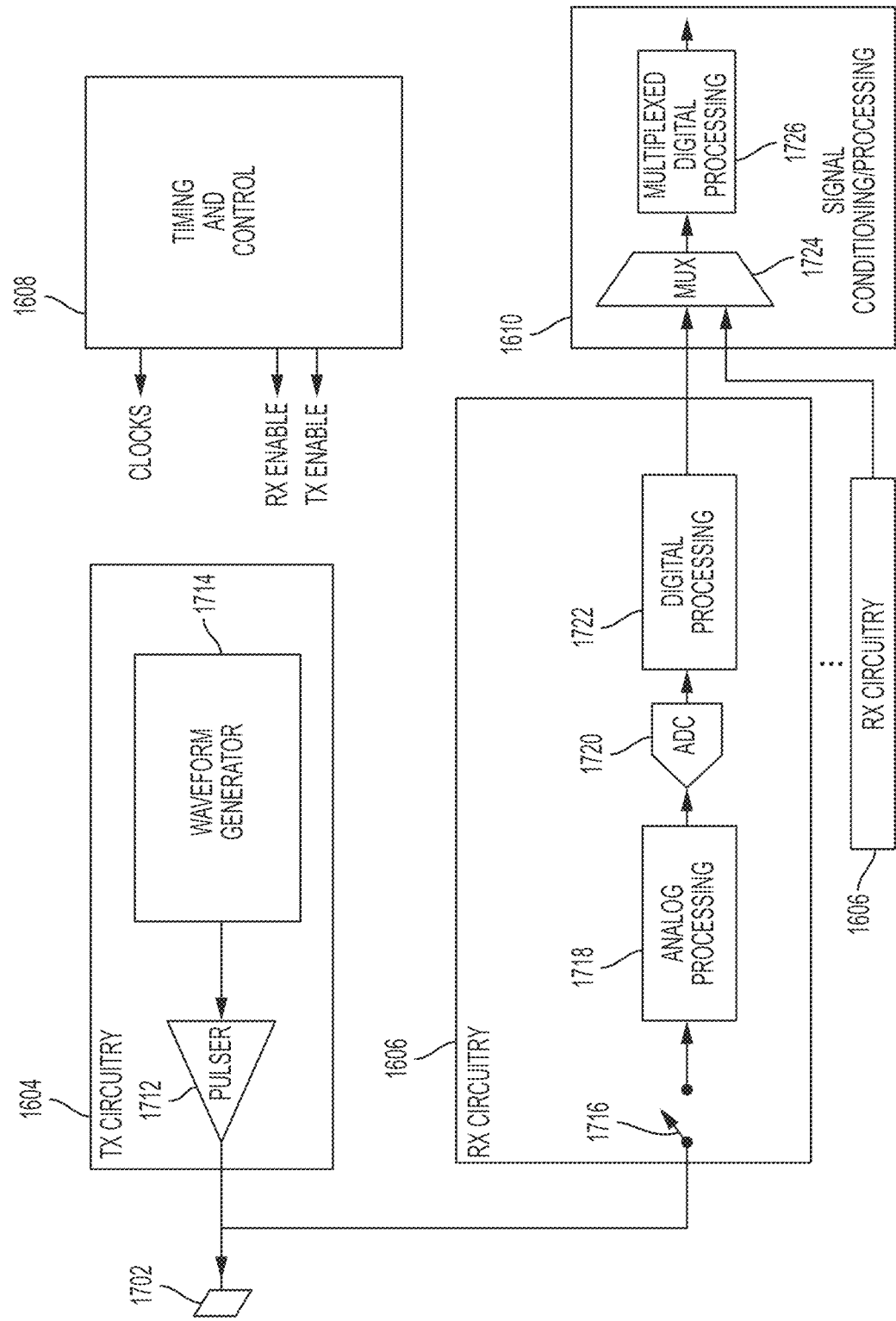
FIG. 17 shows a detailed block diagram of the exemplary ultrasound device shown in FIG. 16 according to some embodiments of the disclosure.

FIG. 17 is a block diagram illustrating how, in some embodiments, the TX circuitry 1604 and the RX circuitry 1606 for a given transducer element 1702 may be used either to energize the transducer element 1702 to emit an ultrasonic pulse, or to receive and process a signal from the transducer element 1702 representing an ultrasonic pulse sensed by it. In some implementations, the TX circuitry 1604 may be used during a "transmission" phase, and the RX circuitry may be used during a "reception" phase that is non-overlapping with the transmission phase. In other implementations, one of the TX circuitry 1604 and the RX circuitry 1606 may simply not be used in a given device 1600, such as when a pair of ultrasound units is used for only transmissive imaging. As noted above, in some embodiments, an ultrasound device 1600 may alternatively employ only TX circuitry 1604 or only RX circuitry 1606, and aspects of the present technology do not necessarily require the presence of both such types of circuitry. In various embodiments, TX circuitry 1604 and/or RX circuitry 1606 may include a TX circuit and/or an RX circuit associated with a single transducer cell (e.g., a CUT or CMUT), a group of two or more transducer cells within a single transducer element 1702, a single transducer element 1702 comprising a group of transducer cells, a group of two or more transducer elements 1702 within an array 1602, or an entire array 1602 of transducer elements 1702.

In the example shown in FIG. 17, the TX circuitry 1604/RX circuitry 1606 includes a separate TX circuit and a separate RX circuit for each transducer element 1702 in the array(s) 1602, but there is only one instance of each of the timing & control circuit 1608 and the signal conditioning/processing circuit 1610. Accordingly, in such an implementation, the timing & control circuit 1608 may be responsible for synchronizing and coordinating the operation of all of the TX circuitry 1604/RX circuitry 1606 combinations on the die 1612, and the signal conditioning/processing circuit 1610 may be responsible for handling inputs from all of the RX circuitry 1606 on the die 1612. In other embodiments, timing and control circuit 1608 may be replicated for each transducer element 1702 or for a group of transducer elements 1702.

As shown in FIG. 17, in addition to generating and/or distributing clock signals to drive the various digital components in the device 1600, the timing & control circuit 1608 may output either an "TX enable" signal to enable the operation of each TX circuit of the TX circuitry 1604, or an "RX enable" signal to enable operation of each RX circuit of the RX circuitry 1606. In the example shown, a switch 1716 in the RX circuitry 1606 may always be opened before the TX circuitry 1604 is enabled, so as to prevent an output of the TX circuitry 1604 from driving the RX circuitry 1606. The switch 1716 may be closed when operation of the RX circuitry 1606 is enabled, so as to allow the RX circuitry 1606 to receive and process a signal generated by the transducer element 1702.

As shown, the TX circuitry 1604 for a respective transducer element 1702 may include both a waveform generator 1714 and a pulser 1712. The waveform generator 1714 may, for example, be responsible for generating a waveform that is to be applied to the pulser 1712, so as to cause the pulser 1712 to output a driving signal to the transducer element 1702 corresponding to the generated waveform.

In the example shown in FIG. 17, the RX circuitry 1606 for a respective transducer element 1702 includes an analog processing block 1718, an analog-to-digital converter (ADC) 1720, and a digital processing block 1722. The ADC 1720 may, for example, comprise a 10-bit or 12-bit, 20 Msps, 25 Msps, 40 Msps, 50 Msps, or 80 Msps ADC.

After undergoing processing in the digital processing block 1722, the outputs of all of the RX circuits on the semiconductor die 1612 (the number of which, in this example, is equal to the number of transducer elements 1702 on the chip) are fed to a multiplexer (MUX) 1724 in the signal conditioning/processing circuit 1610. In other embodiments, the number of transducer elements is larger than the number of RX circuits, and several transducer elements provide signals to a single RX circuit. The MUX 1724 multiplexes the digital data from the RX circuits, and the output of the MUX 1724 is fed to a multiplexed digital processing block 1726 in the signal conditioning/processing circuit 1610, for final processing before the data is output from the semiconductor die 1612, e.g., via one or more high-speed serial output ports 1614. The MUX 1724 is optional, and in some embodiments parallel signal processing is performed. A high-speed serial data port may be provided at any interface between or within blocks, any interface between chips and/or any interface to a host. Various components in the analog processing block 1718 and/or the digital processing block 1722 may reduce the amount of data that needs to be output from the semiconductor die 1612 via a high-speed serial data link or otherwise. In some embodiments, for example, one or more components in the analog processing block 1718 and/or the digital processing block 1722 may thus serve to allow the RX circuitry 1606 to receive transmitted and/or scattered ultrasound pressure waves with an improved signal-to-noise ratio (SNR) and in a manner compatible with a diversity of waveforms. The inclusion of such elements may thus further facilitate and/or enhance the disclosed "ultrasound-on-a-chip" solution in some embodiments.

The ultrasound devices described herein may be implemented in any of a variety of physical configurations including as part of a handheld device (which may include a screen to display obtained images) or as part of a patch configured to be affixed to the subject.

In some embodiments, an ultrasound device may be embodied in a handheld device 1802 illustrated in FIGS. 18A and 18B. Handheld device 1802 may be held against (or near) a subject 1800 and used to image the subject. Handheld device 1802 may comprise an ultrasound device and display 1804, which in some embodiments, may be a touchscreen. Display 1804 may be configured to display images of the subject (e.g., ultrasound images) generated within handheld device 1802 using ultrasound data gathered by the ultrasound device within device 1802.

In some embodiments, handheld device 1802 may be used in a manner analogous to a stethoscope. A medical professional may place handheld device 1802 at various positions along a patient's body. The ultrasound device within handheld device 1802 may image the patient. The data obtained by the ultrasound device may be processed and used to generate image(s) of the patient, which image(s) may be displayed to the medical professional via display 1804. As such, a medical professional could carry the handheld device 1802 (e.g., around their neck or in their pocket) rather than carrying around multiple conventional devices, which is burdensome and impractical.

Figure 18C:
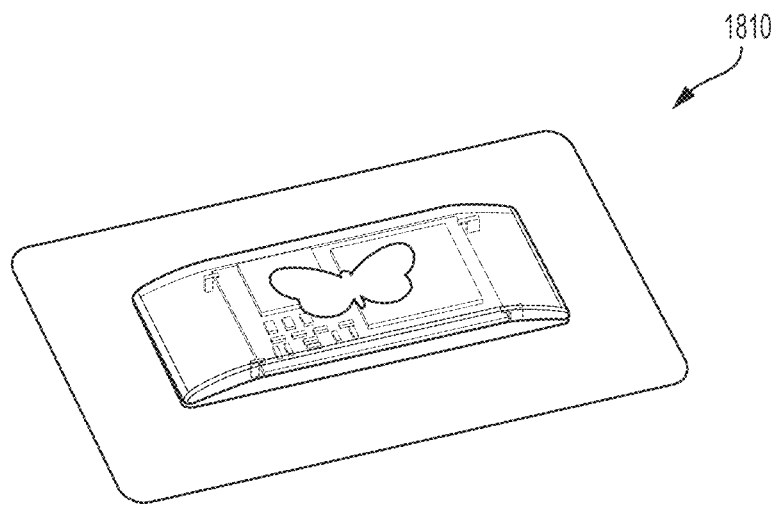
FIGS. 18C-18E show an exemplary patch comprising an ultrasound device according to some embodiments of the disclosure.
Figure 18D:
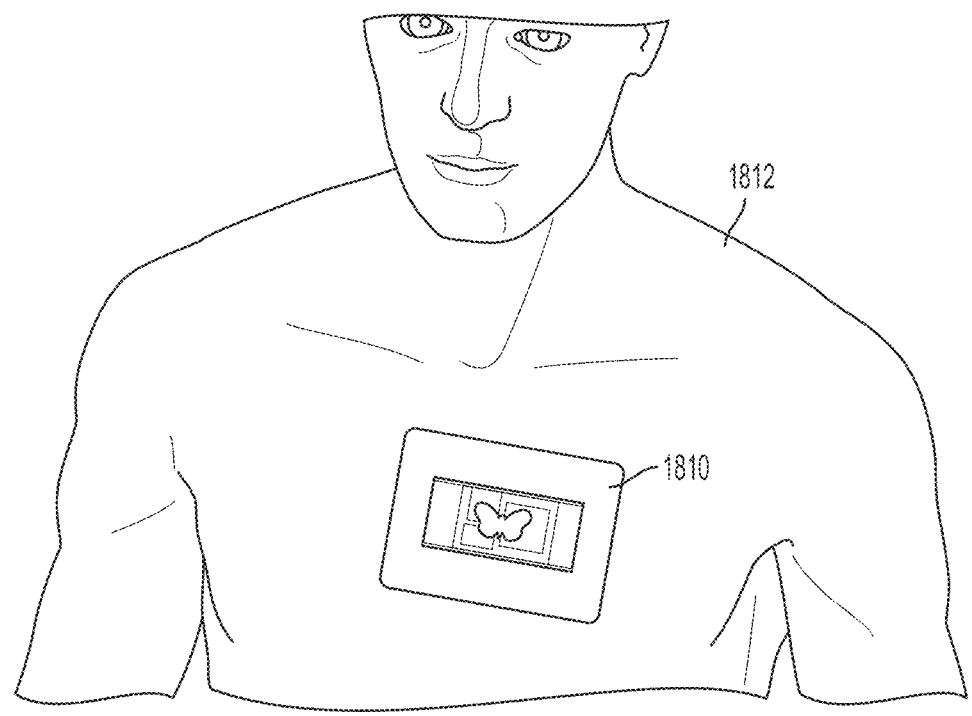
Figure 18E:
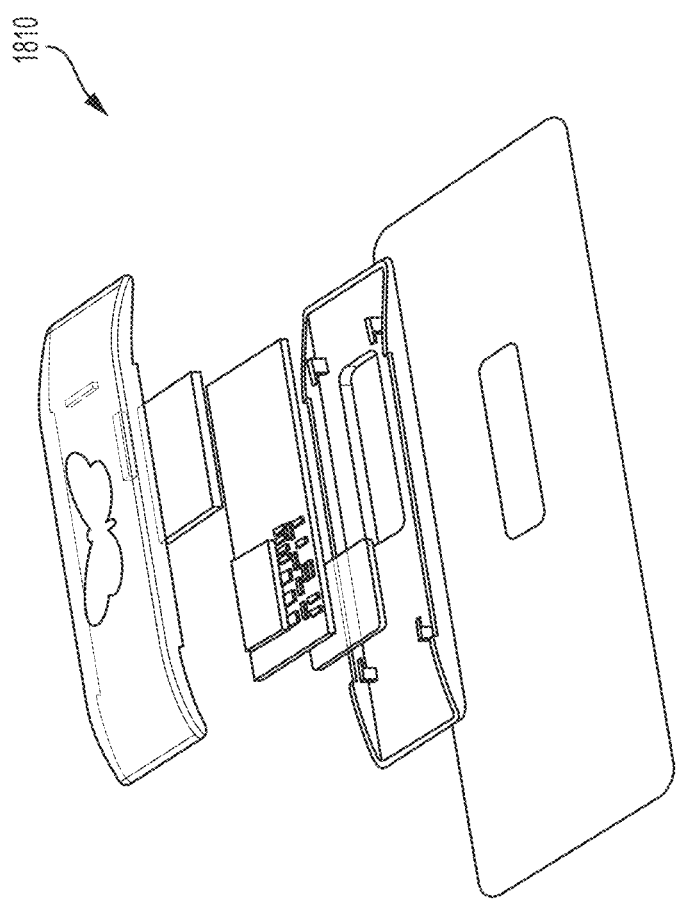

In some embodiments, an ultrasound device may be embodied in a patch that may be coupled to a patient. For example, FIGS. 18C and 18D illustrate a patch 1810 coupled to patient 1812. The patch 1810 may be configured to transmit, wirelessly, data collected by the patch 1810 to one or more external devices for further processing. FIG. 18E shows an exploded view of patch 1810.

In some embodiments, an ultrasound device may be embodied in handheld device 1820 shown in FIG. 18F. Handheld device 1820 may be configured to transmit data collected by the device 1820 wirelessly to one or more external device for further processing. In other embodiments, handheld device 1820 may be configured transmit data collected by the device 1820 to one or more external devices using one or more wired connections, as aspects of the technology described herein are not limited in this respect.

Various aspects of the present disclosure may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Further, some actions are described as taken by a "operator" or "subject." It should be appreciated that a "operator" or "subject" need not be a single individual, and that in some embodiments, actions attributable to an "operator" or "subject" may be performed by a team of individuals and/or an individual in combination with computer-assisted tools or other mechanisms. Further, it should be appreciated that, in some instances, a "subject" may be the same person as the "operator." For example, an individual may be imaging themselves with an ultrasound device and, thereby, act as both the "subject" being imaged and the "operator" of the ultrasound device.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:
1. An ultrasound system, comprising:
an ultrasound device; and
a handheld computing device in operative communication with the ultrasound device, the handheld computing device comprising a display screen and configured to:
obtain an electronic medical record of a subject;
identify an organ associated with medical information contained in the electronic medical record;
identify a target anatomical view of the identified organ of the subject to be imaged by the ultrasound device;

display, on the display screen, a coarse instruction for capturing ultrasound data representing the target anatomical view, the coarse instruction comprising:
- a graphical image of the subject; and
  - a graphical indication of where an operator should place the ultrasound device in order to capture the ultrasound data representing the target anatomical view, wherein the indication is superimposed on the graphical image of the subject; and
- display, on the display screen, a fine instruction for capturing the ultrasound data representing the target anatomical view, the fine instruction comprising an instruction selected from the group consisting of translating, rotating, and tilting the ultrasound device in order to capture the ultrasound data representing the target anatomical view.

2. The ultrasound system of claim 1, wherein the handheld computing device is further configured to input the ultrasound data to a neural network to determine a diagnosis of a medical condition of the subject.

3. The ultrasound system of claim 1, wherein the handheld computing device does not display ultrasound images generated based on the ultrasound data captured by the ultrasound device while displaying the coarse instruction or the fine instruction.

4. The ultrasound system of claim 1, wherein the medical information contained in the electronic medical record comprises a symptom.

5. The ultrasound system of claim 1, wherein the handheld computing device is configured to access the electronic medical record on a remote server.

6. The ultrasound system of claim 5, wherein the handheld computing device is configured to scan a barcode to obtain information for accessing the electronic medical record on the remote server.

7. The ultrasound system of claim 1, wherein when the electronic medical record indicates that the subject has symptoms of congestive heart failure, the handheld computing device is configured to identify a heart as the organ and to identify a parasternal long axis view of the heart as the target anatomical view.

8. The ultrasound system of claim 1, wherein the coarse instruction further comprises text comprising a message instructing the operator where to place the ultrasound device in order to capture the image of the target anatomical view.

9. The ultrasound system of claim 1, wherein the handheld computing device is further configured to:
- determine when the ultrasound device is properly positioned;
- provide a confirmation that the ultrasound device is properly positioned; and
- provide a message instructing the operator to hold the ultrasound device in place.

10. The ultrasound system of claim 1, wherein the handheld computing device is configured, when identifying the target anatomical view of the subject to be imaged by the ultrasound device, to identify a target anatomical view which can be used to calculate ejection fraction.

11. The ultrasound system of claim 1, wherein the handheld computing device is further configured to:
- calculate results based on ultrasound images collected by the ultrasound system, wherein the results comprise ejection fraction and ventricle diameter; and
- display the ejection fraction and ventricle diameter results.

12. The ultrasound system of claim 11, wherein the handheld computing device is further configured to display whether the ejection fraction result or the ventricle diameter result is in an abnormal range.

13. The ultrasound system of claim 1, wherein the fine instruction comprises an augmented reality interface comprising:
- a non-acoustic image of the subject captured by a camera of the computing device; and
- an instruction superimposed on the non-acoustic image of the subject indicating how the operator should move the ultrasound device in order to capture the image of the target anatomical view.

14. The ultrasound system of claim 13, wherein the fine instruction further comprises text instructing the operator how to move the ultrasound device.

15. The ultrasound system of claim 13, wherein the instruction superimposed on the non-acoustic image of the subject indicating how the operator should move the ultrasound device in order to capture the image of the target anatomical view is animated.

16. The ultrasound system of claim 13, wherein the camera comprises a front-facing camera, and the subject is the operator.

17. The ultrasound system of claim 1, wherein the handheld computing device is further configured to prompt the operator to input whether the subject is experiencing paroxysmal nocturnal dyspnea.

18. The ultrasound system of claim 1, wherein the handheld computing device is further configured to:
- instruct the operator to capture an image of a barcode with a camera of the computing device;
- obtain medical information of the subject using the barcode;
- display the medical information of the subject; and
- prompt the operator to confirm that the medical information is correct.

19. The ultrasound system of claim 1, wherein the handheld computing device is further configured to instruct the operator to apply gel to the ultrasound device.

20. The ultrasound system of claim 1, wherein the handheld computing device comprises a smartphone or tablet.

* * * * *